(12) United States Patent
Nishino et al.

(10) Patent No.: US 9,682,931 B2
(45) Date of Patent: Jun. 20, 2017

(54) ARYLOYL(OXY OR AMINO)PENTAFLUOROSULFANYLBENZENE COMPOUND, PHARMACEUTICALLY ACCEPTABLE SALT THEREOF, AND PRODRUGS THEREOF

(71) Applicant: UBE INDUSTRIES, LTD., Ube-shi (JP)

(72) Inventors: Shigeyoshi Nishino, Ube (JP); Hidetaka Shima, Ube (JP); Hiroyuki Oda, Ube (JP); Tetsuro Shimano, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 15/032,015

(22) PCT Filed: Nov. 4, 2014

(86) PCT No.: PCT/JP2014/079259
§ 371 (c)(1),
(2) Date: Apr. 25, 2016

(87) PCT Pub. No.: WO2015/064764
PCT Pub. Date: May 7, 2015

(65) Prior Publication Data
US 2016/0244407 A1    Aug. 25, 2016

(30) Foreign Application Priority Data

Nov. 1, 2013 (JP) .................... 2013-228817

(51) Int. Cl.
| | | |
|---|---|---|
| *A61K 31/167* | (2006.01) | |
| *A61K 31/216* | (2006.01) | |
| *A61K 31/36* | (2006.01) | |
| *C07C 381/00* | (2006.01) | |
| *C07D 207/327* | (2006.01) | |
| *C07D 207/34* | (2006.01) | |
| *C07D 213/81* | (2006.01) | |
| *C07D 213/82* | (2006.01) | |
| *C07D 231/12* | (2006.01) | |
| *C07D 231/14* | (2006.01) | |
| *C07D 233/90* | (2006.01) | |
| *C07D 237/24* | (2006.01) | |
| *C07D 239/28* | (2006.01) | |
| *C07D 239/34* | (2006.01) | |

(Continued)

(52) U.S. Cl.
CPC .......... *C07C 381/00* (2013.01); *A61K 31/167* (2013.01); *A61K 31/216* (2013.01); *A61K 31/36* (2013.01); *C07D 207/327* (2013.01); *C07D 207/34* (2013.01); *C07D 213/81* (2013.01); *C07D 213/82* (2013.01); *C07D 231/12* (2013.01); *C07D 231/14* (2013.01); *C07D 233/90* (2013.01); *C07D 237/24* (2013.01); *C07D 239/28* (2013.01); *C07D 239/34* (2013.01); *C07D 241/24* (2013.01); *C07D 263/34* (2013.01); *C07D 277/56* (2013.01); *C07D 307/68* (2013.01); *C07D 311/16* (2013.01); *C07D 317/60* (2013.01); *C07D 333/38* (2013.01)

(58) Field of Classification Search
CPC .. C07C 381/00; A61K 31/167; A61K 31/216; A61K 31/36; C07D 231/12; C07D 231/14; C07D 241/24; C07D 239/34; C07D 239/28; C07D 237/24; C07D 233/90; C07D 277/56; C07D 213/82; C07D 213/81; C07D 207/34; C07D 207/327; C07D 307/68; C07D 333/38; C07D 263/34; C07D 311/16; C07D 317/60; C07D 263/03
See application file for complete search history.

(56) References Cited

U.S. PATENT DOCUMENTS

| | | | |
|---|---|---|---|
| 3,117,158 A | 1/1964 | Sheppard et al. | |
| 9,278,981 B2 * | 3/2016 | Furet .................... | C07D 401/14 |
| 2010/0099909 A1 | 4/2010 | Nishino et al. | |

FOREIGN PATENT DOCUMENTS

| | | |
|---|---|---|
| CA | 2536459 A1 | 3/2005 |
| CA | 2551057 A1 | 5/2005 |

(Continued)

OTHER PUBLICATIONS

Sheppard et al., Arylsulfur Pentafluorides, J. Am. Chem. Soc., vol. 84, No. 16, pp. 3064-3072, 1962.

(Continued)

*Primary Examiner* — Paul A Zucker
*Assistant Examiner* — Mark Luderer
(74) *Attorney, Agent, or Firm* — Knobbe Martens Olson & Bear LLP

(57) ABSTRACT

An aryloyl(oxy or amino)pentafluorosulfanylbenzene compound having pharmacological action. The aryloyl(oxy or amino)pentafluorosulfanylbenzene compound is represented by general formula (A-I), a pharmaceutically acceptable salt thereof, and a prodrug thereof,

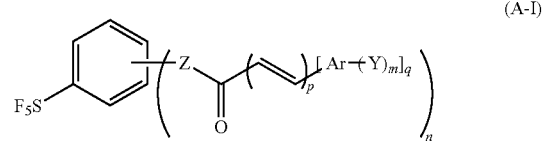

(A-I)

wherein all of parameters represent the same meanings as defined in the specification.

2 Claims, 5 Drawing Sheets

(51) Int. Cl.
*C07D 241/24* (2006.01)
*C07D 263/34* (2006.01)
*C07D 277/56* (2006.01)
*C07D 307/68* (2006.01)
*C07D 311/16* (2006.01)
*C07D 317/60* (2006.01)
*C07D 333/38* (2006.01)

(56) References Cited

FOREIGN PATENT DOCUMENTS

| | | |
|---|---|---|
| JP | A-2010-120926 | 6/2010 |
| JP | B-4516965 | 8/2010 |
| JP | B-4528304 | 8/2010 |
| JP | A-2010-222279 | 10/2010 |

OTHER PUBLICATIONS

International Preliminary Report on Patentability in International Application No. PCT/JP2014/079259 dated May 12, 2016.

\* cited by examiner

ARYLOYL(OXY OR AMINO)PENTAFLUOROSULFANYLBENZENE COMPOUND, PHARMACEUTICALLY ACCEPTABLE SALT THEREOF, AND PRODRUGS THEREOF

This application is the U.S. National Phase under 35 U.S.C. §371 of International Application No. PCT/JP2014/079259, filed Nov. 4, 2014, designating the U.S., and published in Japanese as WO 2015/064764 on May 7, 2015, which claims priority to Japanese Patent Application No. 2013-228817, filed Nov. 1, 2013, the entire contents of which are incorporated herein by reference.

TECHNICAL FIELD

The present invention relates to novel aryloyl(oxy or amino)pentafluorosulfanylbenzene compounds, prodrugs thereof and pharmaceutically acceptable salts thereof, and also to methods of producing these, and to pharmaceutical compositions containing these.

BACKGROUND ART

In the past, among pentafluorosulfanylbenzene compounds, pentafluorosulfanylphenyl-substituted benzoylguanidines (for example, see Patent Document 1) and pentafluorosulfanylbenzoyl guanidines (for example, see Patent Document 2), for example, have been known as compounds useful as medicaments.

PRIOR ART REFERENCES

Patent Documents

Patent Document 1: Japanese Patent No. 4516965
Patent Document 2: Japanese Patent No. 4528304

SUMMARY OF THE INVENTION

Problem to be Solved by the Invention

However, aryloyl(oxy or amino)pentafluorosulfanylbenzene compounds, and their pharmacological effects have not been known at all.

Means for Solving the Problem

The present invention relates to the following items.
1. An aryloyl(oxy or amino)pentafluorosulfanylbenzene compound represented by general formula (A-I), a pharmaceutically acceptable salt thereof, or a prodrug thereof.

(A-I)

(wherein,
p is an integer of 0 or 1;
q is an integer of 0 or 1;
m is an integer of 0 to 5;
n is an integer of 1 to 3;
Z represents —O— or —NH—;

Ar represents an aromatic ring group or heteroaromatic ring group;
Y represents —OR, —SR, nitro, amino or halogen atom;
R represents hydrogen atom, alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$).
Herein $R^2$ to $R^{11}$, independently of one another, represent hydrogen atom, hydroxy, alkyl, cycloalkyl, alkenyl, alkynyl, aralkyl, aryl, heteroaryl, alkoxy, aryloxy or amino; and among $R^2$ to $R^{11}$, two adjacent groups may be bonded together to form a ring.
If m and/or n is 2 or more, plural Y may be identical to or different from each other, and adjacent Y groups may be bonded together to form a ring.
In addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino.)
2. The aryloyl(oxy or amino)pentafluorosulfanylbenzene compound according to Claim 1, which is represented by general formula (I), a pharmaceutically acceptable salt thereof, or a prodrug thereof.

(I)

(wherein,
p is an integer of 0 or 1;
m is an integer of 0 to 5;
n is an integer of 1 to 3;
Z represents —O— or —NH—;
R represents hydrogen atom, alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$).
Herein $R^2$ to $R^{11}$, independently of one another, represent hydrogen atom, hydroxy, alkyl, cycloalkyl, alkenyl, alkynyl, aralkyl, aryl, heteroaryl, alkoxy, aryloxy or amino; and among $R^2$ to $R^{11}$, two adjacent groups may be bonded together to form a ring.
If m and/or n is 2 or more, plural R may be identical to or different from each other, and adjacent R groups may be bonded together to form a ring.
In addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino.)
3. A process for producing an aryloyl(oxy or amino) pentafluorosulfanylbenzene compound represented by the general formula (A-I), the process comprising a step of:
reacting, in the presence of a base, a pentafluorosulfanylbenzene compound represented by general formula (A-II):

(A-II)

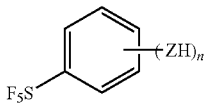

(wherein,
Z represents —O— or —NH—;
n is an integer of 1 to 3;
in addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino;)
with a compound represented by general formula (A-III):

(A-III)

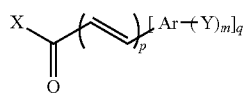

(wherein,
m, p, q, Ar and Y each represent the meanings as defined for formula (A-I);
X represents a group selected from halogen atom, hydroxy, optionally substituted nitrophenoxy, optionally substituted nitro benzoyloxy, azide group (—N₃), pivaloyloxy, 1-imidazolyl, 1-triazolyl, and 1-tetrazolyl, and if R is alkyl, alkenyl, alkynyl or aralkyl, X may also represents alkyloxy, alkenyloxy, alkynyloxy or aralkyloxy.).

4. A process for producing an aryloyl(oxy or amino) pentafluorosulfanylbenzene compound represented by the general formula (I), the process comprising a step of:
reacting, in the presence of a base, a pentafluorosulfanylbenzene compound represented by general formula (II):

(II)

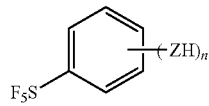

(wherein,
Z represents —O— or —NH—;
n is an integer of 1 to 3;
in addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino;)
with a compound represented by general formula (III):

(III)

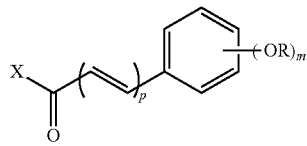

(wherein,
m, p, and R each represent the meanings as defined for formula (I);
X represents a group selected from halogen atom, hydroxy, optionally substituted nitrophenoxy, optionally substituted nitro benzoyloxy, azide group (—N₃), pivaloyloxy, 1-imidazolyl, 1-triazolyl, and 1-tetrazolyl, and if R is alkyl, alkenyl, alkynyl or aralkyl, X may also represents alkyloxy, alkenyloxy, alkynyloxy or aralkyloxy.).

5. A pharmaceutical composition comprising the aryloyl (oxy or amino)pentafluorosulfanylbenzene compound, the pharmaceutically acceptable salt thereof, or the prodrug thereof as described in the above item 1 or 2.

6. The pharmaceutical composition according to the above item 5, serving as at least one selected from the group consisting of antimicrobial agents, bactericidal agents, topoisomerase inhibitors, antiviral agents, anticancer agents, angiogenesis inhibitors, cancer metastasis inhibitors, antiallergic agents, antioxidants, anti-inflammatory agents, antiulcer agents, periodontal disease therapeutic/prophylactic agents, caries therapeutic/prophylactic agents, osteoporosis therapeutic/prophylactic agents, rheumatoid arthritis therapeutic/prophylactic agents, osteoarthritis therapeutic/prophylactic agents, Alzheimer's disease therapeutic agents, diabetes therapeutic/prophylactic agents, arteriosclerosis therapeutic/prophylactic agents, myocardial infarction prophylactic agents, platelet aggregation inhibitors, lipid metabolism improving agents, cholesterol lowering agents and blood pressure control agents.

7. The pharmaceutical composition according to the above item 5, serving as at least one medicinal agent selected from the group consisting of antimicrobial agents, bactericidal agents, topoisomerase inhibitors, antiviral agents, anticancer agents, angiogenesis inhibitors and antiallergic agents.

Effect of the Invention

Aryloyl(oxy or amino)pentafluorosulfanylbenzene compounds of the present invention are novel compounds and have various efficacies as pharmaceutical compositions,

EMBODIMENTS OF THE INVENTION

Figure 1:
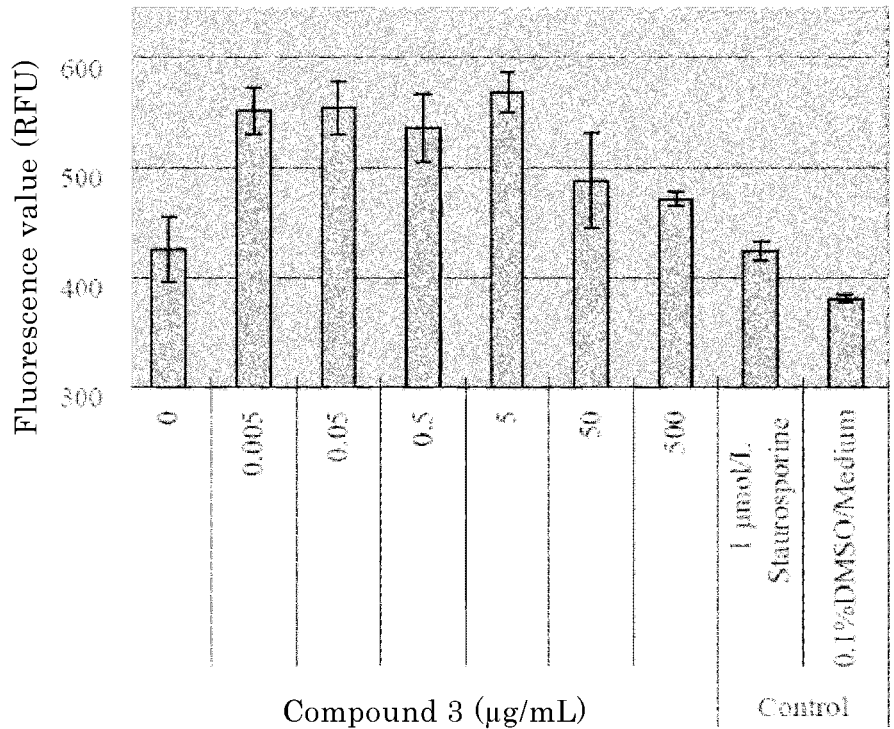
FIG. 1 shows the results of quantitative determination of caspase 3/7 in A549 cells in Example B3.

Aryloyl(oxy or amino)pentafluorosulfanylbenzene compounds of the present invention are represented by formula (A-I). Hereinafter, aryloyl(oxy or amino)pentafluorosulfanylbenzene compounds represented by formula (A-I) of the present invention may be referred to as simply "compound(s) represented by formula (A-I)", "compound(s) (A-I)" or "aryloyl(oxy or amino)pentafluorosulfanylbenzene compound(s)".

A preferred aspect of Aryloyl(oxy or amino)pentafluorosulfanylbenzene compounds of the present invention are represented by formula (I). Hereinafter, aryloyl(oxy or amino)pentafluorosulfanylbenzene compounds represented by formula (I) of the present invention may be referred to as simply "compound(s) represented by formula (I)" or "compound(s) (I)".

The compound (A-I) and compound (I) of the present invention, as described later, have at least one action selected from excellent antimicrobial action, bactericidal action, antiviral action, anticancer action, angiogenesis inhibitory action, antiallergic action, inhibitory action on degranulation from mast cells, cell proliferation inhibitory action, apoptosis-inducing action, gene expression suppressive action, topoisomerase inhibitory action, antioxidative action and anti-inflammatory action. Accordingly, the present invention can provide a novel compound having excellent properties as at least one pharmaceutical composition selected from antimicrobial agents, bactericidal agents, topoisomerase inhibitors, antiviral agents, anticancer agents, angiogenesis inhibitors, cancer metastasis inhibitors, antiallergic agents, antioxidants, anti-inflammatory agents, anti-ulcer agents, periodontal disease therapeutic/prophylactic agent and caries therapeutic/prophylactic agent.

The compound (A-I) and compound (I) of the present invention are expected to be used as a pharmaceutical composition selected from the group consisting of osteoporosis therapeutic/prophylactic agents, Alzheimer's disease therapeutic agents, arteriosclerosis therapeutic/prophylactic agents, diabetes therapeutic/prophylactic agents, rheumatoid arthritis therapeutic/prophylactic agents, platelet aggregation inhibitors, lipid metabolism improving agents and cholesterol lowering agents.

Compound (A-I) and compound (I) of the present invention will be described below. Compound (A-I) is represented by the following general formula (A-I) and compound (I) is represented by the following general formula (I).

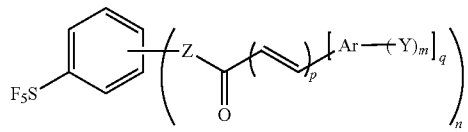

(wherein,
p is an integer of 0 or 1;
q is an integer of 0 or 1;
m is an integer of 0 to 5;
n is an integer of 1 to 3;
Z represents —O— or —NH—;
Ar represents an aromatic ring group or heteroaromatic ring group;
Y represents —OR, —SR, nitro, amino or halogen atom;
R represents hydrogen atom, alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$).
Herein $R^2$ to $R^{11}$, independently of one another, represent hydrogen atom, hydroxy, alkyl, cycloalkyl, alkenyl, alkynyl, aralkyl, aryl, heteroaryl, alkoxy, aryloxy or amino; and among $R^2$ to $R^{11}$, two adjacent groups may be bonded together to form a ring.

If m and/or n is 2 or more, plural Y may be identical to or different from each other, and adjacent Y groups may be bonded together to form a ring.

In addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino.)

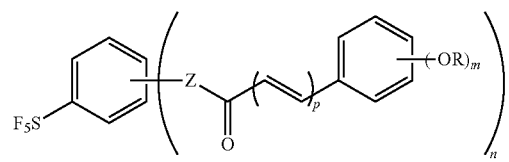

(wherein,
p is an integer of 0 or 1;
m is an integer of 0 to 5;
n is an integer of 1 to 3;
Z represents —O— or —NH—;
R represents hydrogen atom, alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$).
Herein $R^2$ to $R^{11}$, independently of one another, represent hydrogen atom, hydroxy, alkyl, cycloalkyl, alkenyl, alkynyl, aralkyl, aryl, heteroaryl, alkoxy, aryloxy or amino; and among $R^2$ to $R^{11}$, two adjacent groups may be bonded together to form a ring.

If m and/or n is 2 or more, plural R may be identical to or different from each other, and adjacent R groups may be bonded together to form a ring.

In addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino.)

As to groups and parameters common to formula (A-I) and formula (I), the following description applies to both formulae.

In general formula (A-I) and general formula (I), p represents an integer of 0 or 1. m represents an integer of 0 to 5, preferably an integer of 0 to 3. n represents an integer of 1 to 3, preferably 1 or 2.

In general formula (A-I), q represents an integer of 0 or 1, and preferably q is 1. If q is 0, p is preferably 1.

In general formula (A-I) and general formula (I), Z represents —O— or —NH—. If n is 2 or larger, plural Z may be identical or different.

In general formula (A-I), Ar represents aromatic ring group or heteroaromatic ring group. The aromatic ring group and heteroaromatic ring group may be a single ring or a plurality of rings, such as fused ring. Examples of an aromatic ring constituting the aromatic ring group include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring; and benzene ring is preferred. As a heteroaromatic ring constituting the heteroaromatic ring group, preference is given to a heteroaromatic ring group having 5-membered ring and/or 6-membered ring. In addition, preference is given to a heteroaromatic ring group containing one or more atoms selected from the group consisting of nitrogen atom, oxygen atom and sulfur atom, as ring member atom(s), more preferably a heteroaromatic ring group containing one or two nitrogen atoms, further preferably a heteroaromatic ring group having a 5-membered ring containing one or two nitrogen atoms or a 6-membered ring containing one or two nitrogen atoms. Examples of a heteroaromatic ring constituting the heteroaromatic ring group include pyridine ring, pyrazine ring, triazine ring, pyridazine ring, pyrimidine ring, pyrrole ring, imidazole ring, furan ring, thiophene ring, indole ring, coumarin ring, quinoline ring, oxazole ring, pyrazole ring, triazole ring, tetrazole ring, thiazole ring, isoxazole ring and the like.

The bonding position to a group adjacent to Ar is not limited. For example, when m is 2 or more, the positions where the plural Y bond to Ar are arbitrary. When Ar is a heteroaromatic ring group containing atom(s) other than carbon atoms such as a nitrogen atom, the bonding position to an adjacent group may be on a carbon atom or an atom other than carbon atoms among the atoms constituting ring Ar.

In formula (A-I), Y represents —OR, —SR, nitro group, amino group or halogen atom.

In general formula (A-I) and general formula (I), R represents hydrogen atom, alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$). Herein, if m is 2 or more, plural R groups that are present may be identical to or different from each other.

In general formula (A-I) and general formula (I), $R^2$ to $R^{11}$, independently of one another, represent hydrogen atom, hydroxy, alkyl, cycloalkyl, alkenyl, alkynyl, aralkyl, aryl, heteroaryl, alkoxy, aryloxy or amino. Herein, among $R^2$ to $R^{11}$, two adjacent groups may be bonded together to form a ring.

In formula (A-I), when Y represents halogen atom, examples of halogen atom include fluorine atom, chlorine atom, bromine atom and iodine atom, and preference is given to fluorine atom.

In formula (A-I), when Y represents amino, the amino is —$NH_2$, or a group in which at least one of hydrogen atoms of —$NH_2$ may be replaced by alkyl, alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$). Herein, $R^2$ to $R^{11}$ have the same meaning as defined in formula (A-I) for $R^2$ to $R^{11}$. Among these, Y is preferably —$NH_2$.

In the present invention, alkyl group may be a linear chain or a branched chain, and examples thereof include alkyl groups having 1 to 3 carbon atoms, such as methyl, ethyl, propyl and isopropyl. When R represents an alkyl group, it is preferably methyl or ethyl.

In the present invention, examples of cycloalkyl include cycloalkyl groups having 3 to 6 carbon atoms such as cyclopropyl, cyclobutyl, cyclopentyl and cyclohexyl.

In the present invention, examples of alkenyl include alkenyl groups having 2 to 5 carbon atoms, such as vinyl, allyl, 1-propenyl, isopropenyl, 3-butenyl, 1-methyl-1-propenyl, 1-methyl-2-propenyl, 2-methyl-2-propenyl, 1-butenyl, 2-butenyl (crotyl group), 3-methyl-2-butenyl (prenyl group). When a geometric isomer exists, the isomer is also included.

In the present invention, examples of alkynyl include alkynyl groups having 1 to 4 carbon atoms, such as ethynyl, propargyl, 2-butynyl, 3-butynyl, 1-methyl-2-propynyl.

In the present invention, alkoxy group (alkyloxy group) has preferably 1 to 5 carbon atoms, and examples thereof include methoxy, ethoxy, propoxy, isopropoxy and butoxy.

In the present invention, alkenyloxy group has preferably 2 to 5 carbon atoms, and examples thereof include allyloxy, crotyloxy and prenyloxy.

In the present invention, alkynyloxy group has preferably 2 to 4 carbon atoms, and examples thereof include ethynyloxy, propargyloxy, 2-butynyloxy, 3-butynyloxy and 1-methyl-2-propynyloxy.

In the present invention, examples of aralkyl include benzyl, α-methylbenzyl, α,α-dimethylbenzyl and phenylethyl. When R represents an aralkyl group, it is preferably benzyl. Herein, any hydrogen atom on phenyl group constituting the aralkyl group may be replaced by halogen atom, alkyl having 1 to 3 carbon atoms, hydroxy or alkoxy.

In the present invention, examples of aralkyloxy include benzyloxy, α-methylbenzyloxy, α,α-dimethylbenzyloxy and phenylethyloxy.

In the present invention, examples of aryl include aryl groups having 6 to 10 carbon atoms, such as phenyl and naphthyl. Herein, any hydrogen atom on the aryl may be replaced by halogen atom, alkyl having 1 to 5 carbon atoms, alkenyl having 1 to 5 carbon atoms, hydroxy or alkoxy.

In the present invention, examples of heteroaryl include nitrogen-containing heteroaryl groups, such as pyridyl, pyrimidinyl, pyrazinyl and quinolinyl. Herein, any hydrogen atom on the heteroaryl may be replaced by halogen atom, alkyl having 1 to 5 carbon atoms, alkenyl having 1 to 5 carbon atoms, hydroxy or alkoxy.

In the present invention, examples of aryl group in aryloxy group include phenyl group and naphthyl. Herein, any hydrogen atom on the aryl may be replaced by halogen atom, alkyl having 1 to 5 carbon atoms, alkenyl having 1 to 5 carbon atoms, hydroxy or alkoxy.

In the present invention, as amino group, at least one of hydrogen atoms of —$NH_2$ may be replaced by alkenyl, alkynyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$($R^9$), or —P(=O)($R^{10}$)($R^{11}$). Herein, $R^2$ to $R^{11}$ have the same meaning as defined in formula (A-I) for $R^2$ to $R^{11}$. As amino group, preference is given to —$NH_2$ or groups in which hydrogen atom(s) of —$NH_2$ is replaced by alkyl and the like, and particularly —$NH_2$, dimethylamino, diethylamino and the like.

In the present invention, examples of acyl include acyl groups having 1 to 8 carbon atoms, such as formyl, acetyl, propionyl, butyryl, pivaloyl, benzoyl, ethoxycarbonyl, t-butoxycarbonyl and benzyloxycarbonyl.

In general formula (A-I) and general formula (I), $R^2$ and $R^3$ in —C(=O)N($R^2$)($R^3$), independently of each other, are preferably, hydrogen atom, alkyl (preferably alkyl having 1 to 4 carbon atoms, more preferably alkyl having 1 to 2 carbon atoms), cycloalkyl (preferably cycloalkyl having 3 to 6 carbon atoms), aralkyl (preferably benzyl), alkenyl (preferably alkenyl having 2 to 3 carbon atoms), alkynyl (preferably alkynyl having 2 to 3 carbon atoms) or aryl (preferably phenyl, tolyl, xylyl or mesityl). Among $R^2$ and $R^3$ constituting one —R, at least one of them is more preferably hydrogen atom. Examples of —C(=O)N($R^2$)($R^3$) include substituted carbamoyl groups having 1 to 10 carbon atoms, such as carbamoyl, methylcarbamoyl, ethylcarbamoyl, propylcarbamoyl, isopropylcarbamoyl, tert-butylcarbamoyl, cyclopropylcarbamoyl, cyclo-butylcarbamoyl, cyclopentylcarbamoyl, cyclohexylcarbamoyl, benzylcarbamoyl, vinyl carbamoyl, allyl carbamoyl, propargyl carbamoyl, phenylcarbamoyl, tolyl carbamoyl, xylyl carbamoyl, mesityl carbamoyl, dimethylcarbamoyl and diethylcarbamoyl.

In general formula (A-I) and general formula (I), $R^4$, $R^5$ and $R^6$, in —Si($R^4$)($R^5$)($R^6$), independently of one another, are preferably optionally substituted alkyl (preferably alkyl having 1 to 4 carbon atoms), aryl (preferably phenyl), or alkoxy (preferably alkoxy having 1 to 4 carbon atoms, more preferably 1 to 2 carbon atoms). Among $R^4$, $R^5$ and $R^6$ constituting one —R, at least two of them are preferably the same substituent groups, and more preferably all of them are the same substituent groups. Examples of —Si($R^4$)($R^5$)($R^6$) include substituted silyl groups having 3 to 18 carbon atoms, such as trimethylsilyl, triethylsilyl, triisopropylsilyl, tripropylsilyl, triphenylsilyl, tert-butyldimethylsilyl, trimethoxysilyl and triethoxysilyl.

In general formula (A-I) and general formula (I), $R^7$ and $R^8$ in —B($R^7$)($R^8$), independently of each other, are preferably hydroxy, alkyl (preferably alkyl having 1 to 3 carbon atoms, more preferably 1 to 2 carbon atoms), alkoxy (preferably alkoxy having 1 to 4 carbon atoms, more preferably 1 to 2 carbon atoms), aryl (preferably phenyl, tolyl or mesityl), or aryloxy. In addition, $R^7$ and $R^8$ may be bonded together to form a ring with boron atom. $R^7$ and $R^8$ constituting one —R are preferably the same substituent groups. Examples of —B($R^7$)($R^8$) include substituted boryl groups having 0 to 14 carbon atoms, such as dihydroxy boryl, ethylenedioxy boryl, dimethoxy boryl, diethoxy boryl, diphenoxy boryl, dimethyl boryl, diethyl boryl, diphenyl boryl, ditolyl boryl and dimesityl boryl.

In general formula (A-I) and general formula (I), $R^9$ in —S(=O)$_2$($R^8$) is preferably hydroxy, alkyl (preferably alkyl having 1 to 3 carbon atoms), aryl (preferably phenyl or tolyl), alkoxy (preferably alkoxy having 1 to 3 carbon atoms), aryloxy (preferably phenoxy) or amino (preferably —NH$_2$ or dimethyl amino). Examples of —S(=O)$_2$($R^9$) include unsubstituted sulfonyl or substituted sulfonyl having 1 to 6 carbon atoms, such as sulfo (—SO$_3$H), methanesulfonyl, ethanesulfonyl, benzenesulfonyl, toluenesulfonyl, methoxysulfonyl, ethoxysulfonyl, phenoxy sulfonyl, sulfonamide (—SO$_2$NH$_2$) and N,N-dimethyl-sulfonamide.

In general formula (A-I) and general formula (I), $R^{10}$ and $R^{11}$ in —P(=O)($R^{10}$)($R^{11}$), independently of each other, are preferably, hydroxy, alkyl (preferably alkyl having 1 to 3 carbon atoms), aryl (preferably phenyl or tolyl), aralkyl (preferably benzyl), alkoxy (preferably alkoxy having 1 to 2 carbon atoms), or amino (preferably —NH$_2$, dimethylamino or diethylamino). $R^{10}$ and $R^{11}$ constituting one —R are preferably the same. Examples of —P(=O)($R^{10}$)($R^{11}$) include unsubstituted phosphate group or substituted phosphate groups having 1 to 14 carbon atoms, such as phosphate group (—P(=O)(OH)$_2$), dimethylphosphoryl, diethylphosphoryl, dipropylphosphoryl, diphenylphosphorylazide, ditolylphosphoryl, dibenzylphosphoryl, dimethoxyphosphoryl, diethoxyphosphoryl, diphenylphosphorylazide, diamide phosphoryl, bis(dimethylamide)phosphoryl and bis(diethylamide)phosphoryl.

In general formula (A-I) and general formula (I), adjacent substituent groups among $R^2$ to $R^{11}$ may be bonded together to form a ring, wherein thus formed ring may optionally have substituent group(s). It is preferred that the substituent groups constituting one —R are forming a ring together. When two adjacent groups among $R^2$ to $R^{11}$ are bonded together to form a ring, the two substituent groups together become a divalent group, for example, alkylene (preferably those having 1 to 6 carbon atoms), alkenylene (preferably those having 2 to 8 carbon atoms), alkynylene (preferably those having 2 to 8 carbon atoms), dioxyalkylene and the like. Specifically, they preferably form methylene, ethylene, methylenedioxy or ethylenedioxy.

In formula (A-I), when m and/or n is 2 or more, plural Y groups are independent to one another, and adjacent Y groups may be bonded together to form a ring. In formula (I), when m and/or n is 2 or more, plural R groups are independent to one another, and adjacent R groups may be bonded together to form a ring.

In formula (A-I), when m and/or n is 2 or more, adjacent Y groups may be bonded together to form a ring, wherein the ring may optionally have a side chain. It is preferred that a ring is formed by 2 Y groups bonding to one Ar, and ring-constituting atoms in aromatic ring group or heteroaromatic ring group in Ar to which 2 Y groups are bonded. Preference is given to an embodiment where adjacent Y groups are, independently of one another, —OR, —SR or amino group, and R in —OR, R in —SR or substituent group bonded to amino group are bonded together to form a ring. Herein, two adjacent groups (R in —OR, R in —SR or substituent group bonded to amino group) together preferably form a divalent group, for example, alkylene (preferably those having 1 to 6 carbon atoms), alkenylene (preferably those having 2 to 8 carbon atoms), alkynylene (preferably those having 2 to 8 carbon atoms), cycloalkylene group (preferably those having 6 to 12 carbon atoms) and the like. Among these, they preferably form methylene or ethylene. More preferably, two adjacent —R are bonded, whereby a ring is formed by 2 —OR groups and ring-constituting atoms in aromatic ring group or heteroaromatic ring group in Ar to which 2 —OR groups are bonded. A ring formed herein preferably has a moiety, such as methylenedioxy, ethylidenedioxy, isopropylidenedioxy, cyclopentylidenedioxy, or cyclohexylidenedioxy, and more preferably it forms methylenedioxy ring, ethylenedioxy ring, vinylenedioxy ring, phenylenedioxy ring, naphthalenedioxy ring.

In formula (I), when m is 2 or more, adjacent R groups may be bonded together to form a ring, wherein the ring may optionally have a side chain. When adjacent R groups form a ring, two adjacent —R together preferably form a divalent group, for example, alkylene (preferably those having 1 to 6 carbon atoms), alkenylene (preferably those having 2 to 8 carbon atoms), alkynylene (preferably those having 2 to 8 carbon atoms), cycloalkylene group (preferably those having 6 to 12 carbon atoms) and the like. Among these, they preferably form methylene or ethylene. More preferably, two adjacent —R are bonded, whereby a ring is formed by 2 —OR groups and ring-constituting atoms in benzene ring to which 2 —OR groups are bonded. A ring formed herein preferably has a moiety, such as methylenedioxy, ethylidenedioxy, isopropylidenedioxy, cyclopentylidenedioxy, or cyclohexylidenedioxy, and more preferably it forms methylenedioxy ring, ethylenedioxy ring, vinylenedioxy ring, phenylenedioxy ring, naphthalenedioxy ring.

In the present invention, in general formula (A-I) and general formula (I), R represents hydrogen atom, methyl, optionally substituted allyl, optionally substituted benzyl group, optionally substituted acetyl, optionally substituted benzoyl, or adjacent R are bonded together to form methylenedioxy.

Furthermore, in general formula (A-I) and general formula (I), any of hydrogen atoms on a benzene ring having pentafluorosulfanyl group may be optionally substituted with at least one substituent selected from the group consisting of alkyl, alkenyl, alkynyl, alkoxy, halogen atom, hydroxyl, nitro and amino. Preferred examples of alkyl include alkyl groups having 1 to 3 carbon atoms, such as methyl, ethyl, propyl and isopropyl. Preferred examples of alkenyl include alkenyl groups having 2 to 5 carbon atoms, such as vinyl, allyl, 1-propenyl, isopropenyl, 3-butenyl, 1-methyl-1-propenyl, 1-methyl-2-propenyl, 2-methyl-2-propenyl, 1-butenyl, 2-butenyl (crotyl group), 3-methyl-2-butenyl (prenyl group). When a geometric isomer exists, the isomer is also included. Preferred examples of alkynyl include alkynyl groups having 1 to 4 carbon atoms, such as ethynyl, propargyl, 2-butynyl, 3-butynyl, 1-methyl-2-propynyl. Preferred examples of alkoxy include alkoxy groups having 1 to 3 carbon atoms, such as methoxy, ethoxy and propoxy. In addition, examples of halogen atom include fluorine atom, chlorine atom, bromine atom and iodine atom.

As specific examples of compound represented by formula (A-I) or formula (I), the following Compounds 1 to 99 can be exemplified. All of Compounds 1 to 99 are novel compounds.

Compound 1: 4-benzoylaminopentafluorosulfanylbenzene
Compound 2: 4-(3,4,5-tribenzyloxybenzoylamino)pentafluorosulfanylbenzene
Compound 3: 4-(3,4,5-trihydroxybenzoylamino)pentafluorosulfanylbenzene
Compound 4: 4-(3,4-diacetoxycinnamoylamino)pentafluorosulfanylbenzene
Compound 5: 4-(3,4-dihydroxycinnamoylamino)pentafluorosulfanylbenzene
Compound 6: 4-(3,4,5-tribenzyloxybenzoyloxy)pentafluorosulfanylbenzene
Compound 7: 4-(3,4,5-trihydroxybenzoyloxy)pentafluorosulfanylbenzene
Compound 8: 3-(3,4,5-trihydroxybenzoyloxy) pentafluorosulfanylbenzene
Compound 9: 4-(3,4,5-triacetoxybenzoylamino)pentafluorosulfanylbenzene
Compound 10: 3-(3,4,5-tribenzyloxybenzoylamino)pentafluorosulfanylbenzene
Compound 11: 3-(3,4,5-trihydroxybenzoylamino)pentafluorosulfanylbenzene
Compound 12: 3-(3,4,5-trihydroxybenzoylamino)-4-hydroxypentafluorosulfanylbenzene
Compound 13: 3,4-bis(3,4,5-tribenzyloxybenzoylamino)pentafluorosulfanylbenzene
Compound 14: 3,4-bis(3,4,5-trihydroxybenzoylamino)pentafluorosulfanylbenzene
Compound 15: 4-hydroxy-3,5-bis(3,4,5-tribenzyloxybenzoylamino)pentafluorosulfanylbenzene
Compound 16: 4-hydroxy-3,5-bis(3,4,5-trihydroxybenzoylamino)pentafluorosulfanylbenzene
Compound 17: 4-(3,4,5-tribenzyloxybenzoylamino)-3-(3,4,5-tribenzyloxybenzoyloxy)pentafluorosulfanylbenzene
Compound 18: 4-(3,4,5-trihydroxybenzoylamino)-3-(3,4,5-trihydroxybenzoyloxy)pentafluorosulfanylbenzene
Compound 19: 4-(3,4-methylenedioxycinnamoylamino)pentafluorosulfanylbenzene
Compound 20: 4-(4-acetoxy-3-methoxycinnamoylamino)pentafluorosulfanylbenzene
Compound 21: 4-(4-hydroxy-3-methoxycinnamoylamino)pentafluorosulfanylbenzene
Compound 22: 4-(3,4-diacetoxycinnamoyloxy)pentafluorosulfanylbenzene
Compound 23: 4-(2,4,6-trihydroxybenzoylamino)pentafluorosulfanylbenzene
Compound 24: 4-(3,4,5-trihydroxycinnamoylamino)pentafluorosulfanylbenzene
Compound 25: 4-(3,4,5-triacetoxycinnamoylamino)pentafluorosulfanylbenzene
Compound 26: 4-(3,5-bis(3-methyl-2-butenyloxy)benzoylamino)pentafluorosulfanylbenzene
Compound 27: 4-(4-(3-methyl-2-butenyloxy)-3-methoxybenzoylamino)pentafluorosulfanylbenzene
Compound 28: 4-(4-(2-propenyloxy)-3-methoxybenzoylamino)pentafluorosulfanylbenzene
Compound 29: 4-(2,3,4-tris(3-methyl-2-butenyloxy)benzoylamino)pentafluorosulfanylbenzene
Compound 30: 4-(4-hydroxy-5-(2-propenyl)-3-methoxybenzoylamino)pentafluorosulfanylbenzene
Compound 31: 4-acryloylaminopentafluorosulfanylbenzene
Compound 32: 3-acryloylaminopentafluorosulfanylbenzene
Compound 33: 4-(5-hydroxymethylfuran-2-yl)carbonylaminopentafluorosulfanylbenzene
Compound 34: 4-(4-(3-methyl-2-butenyloxy)-3-methoxybenzoyloxy)pentafluorosulfanylbenzene
Compound 35: 4-(cinnamoylamino)pentafluorosulfanylbenzene
Compound 36: 4-(cinnamoyloxy)pentafluorosulfanylbenzene
Compound 37: 4-(4-(3-methyl-2-butenyloxy)-3-methoxycinnamoylamino)pentafluorosulfanylbenzene
Compound 38: 4-(4-(2-propenyloxy)-3-methoxycinnamoylamino)pentafluorosulfanylbenzene
Compound 39: 4-(3,4-bis(3-methyl-2-butenyloxy)cinnamoylamino)pentafluorosulfanylbenzene
Compound 40: 4-(2,4-bis(3-methyl-2-butenyloxy)cinnamoylamino)pentafluorosulfanylbenzene
Compound 41: 4-(3-(3-methyl-2-butenyloxy)-4-methoxycinnamoylamino)pentafluorosulfanylbenzene
Compound 42: 4-(4-(2-butenyloxy)-3-methoxycinnamoylamino)pentafluorosulfanylbenzene
Compound 43: 4-(4-(3-methyl-2-butenyloxy)-3,5-dimethoxycinnamoylamino)pentafluorosulfanylbenzene
Compound 44: 4-(4-(1-methyl-2-propenyloxy)-3-methoxycinnamoylamino)pentafluorosulfanylbenzene
Compound 45: 4-(4-hydroxy-3-methoxybenzoylamino)pentafluorosulfanylbenzene
Compound 46: 4-(4-hydroxy-5-(2-propenyl)-3-methoxycinnamoylamino)pentafluorosulfanylbenzene
Compound 47: 4-(4-hydroxy-5-(2-butenyl)-3-methoxycinnamoylamino)pentafluorosulfanylbenzene
Compound 48: 4-(3-(1, 1-dimethyl-2-propenyloxy)benzoylamino)pentafluorosulfanylbenzene
Compound 49: 4-(2,3,4-trihydroxybenzoylamino)pentafluorosulfanylbenzene
Compound 50: 4-(3,5-dihydroxybenzoylamino)pentafluorosulfanylbenzene
Compound 51: 4-(2,4-dihydroxycinnamoylamino)pentafluorosulfanylbenzene
Compound 52: 4-(3-hydroxy-4-methoxycinnamoylamino)pentafluorosulfanylbenzene
Compound 53: 4-(4-hydroxy-3,5-dimethoxycinnamoylamino)pentafluorosulfanylbenzene
Compound 54: 4-(2,3,4-tripropenyloxybenzoylamino)pentafluorosulfanylbenzene
Compound 55: 4-(2,4,6-trihydroxybenzoylamino)pentafluorosulfanylbenzene Compound 56: 4-(3,4-dihydroxycinnamoylamino)pentafluorosulfanylbenzene
Compound 57: 4-(4-hydroxy-3-fluorobenzoylamino)pentafluorosulfanylbenzene
Compound 58: 4-(3-hydroxy-4-fluorobenzoylamino)pentafluorosulfanylbenzene
Compound 59: 4-(4-nitro-3-methoxybenzoylamino)pentafluorosulfanylbenzene
Compound 60: 4-(4-amino-3-methoxybenzoylamino)pentafluorosulfanylbenzene
Compound 61: 4-(4-aminobenzoylamino)pentafluorosulfanylbenzene
Compound 62: 4-(4-nitrobenzoylamino)pentafluorosulfanylbenzene
Compound 63: 4-(4-aminobenzoylamino)pentafluorosulfanylbenzene hydrochloride salt
Compound 64: 4-(3-allyloxybenzoylamino)pentafluorosulfanylbenzene
Compound 65: 4-(3-hydroxybenzoylamino)pentafluorosulfanylbenzene
Compound 66: 4-(2-hydroxypyridin-6-yl)carbonylaminopentafluorosulfanylbenzene
Compound 67: 4-(2-hydroxypyridin-3-yl)carbonylaminopentafluorosulfanylbenzene
Compound 68: 4-(3-hydroxypyridin-2-yl)carbonylaminopentafluorosulfanylbenzene
Compound 69: 4-(4-hydroxypyrimidin-6-yl)carbonylaminopentafluorosulfanylbenzene
Compound 70: 4-(pyrimidin-2-yl)carbonylaminopentafluorosulfanylbenzene
Compound 71: 4-(pyridin-2-yl)carbonylaminopentafluorosulfanylbenzene
Compound 72: 4-(pyridin-4-yl)carbonylaminopentafluorosulfanylbenzene
Compound 73: 4-(pyrimidin-4-yl)carbonylaminopentafluorosulfanylbenzene
Compound 74: 4-(6,7-dihydroxycoumarin-3-yl)carbonylaminopentafluorosulfanylbenzene
Compound 75: 4-(3-fluoropyridin-4-yl)carbonylaminopentafluorosulfanylbenzene
Compound 76: 4-(2-fluoropyridin-4-yl)carbonylaminopentafluorosulfanylbenzene
Compound 77: 4-(5-fluoroindol-2-yl)carbonylaminopentafluorosulfanylbenzene
Compound 78: 4-(imidazol-2-yl)carbonylaminopentafluorosulfanylbenzene
Compound 79: 4-(pyrazin-2-yl)carbonylaminopentafluorosulfanylbenzene
Compound 80: 4-(pyrrol-1-yl)carbonylaminopentafluorosulfanylbenzene
Compound 81: 4-(oxazol-4-yl)carbonylaminopentafluorosulfanylbenzene
Compound 82: 4-(oxazol-5-yl)carbonylaminopentafluorosulfanylbenzene
Compound 83: 4-(pyrrol-2-yl)carbonylaminopentafluorosulfanylbenzene
Compound 84: 4-(pyrazol-1-yl)carbonylaminopentafluorosulfanylbenzene
Compound 85: 4-(pyrrol-3-yl)carbonylaminopentafluorosulfanylbenzene
Compound 86: 4-(pyrazol-3-yl)carbonylaminopentafluorosulfanylbenzene
Compound 87: 4-(furan-2-yl)carbonylaminopentafluorosulfanylbenzene
Compound 88: 4-(thiophen-2-yl)carbonylaminopentafluorosulfanylbenzene
Compound 89: 4-(furan-3-yl)carbonylaminopentafluorosulfanylbenzene
Compound 90: 4-(thiophen-3-yl)carbonylaminopentafluorosulfanylbenzene
Compound 91: 4-(3-hydroxypyridazin-6-yl)carbonylaminopentafluorosulfanylbenzene
Compound 92: 4-(2-bromothiazol-5-yl)carbonylaminopentafluorosulfanylbenzene
Compound 93: 4-(2-allyl-3-hydroxybenzoylamino)pentafluorosulfanylbenzene
Compound 94: 4-(4-allyl-3-hydroxybenzoylamino)pentafluorosulfanylbenzene
Compound 95: 4-(2,4,6-tris(3-methyl-2-butenyloxy)benzoylamino)pentafluorosulfanylbenzene
Compound 96: 4-(4-(1,1-dimethyl-2-propenyloxy)-3-fluorobenzoylamino)pentafluorosulfanylbenzene
Compound 97: 4-(4-hydroxy-3-fluoro-5-(3-methyl-2-butenyl)benzoylamino)pentafluorosulfanylbenzene
Compound 98: 4-(4-(1,1-dimethyl-2-propenyloxy)-3-fluoro-cinnamoylamino)pentafluorosulfanylbenzene
Compound 99: 4-(4-hydroxy-3-fluoro-5-(3-methyl-2-butenyl)cinnamoylamino)pentafluorosulfanylbenzene As described below, Compound (A-I) of the present invention is obtained by reacting, in the presence of a base, a pentafluorosulfanylbenzene compound represented by formula (A-II) (hereinafter, may be referred to as Compound (A-II)) with a benzoic acid compound or a cinnamic acid compound represented by formula (A-III) (hereinafter, may be referred to as Compound (A-III)) (Reaction A).

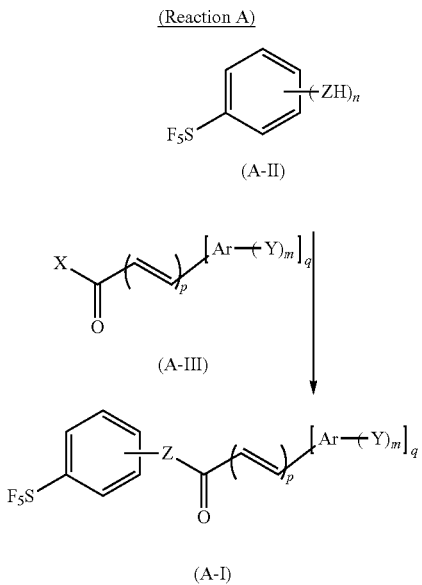

As described below, Compound (I) of the present invention is obtained by reacting, in the presence of a base, a pentafluorosulfanylbenzene compound represented by general formula (II) (hereinafter, may be referred to as Compound (II)) with a benzoic acid compound or a cinnamic acid compound represented by formula (III) (hereinafter, may be referred to as Compound (III)) (Reaction A').

(Reaction A')

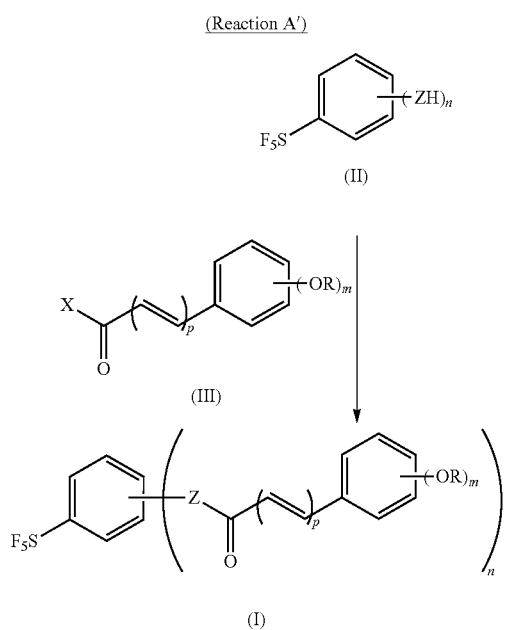

In the formula (A-II), Z and n, each, represent the meanings defined in Formula (A-I), and in the formula (II), Z and n, respectively, represent the meanings defined in Formula (I). Herein, in formula (A-II) and formula (II), any of hydrogen atoms on carbons of a benzene ring may be optionally substituted with at least one substituent selected from the group consisting of alkyl, alkenyl, alkynyl, alkoxy, halogen atom, hydroxyl, nitro and amino.

In the formula (A-III), m, p, q, Ar and Y, each, represent the meanings as defined for formula (A-I), and in the formula (III), m, p, and R, each, represent the meanings as defined for formula (I). Examples of X include halogen atom, hydroxy, optionally substituted nitrophenoxy, optionally substituted nitro benzoyloxy, azide group (—$N_3$), pivaloyloxy, 1-imidazolyl, 1-triazolyl, 1-tetrazolyl, and the like. While it is appropriately selected depending on the stability of Compound (A-III) or Compound (III), it is preferably chlorine atom or hydroxy. As for the substituent group of substituted nitrophenoxy and substituted nitro benzoyloxy, the examples thereof include halogen atom, alkyl having 1 to 4 carbon atoms, amino group optionally substituted with two alkyl groups having 1 to 3 carbon atoms. In addition, if R in formula (A-III) (in case Y is —OR) or R in formula (III) represents a stable substituent under basic conditions such as alkyl, alkenyl, alkynyl or aralkyl, X may be also alkyloxy, alkenyloxy, alkynyloxy or aralkyloxy.

In the reaction, a base (basic compound) that can be used is one that inactivates the acidic compound produced in the reaction. The examples thereof include triethylamine, ethyldiisopropylamine, 4-dimethylaminopyridine (DMAP), pyridine, 2,6-lutidine and the like. These basic compounds may be used alone or in a combination of two or more. While the use amount of the basic compound is not limited, it is preferably 0.8 to 5 equivalents relative to Compound (A-III) or Compound (III). In addition, if R is a stable substituent under basic conditions such as alkyl, alkenyl, alkynyl or aralkyl, the base that can be used includes alkali metal alkoxides, such as alkali metal methoxide, alkali metal ethoxide, alkali metal tert-butoxide, alkali metal tert-pentoxide and the like, metal hydrides, such as sodium hydride, potassium hydride and the like, and alkyllithium compounds such as butyl lithium, tert-butyl lithium and the like.

In addition, in the above reaction, if X is OH, generally a dehydration condensing agent is used. The examples of the dehydration condensing agent include dicyclohexylcarbodiimide (DCC), carbonyldiimidazole (CDI), diphenylphosphoryl azide (DPPA), 1-ethyl-3-(3-dimethylaminopropyl)carbodiimide (known under the name of EDC or WSCI), substituted nitrobenzoic acid anhydride, 2-chloro-4,6-dimethoxy-1,3,5-triazine (DMT) or a mixture of DMT and N-methylmorpholine (DMT-MM) and the like. The dehydration condensing agent is appropriately selected depending on the solvent suitable for the reaction. Herein, in this condensation reaction, the addition of the above-mentioned base (basic compound) sometimes improves the reaction performance.

In the above reaction A, while the reaction conditions can be adjusted as appropriate, Compound (A-I) may be obtained, for example, by mixing Compound (A-II) and Compound (A-III) in the mole ratio of (1:5 to 5:1), and reacting them for 0.2 hours to 72 hours at a temperature of −30° C. to 150° C.

In the above reaction A', while the reaction conditions can be adjusted as appropriate, Compound (I) may be obtained, for example, by mixing Compound (II) and Compound (III) in the mole ratio of (1:5 to 5:1), and reacting them for 0.2 hours to 72 hours at a temperature of −30° C. to 150° C.

When Y is hydroxy in formula (A-I), the compound may be produced by a method of either (method 1) or (method 2) as shown in the following scheme.

(Method 1) Method (Reaction B) of obtaining a target compound by reacting, in the presence of a base, pentafluorosulfanylbenzene compound represented by formula (A-II) (hereinafter may be referred to as Compound (A-II)) with a compound represented by formula (A-III') in which a hydroxyl group is protected as —$OR^1$ group (hereinafter, may be referred to as Compound (A-III')), and removing the protection group. Herein, in case that Y is akoxy other than hydroxyl group in Compound (A-III), it is kept unchanged before and after this reaction.

(Method 2) Method (Reaction C) of reacting, in the presence of a base, pentafluorosulfanylbenzene compound represented by formula (A-II) (hereinafter may be referred to as Compound (A-II)) with a compound represented by formula (A-III) in which Y is hydroxy (hereinafter, may be referred to as Compound (A-III")).

(Reaction B and Reaction C)

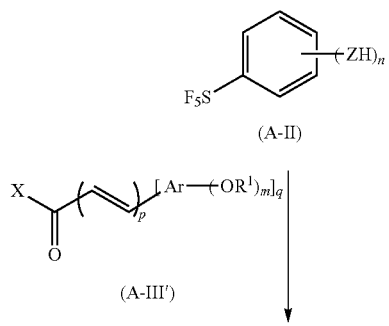

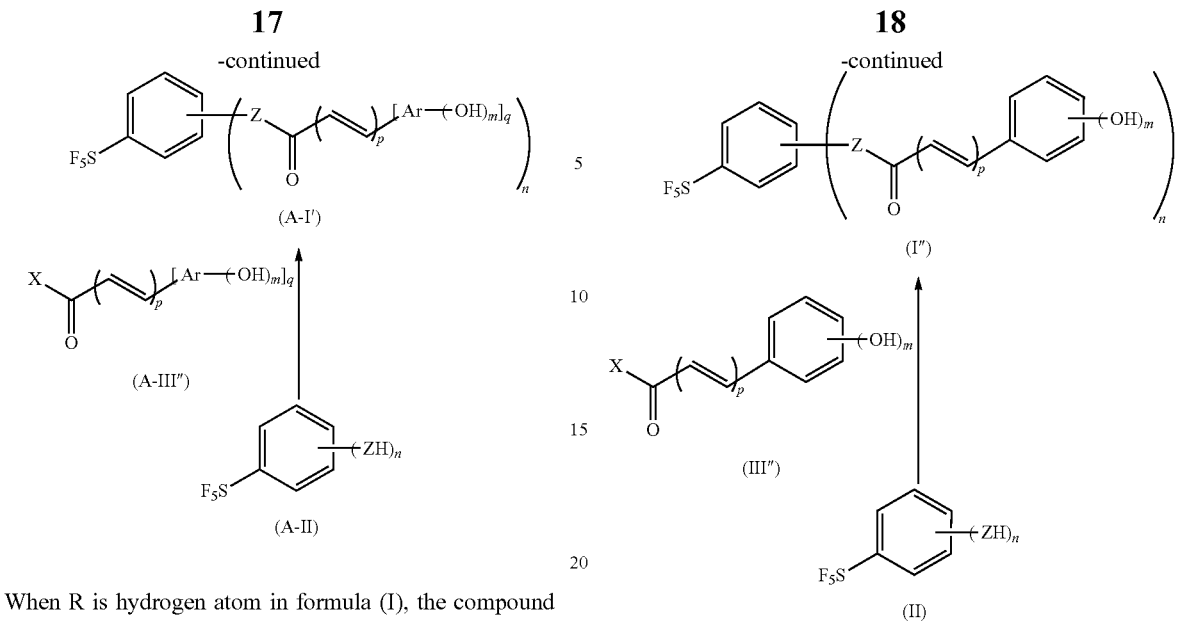

(A-I')

(A-III")

(A-II)

When R is hydrogen atom in formula (I), the compound may be produced by a method of either (method 1') or (method 2') as shown in the following scheme.

(Method 1') Method (Reaction B') of obtaining a target compound by reacting, in the presence of a base, pentafluorosulfanylbenzene compound represented by formula (II) (hereinafter may be referred to as Compound (II)) with a compound represented by formula (III') in which a hydroxyl group is protected as $-OR^1$ group (hereinafter, may be referred to as Compound (III')), and removing the protection group.

(Method 2') Method (Reaction C') of reacting, in the presence of a base, pentafluorosulfanylbenzene compound represented by formula (II) (hereinafter may be referred to as Compound (II)) with a compound represented by formula (III) in which R is hydrogen atom (hereinafter, may be referred to as Compound (III")).

(Reaction B' and Reaction C')

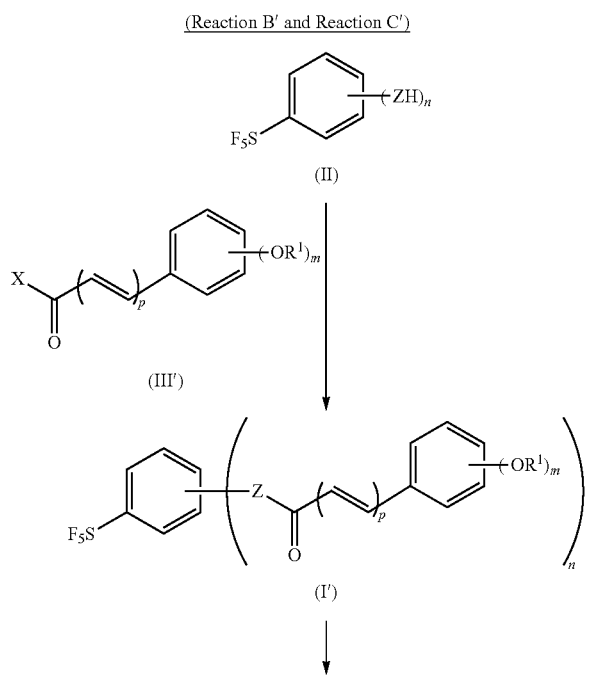

(II)

(III')

(I')

(I")

(III")

(II)

In formula (A-II) of the above-described (Reaction B) and (Reaction C), Z and n, each, represent the meanings defined in Formula (A-I). Herein, in formula (A-II) any of hydrogen atoms on carbons of a benzene ring may be optionally substituted with at least one substituent selected from the group consisting of alkyl, alkenyl, alkynyl, alkoxy, halogen atom, hydroxy, nitro and amino. In formula (A-III') and formula (A-III"), m, p, q and Ar, each, represent the meanings as defined for formula (A-I), X represents the meanings as defined for formula (A-III).

In formula (A-III'), $R^1$ represents the meanings defined for R in formula (A-I) other than hydrogen, and is preferably, for example, benzyl, methoxybenzyl, dimethoxybenzyl, trityl, tetrahydropyranyl, methoxymethyl, methoxyethoxymethyl, allyl, crotyl, prenyl, acetyl, pivaloyl, benzoyl, triethylsilyl, tert-butyldimethylsilyl or triisopropylsilyl.

In formula (A-I'), p, m, n, Ar and Z, each, represent the meanings as defined for formula (A-I).

In formula (II) of the above-described (Reaction B') and (Reaction C'), Z and n, each, represent the meanings defined in Formula (I). Herein, in formula (II) any of hydrogen atoms on carbons of a benzene ring may be optionally substituted with at least one substituent selected from the group consisting of alkyl, alkenyl, alkynyl, alkoxy, halogen atom, hydroxy, nitro and amino. In formula (III') and formula (III"), m and p, each, represent the meanings as defined for formula (I), X represents the meanings as defined for formula (III). In formula (III'), $R^1$ represents the meanings defined for R in formula (I) other than hydrogen, and is preferably, for example, benzyl, methoxybenzyl, dimethoxybenzyl, trityl, tetrahydropyranyl, methoxymethyl, methoxyethoxymethyl, allyl, crotyl, prenyl, acetyl, pivaloyl, benzoyl, triethylsilyl, tert-butyldimethylsilyl or triisopropylsilyl. In formula (I') and formula (I"), p, m, n and Z, each, represent the meanings as defined for formula (I) and $R^1$ represents the meanings as defined in formula (III').

The above reactions (A), (B), (C), (A'), (B') and (C') may be carried out without solvent or in the presence of a solvent. When a solvent is used, the solvent is not particularly limited, but the examples thereof include methylene chloride, methanol, chloroform, dimethoxymethane, tetrahydrofuran (THF), 2-methyltetrahydrofuran (MTHF), pyridine, water, toluene, dimethylformamide (DMF), dimethyl sulfoxide (DMSO), acetonitrile, N-methylpyrrolidone (NMP) and the mixed solvent of two or more of these.

The compounds represented by general formula (A-I) or general formula (I) may form pharmaceutically acceptable salts depending on the choice of a substituent group. The pharmaceutically acceptable salts are not particularly limited, but are preferably those less toxic and water-soluble. The examples of suitable salts include salts of alkali metals (potassium, sodium, lithium, etc.), the salts of alkaline earth metals (calcium, magnesium etc.), ammonium salts (tetramethylammonium salt, tetrabutylammonium salt, etc.), salts of pharmaceutically acceptable organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.) and the like. Or, salts of pharmaceutically acceptable acids, and the examples thereof include halides, in particular hydrochlorides, lactates, sulfates, citrates, tartrates, acetates, phosphates, methanesulfonate, benzenesulfonate, p-toluenesulfonate and the like.

An embodiment of the present invention may be a prodrug of a compound represented by general formula (A-I) or general formula (I). The prodrug refers to a medicinal agent chemically modified such that it is converted into a compound having a pharmacological activity in vivo or after it reaches a target site, and then to exert a pharmacological effect (activated). For example, the prodrug of the present embodiment is converted into a compound represented by general formula (A-I) or formula (I), through a reaction with an enzyme(s) and gastric acid in vivo.

As a prodrug of a compound represented by general formula (A-I) or general formula (I) when the compound represented by general formula (A-I) or formula (I) has, for example, a hydroxyl group, compounds obtained by acylating, alkylating, alkenylating, alkynylating, silylating, phosphorylating and borating the hydroxyl group (e.g., compounds obtained by acetylating, palmitoylating, propanoylating, pivaloylating, succinylating, fumarylating, alanylating and dimethylaminomethylcarbonylating the hydroxyl group of a compound represented by general formula (A-I) or formula (I)), may be mentioned. These compounds may be produced by methods known in the art. The prodrug of a compound represented by general formula (A-I) or general formula (I) may be a solvate or a non-solvate.

It is said that if radiation and anticancer agents are repeatedly used, cells are inflamed to produce active oxygen and the active oxygen damages DNA and produces cancer cells de-novo. Up to the present, although it has been known that an antioxidant has an effect of preventing carcinogenesis, the antioxidative action of the antioxidant is poor. In the context, it has been desired to develop an antioxidant having a strong antioxidative action and low toxicity.

Aryloyl(oxy or amino)pentafluorosulfanylbenzene compound represented by general formula (A-I) or general formula (I) of the present invention has an excellent antimicrobial action, bactericidal action, antiviral action, anticancer action, angiogenesis inhibitory action, antiallergic action, inhibitory action on degranulation from mast cells, cell proliferation inhibitory action, apoptosis-inducing action, gene expression suppressive action, topoisomerase inhibitory action, antioxidative action and anti-inflammatory action. Accordingly, the present invention can provide a novel compound having excellent properties and serving as an antimicrobial agent, a bactericidal agent, a topoisomerase inhibitor, an antiviral agent, an anticancer agent, an angiogenesis inhibitor, a cancer metastasis inhibitor, an antiallergic agent, an antioxidant, an anti-inflammatory agent, an anti-ulcer agent, a periodontal disease therapeutic/prophylactic agent, a caries therapeutic/prophylactic agent or the like. The effects of the compound (A-I) and compound (I) of the present invention as medicinal agents will be described below.

The aryloyl(oxy or amino)pentafluorosulfanylbenzene compound (compound (A-I) and compound (I)) of the present invention has both antimicrobial action and bactericidal action. The "antimicrobial action" herein means an action of inhibiting microbial or fungal growth and proliferation; whereas, the "bactericidal action" means an action of killing bacteria.

A compound (A-I) and compound (I) exhibit antimicrobial activity and bactericidal activity on bacteria or fungi. Examples of the bacteria include, but are not particularly limited to, *Salmonella, Staphylococcus aureus, Escherichia coli, Pseudomonas aeruginosa, Cholera bacillus, Shigella, Bacillus anthracis, Mycobacterium tuberculosis, Clostridium botulinum, Clostridium tetani, Streptococcus, Helicobacter pylori* and oral bacteria such as *Streptococcus mutans* (caries bacteria) and *Porphyromonas gingivalis* (periodontal disease causative bacteria).

Examples of the infection caused by these bacteria include infectious gastroenteritis, enterohemorrhagic *E. coli* (O157) infection, tuberculosis, tetanus, septicemia, otitis externa, otitis media, dental caries and periodontal disease. Examples of the fungi include, but are not particularly limited to, *Trichophyton, Candida* and *Aspergillus*. Examples of the infection caused by these fungi include trichophytosis (foot ringworm), candidiasis and aspergillosis.

The compound (A-I) and compound (I) of the present invention have a prophylactic and/or therapeutic effect on the diseases caused by the aforementioned bacteria or fungi and can be used as an antimicrobial agent and/or a bactericidal agent.

A compound represented by general formula (A-I) and a compound represented by general formula (I) of the present invention can suppress proliferation of cancer cells.

A compound represented by general formula (A-I) and a compound represented by general formula (I) of the present invention have a topoisomerase inhibitory action. DNA topoisomerase is an important enzyme involved in all DNA metabolisms such as DNA replication, transcription and recombination and the topoisomerase inhibitor is used in therapeutic agents for cancer and antimicrobial agents.

The compound (A-I) and compound (I) of the present invention have an apoptosis-inducing action and induce apoptosis of various cancer cells.

Since the compound (A-I) and compound (I) of the present invention have effects such as cancer cell proliferation inhibition, a topoisomerase inhibitory action and apoptosis induction of cancer cells, as mentioned above, they can be used as an anticancer agent in preventing or treating cancer. Examples of cancer that can be prevented or treated by the compound represented by general formula (A-I) and a compound represented by general formula (I) of the present invention include squamous cell cancer, lung cancer, peritoneal cancer, skin cancer, cutaneous or intraocular melanoma, rectal cancer, cancer near the anal, esophageal cancer, small intestine cancer, endocrine cancer, parathyroid cancer, adrenal cancer, soft tissue sarcoma, urethral cancer, chronic leukemia (e.g., chronic myeloid leukemia) or acute leukemia (e.g., acute lymphocytic leukemia, acute myeloid leukemia), lymphocytic lymphoma, liver cancer, stomach cancer, colorectal cancer, pancreatic cancer, glioblastoma, cervical cancer, ovarian cancer, hepatic cancer, bladder cancer, liver tumor, breast cancer, colon cancer, colorectal cancer, endometrial cancer or uterine cancer, salivary gland cancer, kidney cancer, prostate cancer, carcinoma vulvae, thyroid cancer and head and neck cancer.

The compounds (A-I) and compound (I) of the present invention have an angiogenesis inhibitory action. "Angiogenesis" refers to a physiological phenomenon where branch vessels are produced de-novo from existing blood vessels and construct a vascular network. Although angiogenesis is a physiological phenomenon essential for a living body, it is also responsible for developing many diseases called angiogenic diseases. Examples of the angiogenic diseases include not only proliferation/metastasis of a tumor or cancer but also diabetic retinopathy and age-related macular degeneration causing vision loss as well as chronic inflammatory diseases such as psoriasis and rheumatoid arthritis. In these diseases, angiogenesis is a phenomenon essential for supplying nourishment required for proliferation/metastasis of lesional tissues. Conversely to say, if angiogenesis is suppressed by using the compound (A-I) or compound (I) of the present invention, it is considered that the aforementioned diseases can be prevented or treated.

A compound represented by formula (A-I) and a compound represented by formula (I) of the present invention have an antiallergic action (degranulation inhibitory action). If a degranulatory response is suppressed, chemical mediators such as histamine can be confined in mast cells, with the result that allergic symptoms are successfully suppressed. Examples of allergy (allergic disease) include, but are not particularly limited to, diseases known as type I allergic diseases such as urticaria, pollinosis, asthma, PIE syndrome, atopic dermatitis, allergic rhinitis, allergic conjunctivitis, food allergy, drug allergy and anaphylaxis.

A compound represented by formula (A-I) and a compound represented by formula (I) of the present invention have an anti-inflammatory action and can suppress expression of m-RNA of inflammatory mediators (e.g., TNF-$\alpha$, interleukins, chemokines). Accordingly, the compound (A-I) and compound (I) of the present invention can suppress release of inflammatory mediators and can be used as an anti-inflammatory agent.

Since a compound represented by formula (A-I) and a compound represented by formula (I) of the present invention have a virus inactivating action, they can be used as an antiviral agent. Examples of the viruses that can be treated or prevented by the compounds of the present invention include, but are not particularly limited to, herpes virus, influenza virus, feline calicivirus, parainfluenza virus, coronavirus, SARS-associated coronavirus, togavirus, paramyxovirus, orthomyxovirus, rhabdoviruses, bunyaviruses, arenaviruses, retroviruses and baculovirus.

The compound (A-I) and compound (I) of the present invention and pharmaceutically acceptable salts thereof are expected to be used as osteoporosis therapeutic/prophylactic agents, rheumatoid arthritis therapeutic/prophylactic agents, osteoarthritis therapeutic/prophylactic agents, Alzheimer's disease therapeutic agents, diabetes therapeutic/prophylactic agents, arteriosclerosis therapeutic/prophylactic agents, myocardial infarction prophylactic agents, platelet aggregation inhibitors, lipid metabolism improving agents, cholesterol-lowering agents and blood pressure control agents.

The compound (A-I) and compound (I) of the present invention and pharmaceutically acceptable salts thereof induce apoptosis of osteoclastic cells and thereby suppress proliferation of osteoclastic cells. Usually, in the bone, bone formation by osteoblast cells and bone absorption by osteoclastic cells are in equilibrium and bone mass is kept constant by a mutual response mechanism between these cells. However, if the equilibrium is broken by causes such as aging and inflammations, abnormal bone metabolisms such as osteoporosis, rheumatoid arthritis develop. Since compound (A-I) and compound (I) of the present invention and pharmaceutically acceptable salts thereof suppress abnormal proliferation of osteoclastic cells, they can be used for treating or preventing osteoporosis. In addition to the proliferation-inhibitory action of osteoclastic cells, the compounds have an anti-TNF action, they can be used for treating or preventing rheumatoid arthritis.

Since the compound (A-I) and compound (I) of the present invention have an antioxidative action and a suppressive action on m-RNA expression of interleukin, they can be used as an osteoarthritis therapeutic/prophylactic agent.

Since the compound (A-I) and compound (I) of the present invention can suppress production of $\beta$-amyloid and have an antioxidative action, they can be used as an Alzheimer's disease therapeutic agent.

Since the compound (A-I) and compound (I) of the present invention have a suppressive action on m-RNA expression of TNF-$\alpha$, which is known to suppress action of insulin and have an antioxidative action, they can be used as a diabetes therapeutic/prophylactic agent.

Since the compound (A-I) and compound (I) of the present invention have an antioxidative action, they can be used as an arteriosclerosis therapeutic/prophylactic agent and a myocardial infarction prophylactic agent.

Compounds represented by formula (A-I) and a compound represented by formula (I) of the present invention can be administered directly or together with a pharmaceutical carrier generally used, into animals and humans. Dosage form is not particularly limited and appropriately selected as needed. Examples of the dosage form include oral agents such as tablets, capsules, granules, fine granules, powders, mouthwashes, chewing gum formulations, candy formulations, sustained-release formulations, suspensions, emulsions, syrups and elixirs; and parenteral agents such as injections, suppositories, endermic liniments and adhesive patches.

Oral agents are produced by using, for example, starch, lactose, sucrose, mannitol, carboxymethyl cellulose, corn starch, inorganic salts and in accordance with a customary method.

In formulations, other than the excipients, binders, disintegrators, surfactants, lubricants, glidants, taste masking agents, coloring agents and flavoring agents can be used.

Examples of the binding agents include starch, dextrin, gum Arabic powder, gelatin, hydroxypropyl starch, methylcellulose, sodium carboxymethylcellulose, hydroxypropylcellulose, crystalline cellulose, ethyl cellulose, polyvinyl pyrrolidone and macrogol.

Examples of the disintegrators include starch, hydroxypropyl starch, sodium carboxymethylcellulose, calcium carboxymethylcellulose, carboxymethylcellulose and low-substituted hydroxypropylcellulose.

Examples of the surfactants include sodium lauryl sulfate, soybean lecithin, sucrose fatty acid ester and polysorbate 80.

Examples of the lubricants include talc, waxes, hydrogenated vegetable oils, sucrose fatty acid esters, magnesium stearate, calcium stearate, aluminum stearate and polyethylene glycol.

Examples of the glidants include light anhydrous silicic acid, dried aluminum hydroxide gel, synthetic aluminum silicate and magnesium silicate.

An injectable solution is produced in accordance with the customary method and using a general diluent such as distilled water for injection, physiological saline, an aqueous glucose solution, olive oil, sesame oil, peanut oil, soybean oil, corn oil, propylene glycol and polyethylene glycol. In addition, if necessary, a bactericidal agent, an antiseptic agent and a stabilizer may be added. In view of stability, the injectable solution is stored in vials and the like, frozen and subjected to an ordinary freeze-dry technique to remove water content. The freeze-dried agent can be returned to a liquid agent just before use. Further if necessary, an isotonic agent, a stabilizer, an antiseptic agent a soothing agent and the like may be appropriately added.

The other parenteral agents including liquids for external use, endermic liniments such as ointments, patches and suppositories for intrarectal administration, are produced in accordance with the customary method.

Pharmaceutical compositions containing a compound (A-I), compound (I) of the present invention and a pharmaceutically acceptable salt thereof may be administered in the form of aerosol or spray. In this case, each of the compound (A-I), compound (I) and a pharmaceutically acceptable salt thereof may be dissolved in a pharmaceutically acceptable solvent, particularly e.g., ethanol or water or a solution mixture of these to obtain a solution, a suspension or an emulsion. In such a formulation, if necessary, a surfactant, an emulsifier and a stabilizer, and a spray gas are contained. Such a formulation usually contains an active ingredient in a concentration of about 0.1 to 10 wt % and particularly about 0.3 to 3 wt %.

The compound (A-I) and compound (I) of the present invention may be added to foods and drinks. In the present invention, the foods and drinks include common foods and health functional foods. Examples of the common foods include, but are not particularly limited to, grain processed foods, vegetable processed foods, fruit processed foods, meat processed foods, processed marine foods, dairy products, beverages and health foods. Examples of the grain processed foods include, but are not particularly limited to, wheat flour, rice flour, cereal bars, crackers, cubic rice crackers and cookies. Examples of the vegetable processed foods include, but are not particularly limited to, vegetable pastes, dried vegetables and vegetable soups. Examples of the fruit processed foods include, but are not particularly limited to, fruit puree and dried fruits. Examples of the meat processed foods include, but are not particularly limited to, ham, bacon and sausage. Examples of the processed marine foods include, but are not particularly limited to, fish boiled in soy sauce, salted dried fish, fish sausage, hampen (fish minced and steamed), kamaboko (boiled fish paste) and chikuwa. Examples of dairy products include, but are not particularly limited to, milk beverages, yogurts, ice creams and cheeses. Examples of the beverages include, but are not particularly limited to, soft drinks, green teas, red teas and coffees. Other than these, gums and candies are mentioned. The health functional foods, which are also generally called as functional foods, include foods for specified health use and foods with nutrient function claims.

The doses of active ingredients of compound (A-I) and compound (I) to be administered and the administration frequency thereof vary depending upon the activity titer and duration of action of the compounds to be used; the nature and severity of the disease to be treated; and the gender, age, body weight and sensitivity of the animal or human to be treated. If a pharmaceutical composition of the present invention is administered, for example, as an oral agent, to an adult, the compound (A-I) and compound (I) may be taken in an amount of 1 to 500 mg and preferably 1 to 200 mg per day in 1 to 5 doses. Alternatively, if a pharmaceutical composition of the present invention may be administered, for example, as a parenteral agent, to an adult, in an amount of 1 to 50 mg per day in terms of weight of the compound (A-I) and compound (I), by intravenous injection, intravenous infusion, subcutaneous injection and intramuscular injection.

EXAMPLES

Hereinafter, the present invention will be specifically described by way of examples, but the present invention is not limited by the following examples.

<Part A>

Hereinafter, the synthesis of novel compounds will be described.

Example 1 Synthesis of Compound 1

(Z=NH, p=0, m=0, n=1; Synthesis of 4-benzoylamino pentafluorosulfanylbenzene)

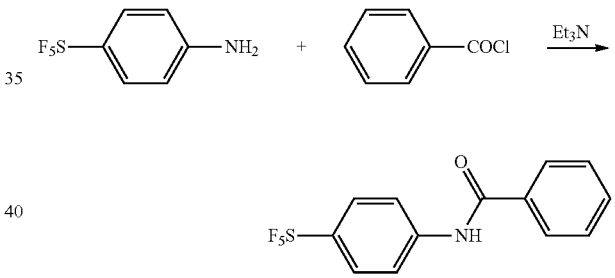

Into a 100 ml flask equipped with a stirrer and a thermometer, 2.0 g (9.12 mmol) of 4-amino pentafluorosulfanylbenzene, 1.11 g (10.9 mmol) of triethylamine and 10 ml of methylene chloride were added, and while stirring at room temperature, 1.53 g (10.9 mmol) of benzoyl chloride was gradually added. The reaction was carried out for 5 hours at the same temperature with stirring.

After completion of the reaction, 50 ml of ethyl acetate was added to the reaction mixture, and the organic phase was separated, which was washed with saturated sodium chloride aqueous solution. After the obtained organic phase was dried over magnesium sulfate, the mixture was filtered and the filtrate was concentrated. The obtained concentrate was purified by a silica-gel column chromatography (eluent; n-hexane/ethyl acetate=5/2 (volume ratio)), to obtain 4-(N-benzoylamino)pentafluorosulfanylbenzene 2.8 g (yield; 95%) as white powder.

Herein, 4-(N-benzoylamino)pentafluorosulfanylbenzene is a novel compound having the following property values.

$^1$H-NMR (CDCl$_3$, δ (ppm)); 7.48-7.63 (3H, m), 7.76 (4H, s), 7.85-7.90 (2H, m), 7.93 (1H, bs)

MS (ES-); 322 (M-1)

Example 2 Synthesis of Compound 2

(Z=NH, R=benzyl (Bn), p=0, m=3, n=1; Synthesis of 4-(3,4,5-tribenzyloxybenzoylamino)pentafluorosulfanyl-benzene)

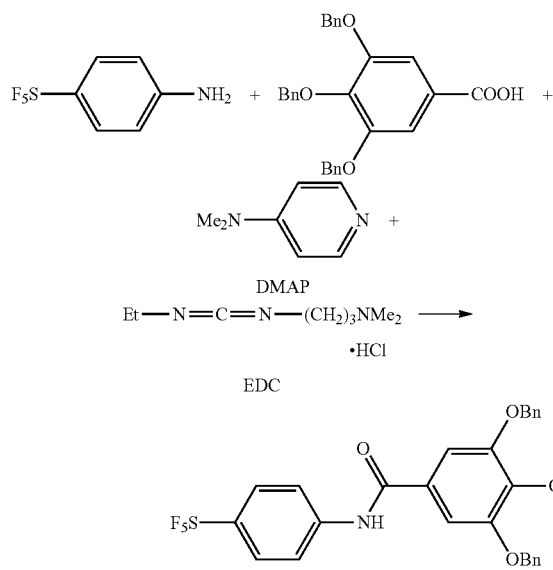

Into a 100 ml flask equipped with a stirrer and a thermometer, 3.0 g (13.7 mmol) of 4-amino pentafluorosulfanylbenzene, 7.22 g (16.4 mmol) of 3,4,5-tribenzyloxybenzoic acid, 500 mg (4.09 mmol) of 4-dimethylaminopyridine (DMAP), 3.15 g (16.4 mmol) of 1-ethyl-3-(3-dimethylaminopropyl)carbodiimide hydrochloride (EDC) and 50 ml of methylene chloride were added, and the reaction was carried out for 5 hours at room temperature with stirring.

After completion of the reaction, the reaction mixture was concentrated under reduced pressure. After 100 ml of ethyl acetate was added to the concentrate, the organic phase was washed with saturated sodium chloride aqueous solution. After the obtained organic phase was dried over magnesium sulfate, the mixture was filtered and the filtrate was concentrated. The obtained concentrate was purified by a silica-gel column chromatography (eluent; n-hexane/ethyl acetate=5/1 (volume ratio)), to obtain 4-(3,4,5-tribenzyloxybenzoylamino)pentafluorosulfanylbenzene 7.99 g (yield; 91%) as white solid.

Herein, 4-(3,4,5-tribenzyloxybenzoylamino)pentafluorosulfanylbenzene is a novel compound having the following property values.

$^1$H-NMR (CDCl$_3$, δ (ppm)); 5.12 (6H, s), 7.08 (2H, s), 7.23-7.42 (15H, m), 7.62-7.80 (5H, m)

Example 3 Synthesis of Compound 3

(Z=NH, R=H, p=0, m=3, n=1; Synthesis of 4-(3,4,5-trihydroxybenzoylamino)pentafluorosulfanylbenzene)

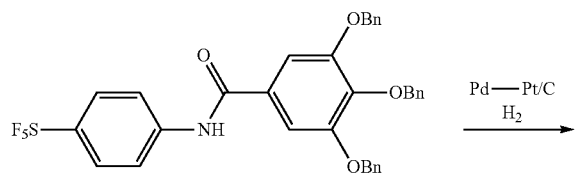

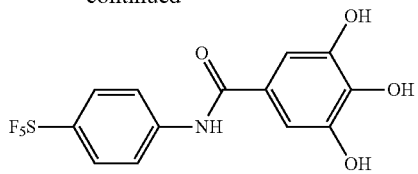

Into a 200 ml flask equipped with a stirrer and a thermometer, 5.0 g (7.79 mmol) of 4-(3,4,5-tribenzyloxybenzoylamino)pentafluorosulfanylbenzene, 1.0 g of palladium (2.5%)-platinum (2.5%)/carbon (56.3% water-containing product), and 100 ml of methanol was added, and the reaction was carried out under hydrogen atmosphere for 5 hours at 40 to 50° C. with stirring.

After completion of the reaction, the reaction mixture was filtered and the filtrate was concentrated. The obtained concentrate was purified by a silica-gel column chromatography (eluent; chloroform/ethyl acetate=from 100/1 to 100/6 (volume ratio)), to obtain 4-(3,4,5-trihydroxybenzoylamino)pentafluorosulfanylbenzene 2.82 g (yield; 97%) as white solid.

Herein, 4-(3,4,5-trihydroxybenzoylamino)pentafluorosulfanylbenzene is a novel compound having the following property values.

$^1$H-NMR (CD$_3$OD, δ (ppm)); 6.98 (2H, s), 7.72-7.79 (2H, m), 7.86 (2H, bd)

EI-MS; 371 (M)

CI-MS; 372 (M+1)

Reference Example 1

(Synthesis of Diacetylcaffeic Acid)

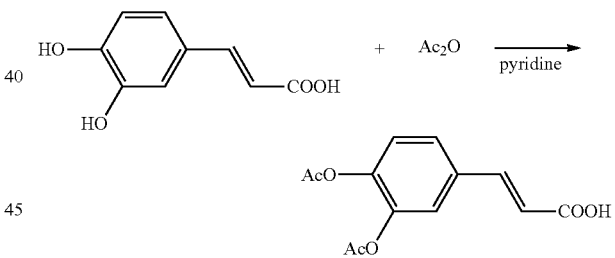

Into a 200 ml flask equipped with a stirrer and a thermometer, 50 ml of pyridine and 5.0 g (27.8 mmol) of caffeic acid were added, and then 14.2 g (139 mmol) of acetic anhydride was gradually added dropwise while cooling with an ice-water bath. The reaction was carried out for 5 hours at room temperature with stirring.

After completion of the reaction, the reaction mixture was concentrated under reduced pressure. 50 ml of methanol was added to the concentrate, heated to reflux to obtain a homogeneous solution once, and subsequently the reaction mixture was cooled down to room temperature. The precipitated solid was isolated by filtration and dried to obtain diacetylcaffeic acid 3.59 g (yield; 49%) as white solid.

Herein, the obtained diacetylcaffeic acid has the following property values.

$^1$H-NMR (DMSO-d$_6$, δ (ppm)); 2.29 (6H, s), 6.54 (1H, d, J=16 Hz), 7.31 (1H, d, J=8.4 Hz), 7.55-7.70 (3H, m), 12.4 (1H, bs)

EI-MS; 264 (M)

Example 4 Synthesis of Compound 4

(Z=NH, R=acetyl (Ac), p=1, m=2, n=1; Synthesis of 4-(3,4-diacetoxycinnamoylamino)pentafluorosulfanylbenzene)

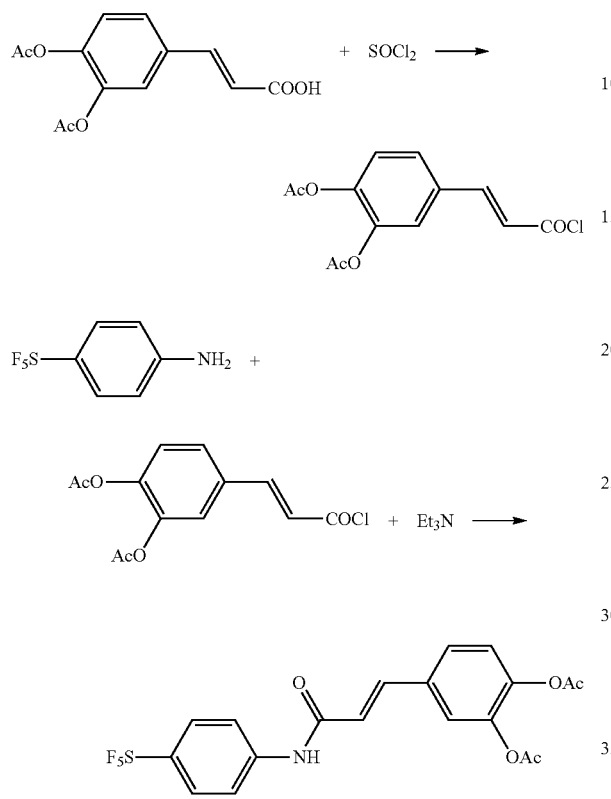

Into a 100 ml flask equipped with a stirrer and a thermometer, 1.74 g (6.6 mmol) of diacetylcaffeic acid and 9.0 ml of thionyl chloride were added. The temperature was gradually raised up to 80° C. slowly with stirring, and the mixture was further stirred for 20 minutes at the same temperature with heating.

After completion of the reaction, the reaction mixture was concentrated under reduced pressure. Chloroform 20 ml was added to the concentrate, and 1.59 g (7.25 mmol) of 4-aminopentafluorosulfanylbenzene and 1.47 g (14.5 mmol) of triethylamine in chloroform solution (20 ml) were gradually added dropwise while cooling with an ice-water bath. The mixture was stirred overnight at room temperature.

After completion of the reaction, the reaction mixture was concentrated under reduced pressure. The obtained concentrate was purified by a silica-gel column chromatography (eluent; n-hexane/ethyl acetate=5/2 (volume ratio)), to obtain 4-(3,4-diacetoxycinnamoylamino)pentafluorosulfanylbenzene 1.94 g (yield; 63%) as white solid.

Herein, 4-(3,4-diacetoxycinnamoylamino)pentafluorosulfanylbenzene is a novel compound having the following property values.

$^1$H-NMR (CDCl$_3$, δ (ppm)); 2.31 (6H, s), 6.35 (1H, d, J=16 Hz), 7.17 (1H, d, J=9.0 Hz), 7.29-7.33 (2H, m), 7.63 (1H, d, J=16 Hz), 7.70 (4H, bs), 7.77 (1H, bs)

EI-MS; 465 (M)

Example 5 Synthesis of Compound 5

(Z=NH, R=H, p=1, m=2, n=1; Synthesis of 4-(3,4-dihydroxycinnamoylamino)pentafluorosulfanylbenzene)

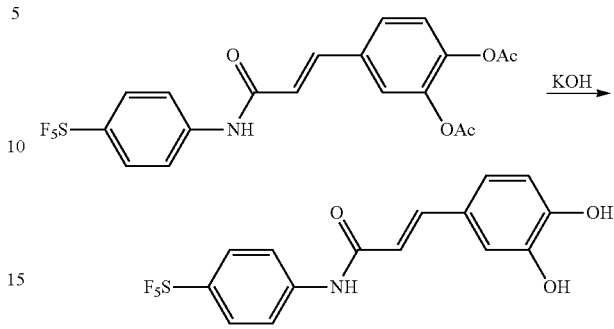

Into a 100 ml flask equipped with a stirrer and a thermometer, 1.91 g (4.1 mmol) of 4-(3,4-diacetoxycinnamoylamino)pentafluorosulfanylbenzene, 12 ml of tetrahydrofuran (THF) and 12 ml of methanol were added, and then 6.6 ml of 0.2 M-potassium hydroxide solution (H$_2$O/MeOH=9/1 (volume ratio)) was gradually added dropwise at inside temperature of 10 to 15° C. with stirring, and stirred for one hour at 15 to 25° C.

After completion of the reaction, 4.1 ml of 1N hydrochloric acid was added, and subsequently, 20 ml of saturated saline was added, then extraction with 30 ml of chloroform was performed twice. The obtained organic phase was dried over magnesium sulfate and concentrated under reduced pressure to obtain 1.61 g of pale yellow solid.

To the obtained solid, chloroform 100 ml was added and stirred for 30 minutes at room temperature. Insoluble matters were filtered off, and the filtrate was dried under reduced pressure at 60° C. to obtain 4-(3,4-dihydroxycinnamoylamino)pentafluorosulfanylbenzene 1.24 g (yield; 79%) as pale yellow solid.

Herein, 4-(3,4-dihydroxycinnamoylamino)pentafluorosulfanylbenzene is a novel compound having the following property values.

$^1$H-NMR (DMSO-d$_6$, δ (ppm)); 6.53 (1H, d, J=16 Hz), 6.77 (1H, d, J=6.0 Hz), 6.89-6.95 (2H, m), 7.45 (1H, d, J=17 Hz), 7.85 (4H, bs), 9.22 (1H, s), 9.51 (1H, s), 10.50 (1H, s)

EI-MS; 381 (M)

Example 6 Synthesis of Compound 6

(Z=O, R=benzyl (Bn), p=0, m=3, n=1; Synthesis of 4-(3,4,5-tribenzyloxybenzoyloxy)pentafluorosulfanylbenzene)

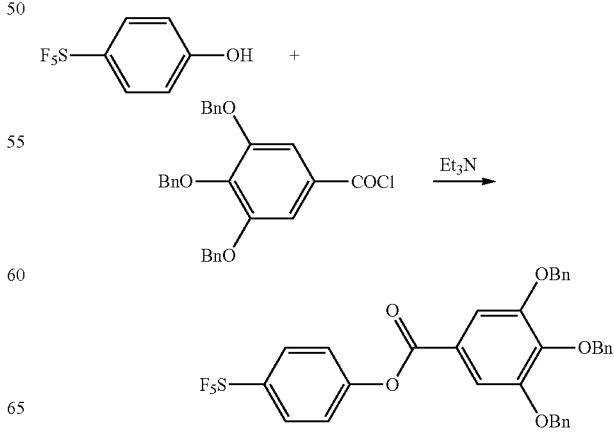

Into a 200 ml flask equipped with a stirrer, a reflux condenser and a thermometer, 7.0 g (13.6 mmol) of 3,4,5-tribenzyloxybenzoic acid and 35 ml of thionyl chloride were added, and the temperature is gradually raised and the mixture was stirred for 30 minutes at 70 to 80° C.

After completion of the reaction, the reaction mixture was concentrated under reduced pressure. 100 ml of chloroform was added to the obtained residue, and subsequently 3.85 g (17.5 mmol) of 4-hydroxypentafluorosulfanylbenzene and 3.54 g (34.9 mmol) of triethylamine were added and stirred for 12 hours at room temperature. After completion of the reaction, the reaction mixture was washed with saturated saline, and the obtained organic phase was dried over magnesium sulfate and concentrated under reduced pressure. The obtained concentrate was purified by a silica-gel column chromatography (eluent; hexane/ethyl acetate=10/1 (volume ratio)), to obtain 4-(3,4,5-tribenzyloxybenzoyloxy) pentafluorosulfanylbenzene 7.66 g (yield; 75%) as white solid.

Herein, 4-(3,4,5-tribenzyloxybenzoyloxy)pentafluorosulfanylbenzene is a novel compound having the following property values.

$^1$H-NMR (CDCl$_3$, δ (ppm)); 5.17 (6H, s), 7.26-7.47 (17H, m), 7.49-7.52 (2H, s), 7.80-7.87 (2H, m)

Example 7 Synthesis of Compound 7

(Z=O, R=H, p=0, m=3, n=1; Synthesis of 4-(3,4,5-trihydroxybenzoyloxy)pentafluorosulfanylbenzene)

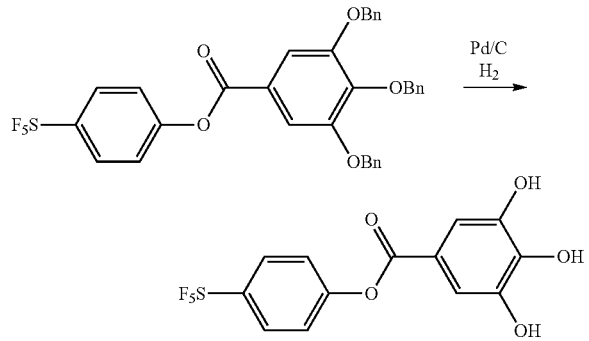

Into a 200 ml flask equipped with a stirrer and a thermometer, 7.0 g (10.9 mmol) of 4-(3,4,5-tribenzyloxybenzoyloxy)pentafluorosulfanylbenzene, 100 ml of 1,2-dimethoxyethane, and subsequently 1.4 g of 5% palladium carbon catalyst (50% water-containing product) were added. The reaction mixture was cooled to room temperature, and while blowing hydrogen gas into the reaction mixture, the temperature thereof is gradually raised from room temperature to 60° C. and the mixture was stirred for four hours.

After completion of the reaction, the reaction mixture was cooled to room temperature and the catalyst was filtered off. The filtrate was concentrated under reduced pressure, and the obtained concentrate was purified by a silica-gel column chromatography (eluent; hexane/ethyl acetate=1/1 (volume ratio)). The fraction containing 4-(3,4,5-trihydroxybenzoyloxy)pentafluorosulfanylbenzene was concentrated under reduced pressure, and the obtained white powder was dried under reduced pressure at 50° C. to obtain mixture of ethyl acetate/4-(3,4,5-trihydroxybenzoyloxy)pentafluorosulfanylbenzene (molar ratio about 1:1) 3.78 g as white powder. Subsequently, it was dried under reduced pressure for 8 hours at 75° C., to obtain 4-(3,4,5-trihydroxybenzoyloxy) pentafluorosulfanylbenzene (free of ethyl acetate) 3.15 g (yield; 78%) as white powder.

Herein, 4-(3,4,5-trihydroxybenzoyloxy)pentafluorosulfanylbenzene is a novel compound having the following property values.

$^1$H-NMR (CD$_3$CN, δ (ppm)); 1.6-3.3 (1H, br), 6.6-7.4 (2H, br), 7.24 (2H, s), 7.40 (2H, bd, J=8.7 Hz), 7.88-7.95 (2H, m) CI-MS; 373 (M+1)

Example 8 Synthesis of Compound 8

(Z=O, R=H, p=0, m=3, n=1; Synthesis of 3-(3,4,5-trihydroxybenzoyloxy)pentafluorosulfanylbenzene)

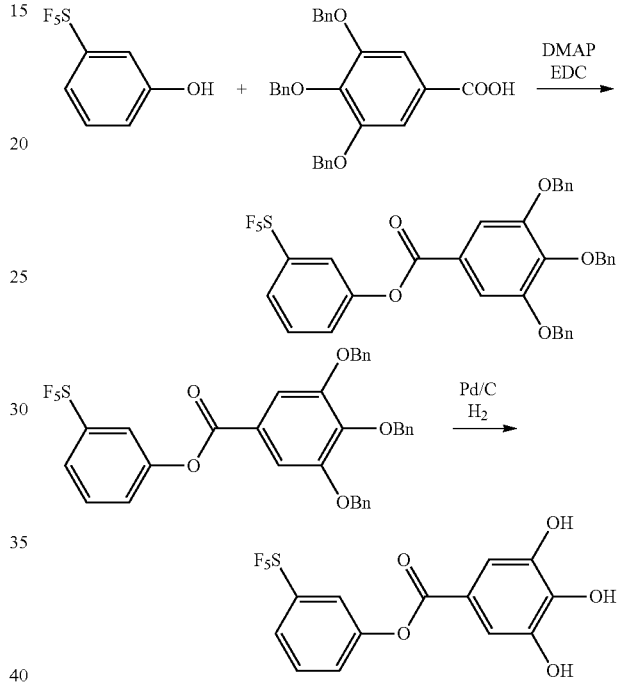

Into a 100 ml flask equipped with a stirrer and a thermometer, 0.60 g (2.73 mmol) of 3-hydroxypentafluorosulfanylbenzene, 1.80 g (4.10 mmol) of 3,4,5-tribenzyloxybenzoic acid, 1.02 g (8.19 mmol) of DMAP, 1.05 g (5.46 mmol) of EDC and 10 ml of methylene chloride were added, and reacted for 5 hours at room temperature with stirring.

After completion of the reaction, 1.0 ml of acetic acid and 10 ml of water were added to the reaction mixture, and extracted with 50 ml of ethyl acetate. After the organic phase was dried over magnesium sulfate, the mixture was filtered and the filtrate was concentrated. When the obtained concentrate was analyzed by an ultra-high-performance liquid chromatography, production of new compound having area percentage of 98.2% was found. According to an LC-MS analysis, the component was found to be 3-(3,4,5-tribenzyloxybenzoyloxy)pentafluorosulfanylbenzene (MS (ES+); 643 (M+1), MS (ES−); 641 (M−1)).

Herein, 3-(3,4,5-tribenzyloxybenzoyloxy)pentafluorosulfanylbenzene is a novel compound.

50 ml of Methanol was added to the above concentrate to form a homogeneous solution, which was transferred to a 200 ml flask equipped with a stirrer, a thermometer and a gas inlet. Into the flask, 0.4 g of 5% palladium carbon catalyst (50% water-containing product) was added, and while blowing hydrogen gas into the reaction mixture, it was stirred for five hours.

After completion of the reaction, the reaction mixture was filtered. The filtrate was concentrated under reduced pressure, and the obtained concentrate was purified by a silica-gel column chromatography (eluent; hexane/ethyl acetate=1/1 (volume ratio)), to obtain 3-(3,4,5-trihydroxybenzoyloxy)pentafluorosulfanylbenzene 0.70 g (yield; 69%) as white powder.

Herein, 3-(3,4,5-trihydroxybenzoyloxy)pentafluorosulfanylbenzene is a novel compound having the following property values.

$^1$H-NMR (DMSO-d$_6$, δ (ppm)); 7.13 (2H, s), 7.59 (1H, bd, J=8.1 Hz), 7.71 (1H, t, J=8.2 Hz), 7.89 (1H, t, J=2.1 Hz), 8.5-10.5 (3H, bs) MS (ES+); 373 (M+1), MS (ES−); 371 (M−1)

Example 9 Synthesis of Compound 9

(Z=NH, R=acetyl (Ac), p=0, m=3, n=1; Synthesis of 4-(3,4,5-triacetoxybenzoylamino)pentafluorosulfanylbenzene)

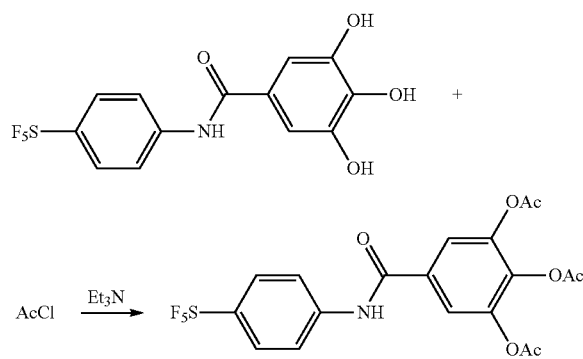

Into a 100 ml flask equipped with a stirrer and a thermometer, 1.11 g (2.99 mmol) of 4-(3,4,5-trihydroxybenzoylamino)pentafluorosulfanylbenzene, 30 ml of methylene chloride, and 1.51 g (15.0 mmol) of triethylamine were added, and 1.17 g (15.0 mmol) of acetyl chloride was gradually added at room temperature while stirring and reacted for 5 hours at the same temperature with stirring.

After completion of the reaction, 20 ml of water was added to the reaction mixture and liquid separation was carried out. The obtained organic phase was once concentrated, 50 ml of ethyl acetate was added to the concentrate, the organic phase was washed with 20 ml of saturated saline twice. After the obtained organic phase was dried over magnesium sulfate, the mixture was filtered and the filtrate was concentrated. 5 ml of chloroform and subsequently n-hexane were added to the concentrate to precipitate crystals. The precipitated crystals were filtered to obtain 4-(3,4,5-triacetoxybenzoylamino)pentafluorosulfanylbenzene 1.05 g (yield; 71%) as white powder.

Herein, 4-(3,4,5-triacetoxybenzoylamino)pentafluorosulfanylbenzene is a novel compound having the following property values.

$^1$H-NMR (DMSO-d$_6$, δ (ppm)); 2.33 (6H, s), 2.35 (3H, s), 7.85 (2H, s), 7.92 (2H, d, J=9.4 Hz), 7.98 (2H, d, J=9.2 Hz), 10.73 (1H, s)

MS (ES+); 498 (M+1), MS (ES−); 496 (M−1)

Example 10 Synthesis of Compound 10

(Z=NH, R=benzyl (Bn), p=0, m=3, n=1; Synthesis of 3-(3,4,5-tribenzyloxybenzoylamino)pentafluorosulfanylbenzene)

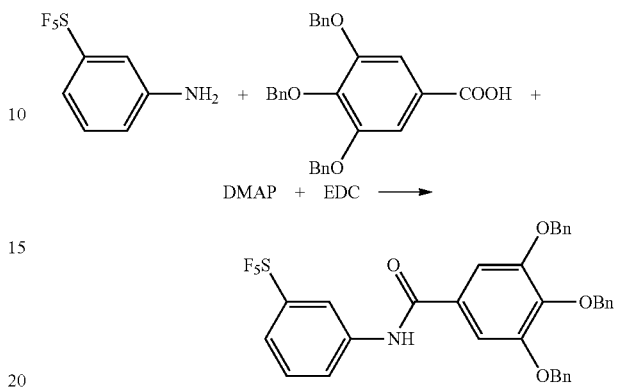

Into a 100 ml flask equipped with a stirrer and a thermometer, 1.0 g (4.56 mmol) of 3-aminopentafluorosulfanylbenzene, 3.01 g (6.84 mmol) of 3,4,5-tribenzyloxybenzoic acid, 0.84 g (6.84 mmol) of DMAP, 1.31 g (6.84 mmol) of EDC and 10 ml of methylene chloride were added, and reacted for 7 hours at 45 to 50° C. with stirring.

After completion of the reaction, 2 ml of acetic acid and 15 ml of water were added and stirred for 30 minutes at room temperature. The organic phase was liquid-separated. After the organic phase was liquid-separated and concentrated once, 50 ml of ethyl acetate were added, the organic phase was washed with 20 ml of saturated saline twice. After the obtained organic phase was dried over magnesium sulfate, the mixture was filtered and the filtrate was concentrated. 10 ml of diethyl ether was added to the obtained concentrate to precipitate crystals. The precipitated crystals was filtered, to obtain 3-(3,4,5-tribenzyloxybenzoylamino)pentafluorosulfanylbenzene 2.90 g (yield; 99%) as white powder.

Herein, 3-(3,4,5-tribenzyloxybenzoylamino)pentafluorosulfanylbenzene is a novel compound having the following property values.

$^1$H-NMR (DMSO-d$_6$, δ (ppm)); 5.04 (2H, s), 5.23 (4H, s), 7.22-7.52 (15H, m), 7.64 (2H, m), 8.04 (1H, m), 8.40 (1H, s), 10.49 (1H, s)

MS (ES+); 642 (M+1), MS (ES−); 640 (M−1)

Example 11 Synthesis of Compound 11

(Z=NH, R=H, p=0, m=3, n=1; Synthesis of 3-(3,4,5-trihydroxybenzoylamino)pentafluorosulfanylbenzene)

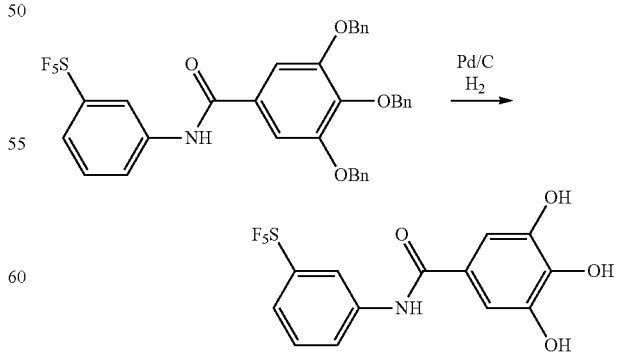

Into a 200 ml flask equipped with a stirrer, a thermometer and a gas inlet, 2.80 g (4.36 mmol) of 3-(3,4,5-tribenzyloxybenzoylamino)pentafluorosulfanylbenzene, and subse quently 0.5 g of 5% palladium carbon catalyst (50% water-containing product) and 30 ml of methanol were added. While blowing hydrogen gas into the reaction mixture, the reaction mixture was stirred for 5 hours at 50° C.

After completion of the reaction, the reaction mixture was filtered. The filtrate was concentrated under reduced pressure, and the obtained concentrate was purified by a reversed-phase silica-gel column chromatography (eluent; water to water/acetonitrile=3/7 (volume ratio)), to obtain 3-(3,4,5-trihydroxybenzoylamino)pentafluorosulfanylbenzene 1.05 g (yield; 65%) as white powder.

Herein, 3-(3,4,5-trihydroxybenzoylamino)pentafluorosulfanylbenzene is a novel compound having the following property values.

$^1$H-NMR (DMSO-$d_6$, δ (ppm)); 6.99 (2H, s), 7.56 (2H, m), 8.04 (1H, m), 8.44 (1H, s), 8.5-9.8 (3H, bs), 10.26 (1H, s)

MS (ES+); 372 (M+1), MS (ES−); 370 (M−1)

Example 12 Synthesis of Compound 12

(Z=NH, R=H, p=0, m=3, n=1; Synthesis of 3-(3,4,5-trihydroxybenzoylamino)-4-hydroxypentafluorosulfanylbenzene)

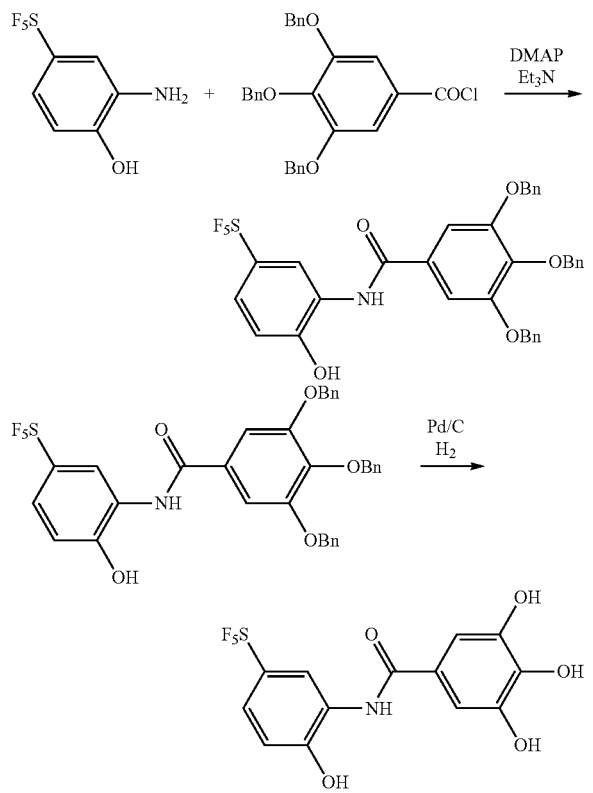

Into a 200 ml flask equipped with a stirrer, a reflux condenser and a thermometer, 1.35 g (3.06 mmol) of 3,4,5-tribenzyloxybenzoic acid, 10 ml of methylene chloride, 0.387 g (3.83 mmol) of triethylamine and 0.1 g of DMAP were added, and 0.425 g (3.57 mmol) of thionyl chloride was added gradually at room temperature while stirring. Subsequently, the reaction was carried out for 2 hours at 40° C. The mixture was cooled to room temperature, to which 0.60 g (2.55 mmol) of 3-amino-4-hydroxypentafluorosulfanylbenzene, 0.36 g (3.57 mmol) of triethylamine and 0.31 g (2.55 mmol) of DMAP were added, and stirred for 6 hours at 40° C.

After completion of the reaction, 10 ml of saturated saline was added. To the organic phase obtained by liquid separation, 5 ml of 1N hydrochloric acid was added and liquid separation was carried out. The obtained organic phase was dried over magnesium sulfate, and concentrated under reduced pressure. The obtained concentrate was purified by a silica-gel column chromatography (eluent; hexane/ethyl acetate=10/1 (volume ratio)), to obtain 3-(3,4,5-tribenzyloxybenzoylamino)-4-hydroxypentafluorosulfanylbenzene 0.72 g (yield 43%) as white powder. Herein, 3-(3,4,5-tribenzyloxybenzoylamino)-4-hydroxypentafluorosulfanylbenzene is a novel compound, and the fact that the obtained material was a target compound was confirmed by LC-MS analysis (MS (ES+); 658 (M+1), MS (ES−); 656 (M−1)). The obtained material was provided to a debenzylation reaction directly.

Into a 200 ml flask equipped with a stirrer, a thermometer and a gas inlet, 0.60 g (0.912 mmol) of 3-(3,4,5-tribenzyloxybenzoylamino)-4-hydroxypentafluorosulfanylbenzene, and subsequently 0.3 g of 5% palladium carbon catalyst (50% water-containing product) and 30 ml of methanol were added, and stirred for 4 hours at 55° C. while blowing hydrogen gas into the reaction mixture.

After completion of the reaction, the reaction mixture was filtered. The filtrate was concentrated under reduced pressure, and 5 ml of chloroform was added to the obtained concentrate to precipitate crystals. The precipitated crystals was filtered, to obtain 3-(3,4,5-trihydroxybenzoylamino)-4-hydroxypentafluorosulfanylbenzene 0.32 g (yield; 91%) as grayish white crystal.

Herein, 3-(3,4,5-trihydroxybenzoylamino)-4-hydroxypentafluorosulfanylbenzene is a novel compound having the following property values.

$^1$H-NMR (DMSO-$d_6$, δ (ppm)); 6.92 (2H, s), 7.03 (1H, d, J=9.0 Hz), 7.51 (1H, dd, J=2.8, 9.0 Hz), 8.48 (1H, d, J=2.8 Hz), 9.10 (1H, s), 8.6-9.8 (3H, br), 10.6-11.8 (1H, br) MS (ES+); 388 (M+1), MS (ES−); 386 (M−1)

Example 13 Synthesis of Compound 13

(Z=NH/NH, R=benzyl (Bn), p=0, m=3, n=2; Synthesis of 3,4-bis(3,4,5-tribenzyloxybenzoylamino)pentafluorosulfanylbenzene)

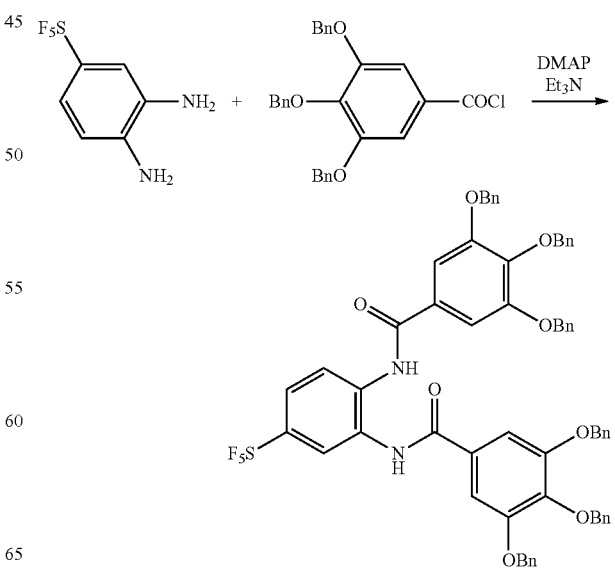

Into a 100 ml flask equipped with a stirrer, a reflux condenser and a thermometer, 2.48 g (5.63 mmol) of 3,4,5-tribenzyloxybenzoic acid, 10 ml of methylene chloride, 0.648 g (6.40 mmol) of triethylamine and 0.1 g of DMAP were added, and 0.762 g (6.40 mmol) of thionyl chloride was added gradually at room temperature while stirring. Subsequently, the reaction was carried out for 2 hours at 40° C. The mixture was cooled to room temperature, to which 0.60 g (2.56 mmol) of 3,4-diaminopentafluorosulfanylbenzene, 10 ml of methylene chloride, 0.648 g (6.40 mmol) of triethylamine and 0.313 g (2.56 mmol) of DMAP were added, and stirred for 6 hours at 40° C.

After completion of the reaction, 10 ml of water and 10 ml of chloroform were added. To the organic phase obtained by liquid separation, 10 ml of 1N hydrochloric acid was added and liquid separation was carried out. The obtained organic phase was washed with 10 ml of saturated aqueous solution of sodium bicarbonate, dried over magnesium sulfate, and concentrated under reduced pressure. 10 ml of methanol was added to the obtained concentrate to precipitate crystals.

The precipitated crystals was filtered, to obtain 3,4-bis(3,4,5-tribenzyloxybenzoylamino)pentafluorosulfanylbenzene 1.95 g (yield; 71%) as greyish white powder.

Herein, 3,4-bis(3,4,5-tribenzyloxybenzoylamino)pentafluorosulfanylbenzene is a novel compound having the following property values.

$^1$H-NMR (CD$_3$CN, δ (ppm)); 4.92 (4H, m), 5.02 (8H, s), 7.20-7.48 (34H, m), 7.77 (1H, dd, J=2.6, 9.0 Hz), 7.97 (1H, d, J=9.0 Hz), 8.23 (1H, d, J=2.6 Hz), 9.31 (1H, s), 9.38 (1H, s)

MS (ES+); 1080 (M+1), MS (ES−); 1078 (M−1)

Example 14 Synthesis of Compound 14

(Z=NH/NH, R=H, p=0, m=3, n=2; Synthesis of 3,4-bis(3,4,5-trihydroxybenzoylamino)pentafluorosulfanylbenzene)

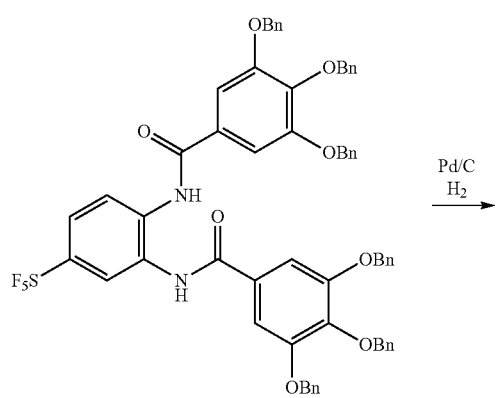

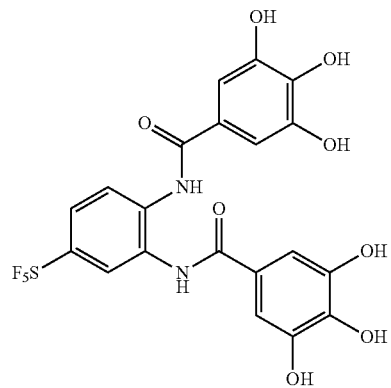

Into a 100 ml flask equipped with a stirrer, a thermometer and a gas inlet, 1.40 g (1.30 mmol) of 3,4-bis(3,4,5-tribenzyloxybenzoylamino)pentafluorosulfanylbenzene, and subsequently 0.6 g of 5% palladium carbon catalyst (50% water-containing product) and 50 ml of methanol were added. While blowing hydrogen gas into the reaction mixture, the reaction mixture was stirred for 4 hours at 50° C.

After completion of the reaction, the reaction mixture was filtered. The filtrate was concentrated under reduced pressure. After 30 ml of 2-methyltetrahydrofuran was added to the obtained concentrate to form a homogeneous solution, 10 ml of saturated aqueous solution of sodium bicarbonate was mixed and the liquid separation was carried out. The obtained organic phase was concentrated under reduced pressure, and the concentrate was purified by a reversed-phase silica-gel column chromatography (eluent; water to water/acetonitrile=3/7 (volume ratio)), to obtain 3,4-bis(3,4,5-trihydroxybenzoylamino)pentafluorosulfanylbenzene 0.47 g (yield; 67%) as white powder.

Herein, 3,4-bis(3,4,5-trihydroxybenzoylamino)pentafluorosulfanylbenzene is a novel compound having the following property values.

$^1$H-NMR (DMSO-d$_6$, δ (ppm)); 6.94 (2H, s), 6.97 (2H, s), 7.76 (1H, dd, J=2.6, 9.1 Hz), 8.01 (1H, d, J=9.0 Hz), 8.13 (1H, d, J=2.6 Hz), 8.5-9.8 (6H, br), 9.88 (1H, s), 9.95 (1H, s)

MS (ES+); 539 (M+1), MS (ES−); 537 (M−1)

Example 15 Synthesis of Compound 15

(Z=NH/NH, R=benzyl (Bn), p=0, m=3, n=2; Synthesis of 4-hydroxy-3,5-bis(3,4,5-tribenzyloxybenzoylamino)pentafluorosulfanylbenzene)

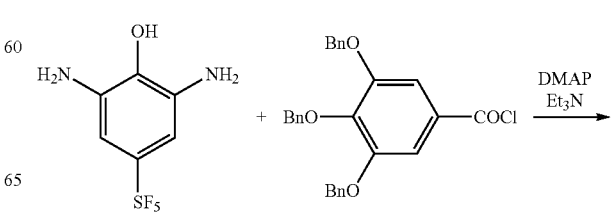

-continued

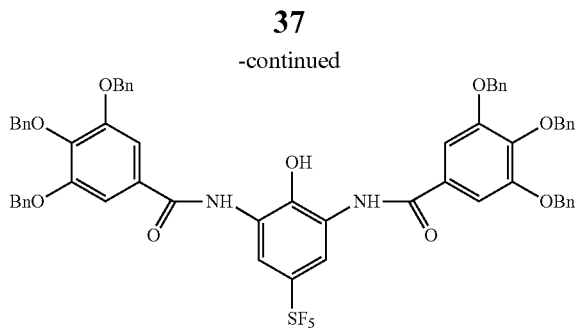

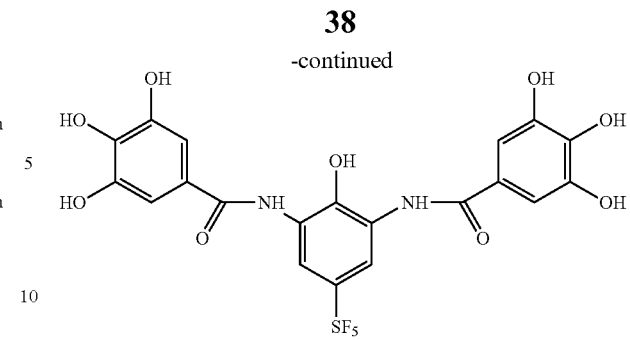

Into a 100 ml flask equipped with a stirrer, a reflux condenser and a thermometer, 3.93 g (8.93 mmol) of 3,4,5-tribenzyloxybenzoic acid, 20 ml of methylene chloride, 0.941 g (9.30 mmol) of triethylamine and 0.1 g of DMAP were added, and 1.063 g (8.93 mmol) of thionyl chloride was added gradually at room temperature while stirring. Subsequently, the reaction was carried out for 3 hours at 40 to 50° C. The mixture was cooled to room temperature, to which 0.93 g (3.72 mmol) of 3, 5-diamino-4-hydroxypentafluorosulfanylbenzene, 10 ml of methylene chloride, 2.26 g (22.32 mmol) of triethylamine and 0.68 g (5.58 mmol) of DMAP were added, and stirred for 6 hours at 40° C.

After completion of the reaction, 10 ml of water and 10 ml of chloroform were added. To the organic phase obtained by liquid separation, 10 ml of 1N hydrochloric acid was added and liquid separation was carried out. The obtained organic phase was washed with 10 ml of saturated aqueous solution of sodium bicarbonate, dried over magnesium sulfate, and concentrated under reduced pressure. The obtained concentrate was purified by a silica-gel column chromatography (eluent; hexane/ethyl acetate=1/1 (volume ratio)), to obtain 4-hydroxy-3, 5-bis(3,4,5-tribenzyloxybenzoylamino)pentafluorosulfanylbenzene 2.46 g (yield; 60%) as white powder.

Herein, 4-hydroxy-3,5-bis(3,4,5-tribenzyloxybenzoylamino)pentafluorosulfanylbenzene is a novel compound having the following property values.

$^1$H-NMR (DMSO-$d_6$, δ (ppm)); 5.05 (4H, s), 5.23 (8H, s), 7.22-7.55 (34H, m), 8.02 (2H, s), 9.96 (2H, s), 10.65 (1H, bs)

Example 16 Synthesis of Compound 16

(Z=NH/NH, R=H, p=0, m=3, n=2; Synthesis of 4-hydroxy-3,5-bis(3,4,5-trihydroxybenzoylamino)pentafluorosulfanylbenzene)

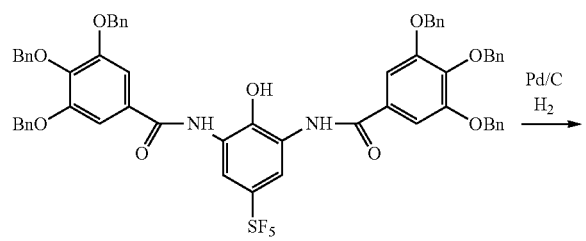

Into a 100 ml flask equipped with a stirrer, a thermometer and a gas inlet, 1.20 g (1.10 mmol) of 4-hydroxy-3,5-bis(3,4,5-tribenzyloxybenzoylamino)pentafluorosulfanylbenzene, and subsequently 0.3 g of 5% palladium carbon catalyst (50% water-containing product) and 30 ml of methanol were added. While blowing hydrogen gas into the reaction mixture, the reaction mixture was stirred for 6 hours at 50 to 60° C.

After completion of the reaction, the reaction mixture was filtered. The filtrate was concentrated under reduced pressure. After 5 ml of ethyl acetate was added to the obtained concentrate to form a homogeneous solution, n-hexane was added to precipitate crystals. The precipitated crystals were filtered, to obtain 4-hydroxy-3,5-bis(3,4,5-trihydroxybenzoylamino)pentafluorosulfanylbenzene 0.58 g (yield; 95%) as white powder.

Herein, 4-hydroxy-3,5-bis(3,4,5-trihydroxybenzoylamino)pentafluorosulfanylbenzene is a novel compound having the following property values.

$^1$H-NMR (DMSO-$d_6$, δ (ppm)); 7.00 (4H, s), 8.14 (2H, s), 8.95 (2H, s), 9.28 (4H, s), 9.64 (2H, s), 11.04 (1H, s), 9.88 (1H, s), 9.95 (1H, s)

MS (ES+); 555 (M+1), MS (ES−); 553 (M−1)

Example 17 Synthesis of Compound 17

(Z=O/NH, R=benzyl (Bn), p=0, m=3, n=2; Synthesis of 4-(3,4,5-tribenzyloxybenzoylamino)-3-(3,4,5-tribenzyloxybenzoyloxy)pentafluorosulfanylbenzene)

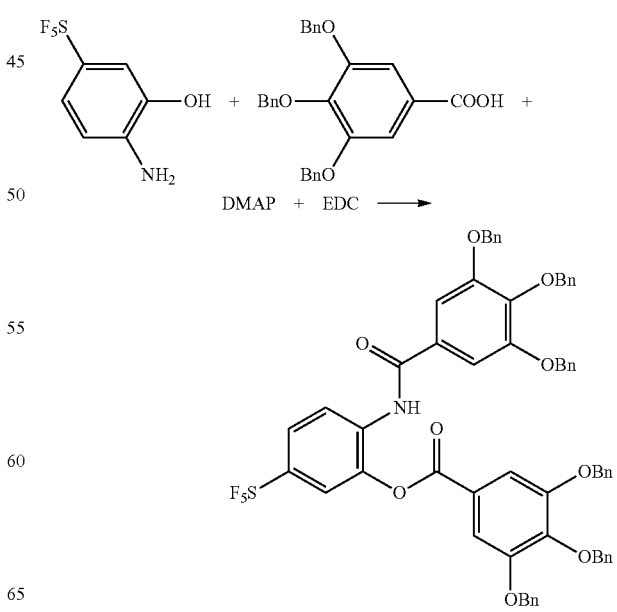

Into a 100 ml flask equipped with a stirrer and a thermometer, 0.32 g (1.36 mmol) of 4-amino-3-hydroxypentafluorosulfanylbenzene, 1.80 g (4.08 mmol) of 3,4,5-tribenzyloxybenzoic acid, 1.00 g (8.16 mmol) of DMAP, 1.56 g (8.16 mmol) of EDC and 10 ml of methylene chloride were added, and reacted for 7 hours at 45° C. with stirring.

After completion of the reaction, 2 ml of acetic acid and 10 ml of water were added and stirred for 30 minutes at room temperature. The organic phase was separated by liquid-separation, and after the obtained organic phase was dried over magnesium sulfate, the mixture was filtered and the filtrate was concentrated. The obtained concentrate was purified by a silica-gel column chromatography (eluent; hexane/ethyl acetate=1/1 (volume ratio)), to obtain 4-(3,4,5-tribenzyloxybenzoylamino)-3-(3,4,5-tribenzyloxybenzoyloxy)pentafluorosulfanylbenzene 0.42 g (yield; 29%) as white powder.

Herein, 4-(3,4,5-tribenzyloxybenzoylamino)-3-(3,4,5-tribenzyloxybenzoyloxy)pentafluorosulfanylbenzene is a novel compound having the following property values.

1H-NMR (DMSO-$d_6$, δ (ppm)); 4.84 (2H, s), 4.89 (2H, s), 5.03 (4H, s), 5.06 (4H, s), 7.18-7.42 (32H, m), 7.59 (2H, s), 7.94 (1H, dd, J=2.4, 9.0 Hz), 8.00 (1H, d, J=9.0 Hz), 8.09 (1H, d, J=2.4 Hz), 10.36 (1H, s)

MS (ES+); 1081 (M+1), MS (ES−); 1079 (M−1)

Example 18 Synthesis of Compound 18

(Z=O/NH, R=H, p=0, m=3, n=2; Synthesis of 4-(3,4,5-trihydroxybenzoylamino)-3-(3,4,5-trihydroxybenzoyloxy)pentafluorosulfanylbenzene)

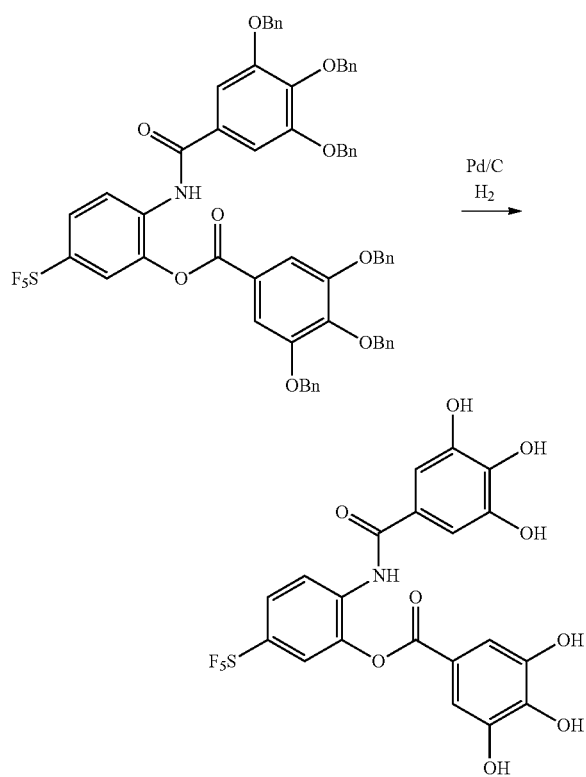

Into a 100 ml flask equipped with a stirrer, a thermometer and a gas inlet, 0.28 g (0.25 mmol) of 4-(3,4,5-tribenzyloxybenzoylamino)-3-(3,4,5-tribenzyloxybenzoyloxy)pentafluorosulfanylbenzene, and subsequently 0.1 g of 5% palladium carbon catalyst (50% water-containing product) and 10 ml of methanol were added. While blowing hydrogen gas into the reaction mixture, the reaction mixture was stirred for 3 hours at room temperature.

After completion of the reaction, the reaction mixture was filtered and the filtrate was concentrated under reduced pressure. 5 ml of diethyl ether was added to the obtained concentrate to precipitate crystals, and the obtained crystals were filtered, to obtain 4-(3,4,5-trihydroxybenzoylamino)-3-(3,4,5-trihydroxybenzoyloxy)pentafluorosulfanylbenzene 0.05 g (yield; 37%) as white powder.

Herein, 4-(3,4,5-trihydroxybenzoylamino)-3-(3,4,5-trihydroxybenzoyloxy)pentafluorosulfanylbenzene is a novel compound having the following property values.

1H-NMR (CD$_3$CN, δ (ppm)); 6.90 (2H, s), 7.28 (2H, s), 7.76 (1H, dd, J=2.4, 9.0 Hz), 7.85 (1H, d, J=2.5 Hz), 8.30 (1H, d, J=8.8 Hz), 8.45 (1H, s)

Example 19 Synthesis of Compound 19

(Z=NH, R=methylenedioxy, p=1, m=2, n=1; Synthesis of 4-(3,4-methylenedioxycinnamoylamino)pentafluorosulfanylbenzene)

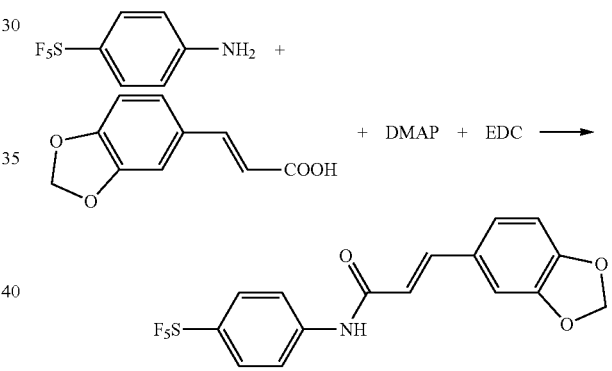

Into a 100 ml flask equipped with a stirrer and a thermometer, 1.00 g (4.56 mmol) of 4-aminopentafluorosulfanylbenzene, 1.31 g (6.84 mmol) of 3,4-methylenedioxycinnamic acid, 1.11 g (9.12 mmol) of DMAP, 1.748 g (9.12 mmol) of EDC and 10 ml of methylene chloride were added, and the reaction was carried out for 7 hours at 40 to 50° C. with stirring.

After completion of the reaction, 2 ml of acetic acid and 10 ml of water were added, and stirred for 30 minutes at room temperature. The organic phase was separated by liquid-separation. After the obtained organic phase was dried over magnesium sulfate, the mixture was filtered and the filtrate was concentrated. 5 ml of diethyl ether, and subsequently n-hexane were added to the obtained concentrate to precipitate crystals. The precipitated crystals were filtered, to obtain 4-(3,4-methylenedioxycinnamoylamino)pentafluorosulfanylbenzene 1.06 g (yield; 59%) as yellowish white powder.

Herein, 4-(3,4-methylenedioxycinnamoylamino)pentafluorosulfanylbenzene is a novel compound having the following property values.

$^1$H-NMR (CD$_3$CN, δ (ppm)); 6.02 (2H, s), 6.54 (1H, d, J=15.6 Hz), 6.89 (1H, d, J=8.0 Hz), 7.08-7.21 (2H, m), 7.61 (1H, d, J=15.6 Hz), 7.74-7.87 (4H, m), 8.78 (1H, s)
MS (ES+); 394 (M+1), MS (ES−); 392 (M−1)

Reference Example 2

Synthesis of 4-acetoxy-3-methoxycinnamic acid

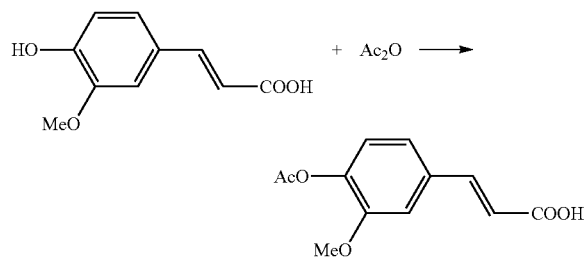

Into a 100 ml flask equipped with a stirrer and a thermometer, 3.00 g (15.45 mmol) of 4-hydroxy-3-methoxycinnamic acid and 7.89 g (77.25 mmol) of acetic anhydride were added, and the reaction was carried out for 10 hours at 80 to 100° C. with stirring.

After completion of the reaction, the reaction mixture was cooled to room temperature and poured into 30 ml of ice-water while stirring. The precipitated crystals were filtered, and dried at 50° C. under reduced pressure to obtain 4-acetoxy-3-methoxycinnamic acid 3.10 g (yield; 85%) as yellowish white powder.
MS (ES−); 235 (M−1)

Example 20 Synthesis of Compound 20

(Z=NH, R=methyl (Me)/acetyl (Ac), p=1, m=2, n=1; Synthesis of 4-(4-acetoxy-3-methoxycinnamoylamino)pentafluorosulfanylbenzene)

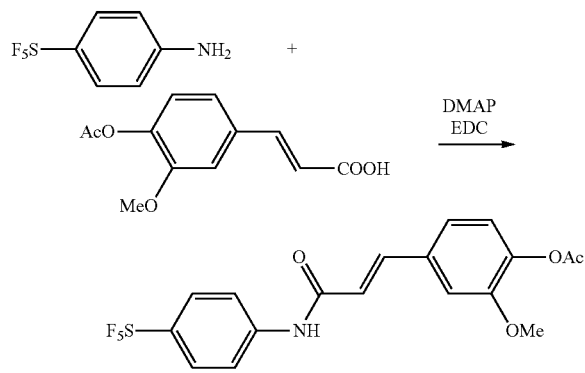

Into a 100 ml flask equipped with a stirrer and a thermometer, 0.50 g (2.28 mmol) of 4-aminopentafluorosulfanylbenzene, 0.64 g (2.74 mmol) of 4-acetoxy-3-methoxycinnamic acid, 0.35 g (2.83 mmol) of DMAP, 0.53 g (2.74 mmol) of EDC and 5 ml of methylene chloride were added, and the reaction was carried out for 7 hours at 45° C. with stirring.

After completion of the reaction, 1 ml of acetic acid and 10 ml of water were added, and stirred for 30 minutes at room temperature. After 30 ml of chloroform was added to the reaction mixture, the organic phase was separated by liquid-separation. The obtained organic phase was dried over magnesium sulfate, the mixture was filtered and the filtrate was concentrated. The obtained concentrate was purified by a silica-gel column chromatography (eluent; hexane/ethyl acetate=1/1 (volume ratio)), to obtain 4-(4-acetoxy-3-methoxycinnamoylamino)pentafluorosulfanylbenzene 0.35 g (yield; 35%) as white powder.

Herein, 4-(4-acetoxy-3-methoxycinnamoylamino)pentafluorosulfanylbenzene is a novel compound having the following property values.

$^1$H-NMR (DMSO-d$_6$, δ (ppm)); 2.36 (3H, s), 3.81 (3H, s), 6.31 (1H, d, J=15.4 Hz), 7.07-7.12 (3H, m), 7.67 (1H, d, J=15.4 Hz), 7.67 (1H, bs), 7.73 (4H, s)
MS (ES+); 438 (M+1), MS (ES−); 436 (M−1)

Example 21 Synthesis of Compound 21

(Z=NH, R=methyl (Me)/H, p=1, m=2, n=1; Synthesis of 4-(4-hydroxy-3-methoxycinnamoylamino)pentafluorosulfanylbenzene)

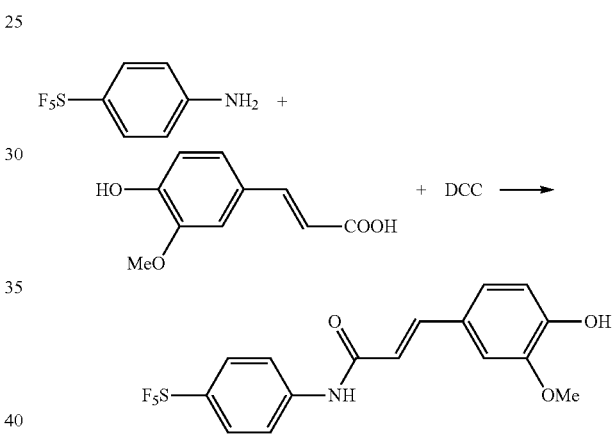

Into a 100 ml flask equipped with a stirrer, a reflux condenser and a thermometer, 1.13 g (5.15 mmol) of 4-aminopentafluorosulfanylbenzene, 1.00 g (5.15 mmol) of 4-hydroxy-3-methoxycinnamic acid, 1.06 g (5.15 mmol) of dicyclohexylcarbodiimide (DCC) and 10 ml of 2-methyltetrahydrofuran (MTHF) were added, and the reaction was carried out for 10 hours at 80° C. with stirring.

After completion of the reaction, 20 ml of methanol was added. The mixture was stirred for 30 minutes at room temperature to precipitate crystals, the crystals were filtered off, and the filtrate was concentrated. The obtained concentrate was purified by a silica-gel column chromatography (eluent; hexane/ethyl acetate=1/1 (volume ratio)), to obtain 4-(4-hydroxy-3-methoxycinnamoylamino)pentafluorosulfanylbenzene 0.84 g (yield; 41%) as white powder.

Herein, 4-(4-hydroxy-3-methoxycinnamoylamino)pentafluorosulfanylbenzene is a novel compound having the following property values.

1H-NMR (DMSO-d$_6$, δ (ppm)); 3.84 (3H, s), 6.64 (1H, d, J=15.7 Hz), 6.84 (1H, d, J=8.2 Hz), 7.09 (1H, dd, J=8.2, 1.9 Hz), 7.21 (1H, d, J=1.9 Hz), 7.56 (1H, d, J=15.7 Hz), 7.84-7.91 (4H, m), 9.61 (1H, bs), 10.53 (1H, s) MS (ES+); 396 (M+1), MS (ES−); 394 (M−1)

Example 22 Synthesis of Compound 22

(Z=O, R=acetyl (Ac), p=1, m=2, n=1; Synthesis of 4-(3,4-diacetoxycinnamoyloxy)pentafluorosulfanylbenzene)

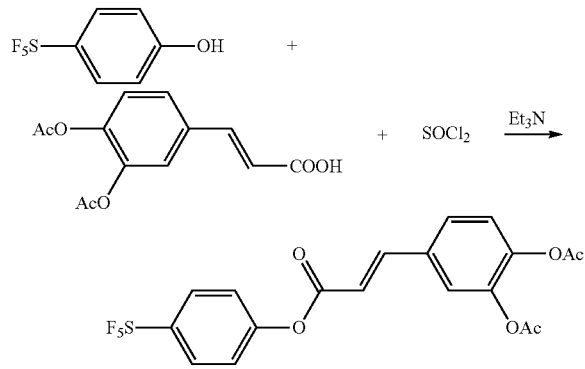

Into a 100 ml flask equipped with a stirrer and a thermometer, 0.70 g (2.65 mmol) of diacetylcaffeic acid, 15 ml of methylene chloride and 0.47 g (3.97 mmol) of thionyl chloride were added, and further, 0.67 g (6.63 mmol) of triethylamine was added gradually for 15 minutes at room temperature while stirring, and the reaction was carried out for 2 hours at the same temperature.

Subsequently, 0.53 g (2.39 mmol) of 4-hydroxypentafluorosulfanylbenzene was added, and the reaction was carried out for 7 hours at the same temperature.

After completion of the reaction, 30 ml of water and 30 ml of methylene chloride were added to the reaction mixture and liquid separation was carried out. The obtained organic phase was dried over magnesium sulfate, and concentrated under reduced pressure. The obtained concentrate was purified by a silica-gel column chromatography (eluent; n-hexane/ethyl acetate=5/2 to 1/1 (volume ratio)), to obtain 4-(3,4-diacetoxycinnamoyloxy)pentafluorosulfanylbenzene 0.83 g (yield; 67%) as white solid.

Herein, 4-(3,4-diacetoxycinnamoyloxy)pentafluorosulfanylbenzene is a novel compound having the following property values.

$^1$H-NMR (CDCl$_3$, δ (ppm)); 2.30 (3H, s), 2.31 (3H, s), 6.93 (1H, d, J=16.0 Hz), 7.38 (1H, d, J=8.4 Hz), 7.51 (1H, d, J=9.0 Hz), 7.78 (1H, dd, J=2.0, 8.5 Hz), 7.82 (1H, d, J=2.0 Hz), 7.91 (1H, d, J=16.0 Hz), 8.02 (1H, m)
MS (ES+); 467 (M+1), 489 (M+Na)

Example 23 Synthesis of Compound 23

(Z=NH, R=H, p=0, m=3, n=1; Synthesis of 4-(2,4,6-trihydroxybenzoylamino)pentafluorosulfanylbenzene)

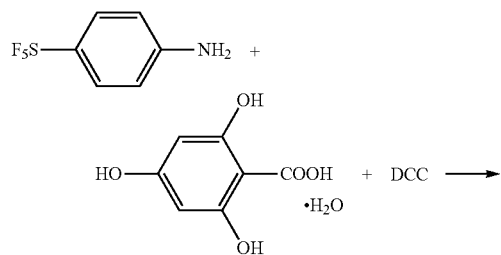

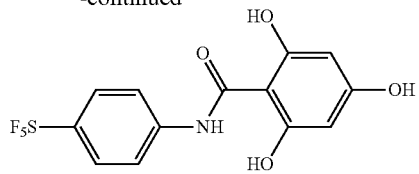

Into a 100 ml flask equipped with a stirrer, a reflux condenser and a thermometer, 1.17 g (5.32 mmol) of 4-aminopentafluorosulfanylbenzene, 1.00 g (5.32 mmol) of 2,4,6-trihydroxybenzoic acid monohydrate, 2.20 g (10.64 mmol) of DCC and 10 ml of MTHF were added, and the reaction was carried out for 10 hours at 80° C. with stirring.

After completion of the reaction, 30 ml of methanol was added. The mixture was stirred for 30 minutes at room temperature to precipitate crystals, the crystals were filtered off, and the filtrate was concentrated. The obtained concentrate was purified by a silica-gel column chromatography (eluent; hexane/ethyl acetate=1/1 (volume ratio)), to obtain 4-(2,4,6-trihydroxybenzoylamino)pentafluorosulfanylbenzene 0.24 g (yield; 12%) as white needle crystal.

Herein, 4-(2,4,6-trihydroxybenzoylamino)pentafluorosulfanylbenzene is a novel compound having the following property values.

$^1$H-NMR (DMSO-d$_6$, δ (ppm)); 5.88 (2H, s), 7.81-7.90 (4H, m), 10.16 (1H, s), 11.10 (1H, bs), 12.48 (2H, bs)
MS (ES+); 372 (M+1), MS (ES−); 370 (M−1)

Example 24 Synthesis of Compound 24

(Z=NH, R=H, p=1, m=3, n=1; Synthesis of 4-(3,4,5-trihydroxycinnamoylamino)pentafluorosulfanylbenzene)

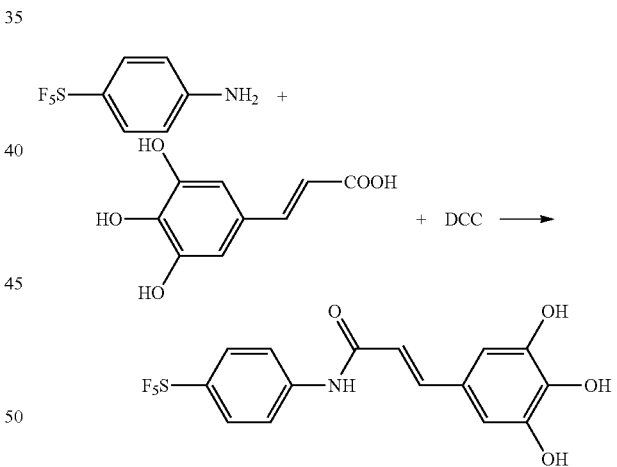

Into a 100 ml flask equipped with a stirrer, a reflux condenser and a thermometer, 1.12 g (5.10 mmol) of 4-aminopentafluorosulfanylbenzene, 1.00 g (5.10 mmol) of 3,4,5-trihydroxycinnamic acid, 1.26 g (6.12 mmol) of DCC and 10 ml of MTHF were added, and the reaction was carried out for 8 hours at 80° C. with stirring.

After completion of the reaction, 30 ml of methanol was added. The mixture was stirred for 30 minutes at room temperature to precipitate crystals, the crystals were filtered off, and the filtrate was concentrated. The obtained concentrate was purified by a silica-gel column chromatography (eluent; hexane/ethyl acetate=1/1 (volume ratio)), to obtain 4-(3,4,5-trihydroxycinnamoylamino)pentafluorosulfanylbenzene 0.65 g (yield; 32%) as white powder.

Herein, 4-(3,4,5-trihydroxycinnamoylamino)pentafluorosulfanylbenzene is a novel compound having the following property values.

$^1$H-NMR (DMSO-d$_6$, δ (ppm)); 6.49 (1H, d, J=15.5 Hz), 6.57 (2H, s), 7.37 (1H, d, J=15.5 Hz), 7.84-7.90 (4H, m), 8.00-10.00 (3H, br), 10.50 (1H, bs) MS (ES+); 398 (M+1), MS (ES−); 396 (M−1)

MS (ES+); 398 (M+1), MS (ES−); 397 (M−1)

Example 25 Synthesis of Compound 25

(Z=NH, R=acetyl (Ac), p=1, m=3, n=1; Synthesis of 4-(3,4,5-triacetoxycinnamoylamino)pentafluorosulfanylbenzene)

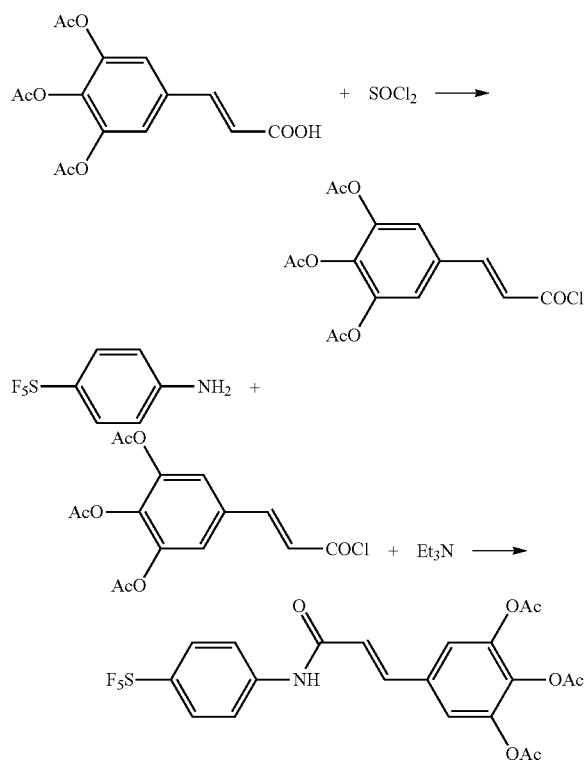

Into a 100 ml flask equipped with a stirrer and a thermometer, 3.29 g (10.20 mmol) of triacetoxycinnamic acid and 30 ml of methylene chloride were added, and further, while cooling with an ice-water bath, 1.83 g (15.3 mmol) of thionyl chloride and subsequently 2.06 g (20.4 mmol) of triethylamine were added; then, the temperature is gradually raised to room temperature, and the mixture was further stirred for 3 hours.

To the obtained reaction mixture, 1.56 g (7.14 mmol) of 4-aminopentafluorosulfanylbenzene and 1.42 g (10.2 mmol) of triethylamine were added and the reaction was carried out for 5 hours at the same temperature.

After completion of the reaction, 30 ml of water was added and liquid separation operation was carried out. The organic phase was dried over magnesium sulfate and concentrated under reduced pressure. The obtained concentrate was purified by a silica-gel column chromatography (eluent; n-hexane/ethyl acetate=9/1 to 3/7 (volume ratio)), to obtain 4-(3,4,5-triacetoxycinnamoylamino)pentafluorosulfanylbenzene 0.46 g (yield; 9%) as white powder.

Herein, 4-(3,4,5-triacetoxycinnamoylamino)pentafluorosulfanylbenzene is a novel compound having the following property values.

$^1$H-NMR (CDCl$_3$, δ (ppm)); 2.28 (6H, s), 2.31 (3H, s), 6.35 (1H, d, J=15.4 Hz), 7.23-7.31 (2H, m), 7.60 (1H, d, J=15.4 Hz), 7.66-7.73 (4H, m) MS (ES+); 525 (M+2), MS (ES−); 522 (M−1)

Example 26 Synthesis of Compound 26

(Z=NH, p=0, n=11, m=2; Synthesis of 4-(3,5-bis(3-methyl-2-butenyloxy)benzoylamino)pentafluorosulfanylbenzene)

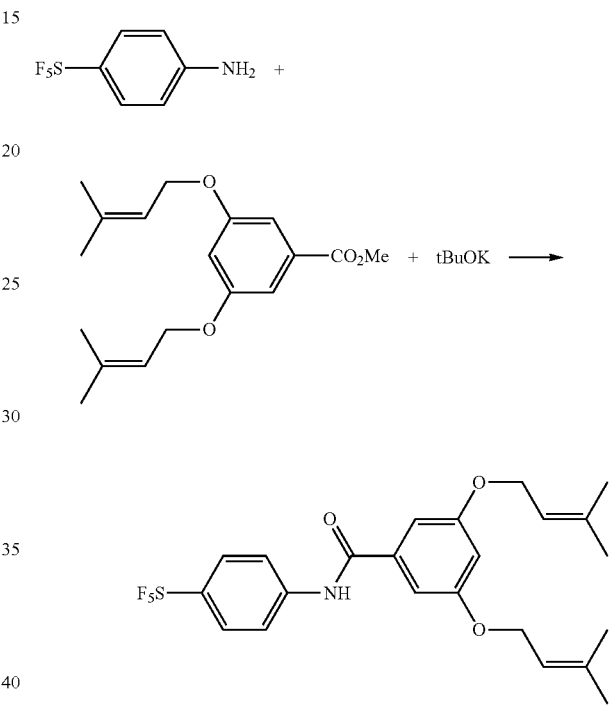

Into a 100 ml flask equipped with a stirrer and a thermometer, 1.10 g (3.61 mmol) of methyl 3,5-bis(3-methyl-2-butenyloxy)benzoate, 0.95 g (4.33 mmol) of 4-aminopentafluorosulfanylbenzene and 5 ml of DMF were added, and further, 0.45 g (3.97 mmol) of potassium tert-butoxide was gradually added at room temperature while stirring, and stirred further 5 hours at 50° C.

After completion of the reaction, the mixture was cooled to room temperature, to which 50 ml of toluene and subsequently 1.0 ml of 6N hydrochloric acid were gradually added. Liquid separation operation was performed twice with 20 ml of water. The organic phase was dried over magnesium sulfate, and concentrated under reduced pressure. The obtained concentrate was purified by a silica-gel column chromatography (eluent; n-hexane/ethyl acetate=9/1 to 7/3 (volume ratio)), to obtain 4-(3,5-bis(3-methyl-2-butenyloxy)benzoylamino)pentafluorosulfanylbenzene 1.03 g (yield; 58%) as white powder.

Herein, 4-(3,5-bis(3-methyl-2-butenyloxy)benzoylamino)pentafluorosulfanylbenzene is a novel compound having the following property values.

$^1$H-NMR (CDCl$_3$, δ (ppm)); 1.76 (6H, s), 1.81 (6H, s), 4.54 (4H, d, J=6.8 Hz), 5.49 (2H, m), 6.68 (1H, t, J=2.3 Hz), 6.98 (2H, d, J=2.3 Hz), 7.70-7.79 (4H, m), 7.90 (1H, bs)

Example 27 Synthesis of Compound 27

(Z=NH, p=0, n=1, m=2; Synthesis of 4-(4-(3-methyl-2-butenyloxy)-3-methoxybenzoylamino)pentafluorosulfanylbenzene)

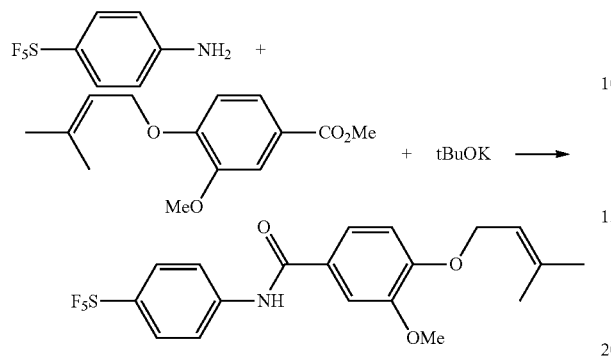

A reaction was carried out as described in Example 26 except that methyl 4-(3-methyl-2-butenyloxy)-3-methoxybenzoate was used in place of methyl 3,5-bis(3-methyl-2-butenyloxy)benzoate, to obtain 4-(4-(3-methyl-2-butenyloxy)-3-methoxybenzoylamino)pentafluorosulfanylbenzene 0.85 g (yield 49%).

Herein, 4-(4-(3-methyl-2-butenyloxy)-3-methoxybenzoylamino)pentafluorosulfanylbenzene is a novel compound having the following property values.

$^1$H-NMR (CDCl$_3$, δ (ppm)); 1.76 (3H, s), 1.79 (3H, s), 3.94 (3H, s), 4.66 (2H, d, J=6.8 Hz), 5.51 (1H, m), 6.92 (1H, d, J=8.3 Hz), 7.25-7.40 (1H, m), 7.48 (1H, d, J=2.0 Hz), 7.70-7.79 (4H, m), 7.92 (1H, bs)

MS (ES+); 438 (M+1)

Example 28 Synthesis of Compound 28

(Z=NH, p=0, n=11, m=2; Synthesis of 4-(4-(2-propenyloxy)-3-methoxybenzoylamino)pentafluorosulfanylbenzene)

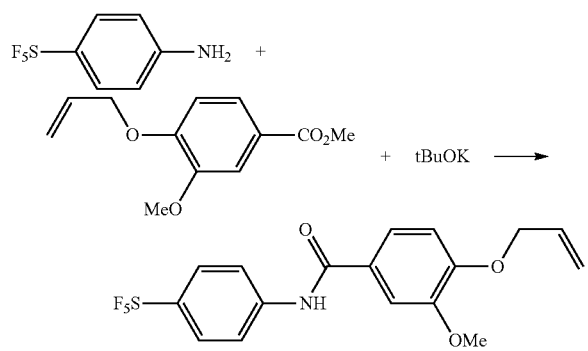

A reaction was carried out as described in Example 26 except that methyl 4-(2-propenyloxy)-3-methoxybenzoate was used in place of methyl 3,5-bis(3-methyl-2-butenyloxy)benzoate, to obtain 4-(4-(2-propenyloxy)-3-methoxybenzoylamino)pentafluorosulfanylbenzene 4.84 g (yield 72%).

Herein, 4-(4-(2-propenyloxy)-3-methoxybenzoylamino)pentafluorosulfanylbenzene is a novel compound having the following property values.

$^1$H-NMR (CDCl$_3$, δ (ppm)); 3.94 (3H, s), 4.65-4.71 (2H, m), 6.01-6.15 (1H, m), 6.91 (1H, d, J=8.4 Hz), 7.32-7.39 (1H, m), 7.70-7.79 (4H, m), 7.97 (1H, bs)

MS (ES+); 410 (M+1)

Example 29 Synthesis of Compound 29

(Z=NH, p=0, n=11, m=3; Synthesis of 4-(2,3,4-tris(3-methyl-2-butenyloxy)benzoylamino)pentafluorosulfanylbenzene)

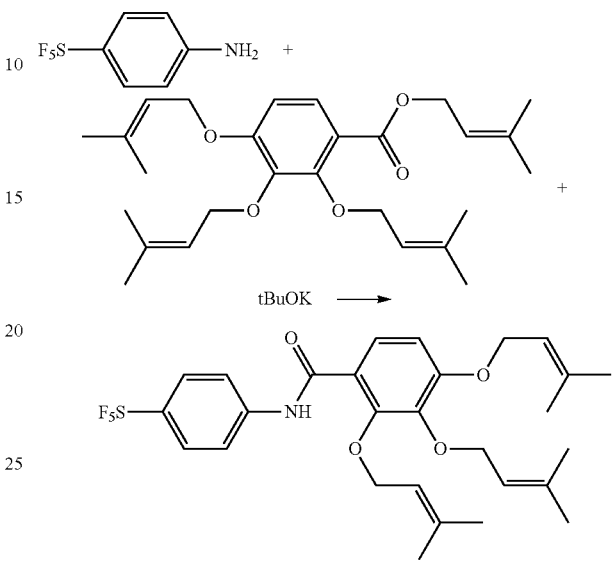

A reaction was carried out as described in Example 26 except that prenyl 2,3,4-tris(3-methyl-2-butenyloxy)benzoate was used in place of methyl 3,5-bis(3-methyl-2-butenyloxy)benzoate, to obtain 4-(2,3,4-tris(3-methyl-2-butenyloxy)benzoylamino)pentafluorosulfanylbenzene 3.46 g (yield 60%).

Herein, 4-(2,3,4-tris(3-methyl-2-butenyloxy)benzoylamino)pentafluorosulfanylbenzene is a novel compound having the following property values.

1H-NMR (CDCl$_3$, δ (ppm)); 1.60-1.72 (18H, m), 4.54 (2H, d, J=7.4 Hz), 4.63 (2H, d, J=6.7 Hz), 4.79 (2H, d, J=7.7 Hz), 5.47-5.66 (3H, m), 6.81 (1H, d, J=9.0 Hz), 7.68-7.79 (4H, m), 7.97 (1H, d, J=8.9 Hz), 10.60 (1H, bs)

MS (ES−); 574 (M−1)

Example 30 Synthesis of Compound 30

(Z=NH, p=0, n=1, m=2; Synthesis of 4-(4-hydroxy-5-(2-propenyl)-3-methoxybenzoylamino)pentafluorosulfanylbenzene)

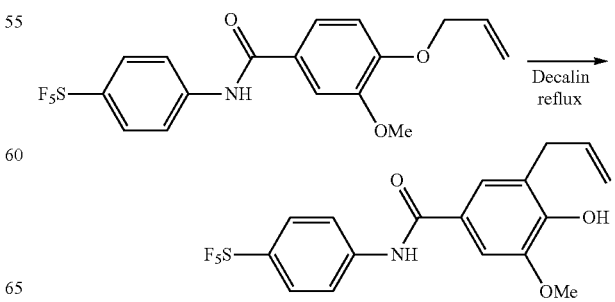

Into a 100 ml flask equipped with a stirrer and a thermometer, 1.90 g (4.64 mmol) of Compound 28 and 40 ml of decalin were added, and refluxed for 5 hours.

After completion of the reaction, 2 g of diatomaceous earth was added, and the reaction mixture was concentrated under reduced pressure. The obtained concentrate was purified by a reversed-phase type column chromatography (eluent; acetonitrile/water=0/100 to 7/3 (volume ratio)), to obtain 4-(4-hydroxy-5-(2-propenyl)-3-methoxybenzoylamino)pentafluorosulfanylbenzene 0.62 g (yield; 33%) as white powder.

Herein, 4-(4-hydroxy-5-(2-propenyl)-3-methoxybenzoylamino)pentafluorosulfanylbenzene is a novel compound having the following property values.

$^1$H-NMR (CD$_3$CN$_3$, δ (ppm)); 2.15 (1H, bs), 3.42 (2H, d, J=6.5 Hz), 3.95 (3H, s), 5.02-5.13 (2H, m), 5.96-6.10 (1H, m), 7.47 (2H, d, J=1.6 Hz), 7.77-7.94 (4H, m), 8.90 (1H, bs)
MS (ES+); 410 (M+1)

Example 31 Synthesis of Compound 31

(Z=NH, p=1, n=11, q=0; Synthesis of 4-acryloylaminopentafluorosulfanylbenzene)

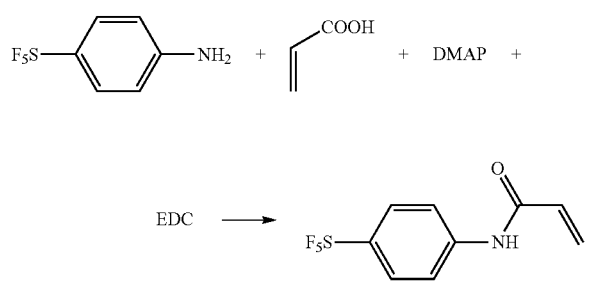

Into a 100 ml flask equipped with a stirrer and a thermometer, 10 ml of methylene chloride, 3.0 g (13.7 mmol) of 4-aminopentafluorosulfanylbenzene, 200 mg of DMAP, 1.48 g (20.5 mmol) of acrylic acid were added, subsequently methylene chloride solution (10 ml) containing 3.41 g (17.8 mmol) of EDC was added over 15 minutes at room temperature, and stirred for 5 hours at the same temperature. The reaction mixture was concentrated under reduced pressure, to which 100 ml of ethyl acetate was added, and the organic phase was washed with saturated saline. The organic phase was dried over magnesium sulfate, and concentrated under reduced pressure. The obtained residue was subjected to a silica-gel column chromatography (solvent; hexane-ethyl acetate=5:1 v/v), to 4-acryloylaminopentafluorosulfanylbenzene 3.1 g (yield 83%) as white powder.

Herein, the obtained 4-acryloylaminopentafluorosulfanylbenzene is a novel compound having the following property values.

$^1$H-NMR (CDCl$_3$, δ (ppm)); 5.85 (1H, dd, J=1.2, 10 Hz), 6.25 (1H, dd, J=10.3, 17.0 Hz), 6.49 (1H, dd, J=1.0, 17.0 Hz), 7.42 (1H, bs), 7.65-7.75 (4H, m). UV absorption spectrum (acetonitrile-H$_2$O, λmax (nm)); 265
MS (ES−); 272 (M−1)

Example 32 Synthesis of Compound 32

(Z=NH, p=1, n=11, q=0; Synthesis of 3-acryloylaminopentafluorosulfanylbenzene)

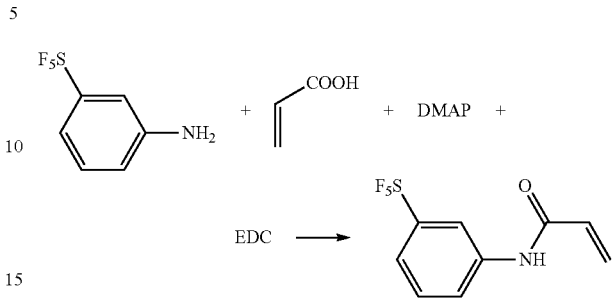

Into a 100 ml flask equipped with a stirrer and a thermometer, 10 ml of methylene chloride, 200 mg of DMAP, 3.14 g (16.4 mmol) of EDC and 1.28 g (17.8 mmol) of acrylic acid were added, subsequently methylene chloride solution (10 ml) containing 3.0 g (13.7 mmol) of 4-aminopentafluorosulfanylbenzene was added over 15 minutes at room temperature, and stirred for 5 hours at the same temperature. The reaction mixture was concentrated under reduced pressure, to which 100 ml of ethyl acetate was added, and the organic phase was washed with saturated saline. The organic phase was dried over magnesium sulfate, and concentrated under reduced pressure. The obtained residue was subjected to a silica-gel column chromatography (solvent; hexane-ethyl acetate=5:1 v/v), to obtain 3-acryloylaminopentafluorosulfanylbenzene 3.2 g (yield 86%) as white powder.

Herein, the obtained 3-acryloylaminopentafluorosulfanylbenzene is a novel compound having the following property values.

$^1$H-NMR (CDCl$_3$, δ (ppm)); 5.84 (1H, dd, J=1.2, 10 Hz), 6.25 (1H, dd, J=10.2, 17.0 Hz), 6.48 (1H, dd, J=1.2, 17.0 Hz)
UV absorption spectrum (acetonitrile-H$_2$O, λmax (nm)); 264
MS (ES−); 272 (M−1)

Example 33 Synthesis of Compound 33

(Z=NH, p=0, n=11, q=1; Synthesis of 4-(5-hydroxymethylfuran-2-yl)carbonylaminopentafluorosulfanylbenzene)

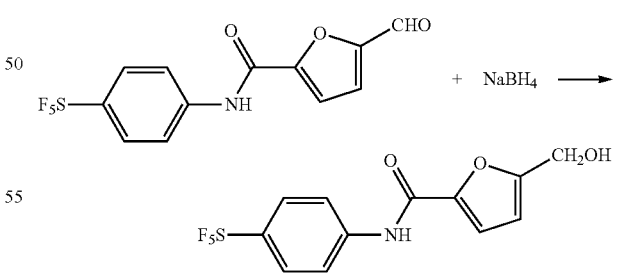

Into a 100 ml flask equipped with a stirrer and a thermometer, 10 ml of THF, 1.10 g (3.22 mmol) of 5-formylfuran-2-ylcarbonylaminopentafluorosulfanylbenzene was added, and subsequently 0.13 g (3.54 mmol) of sodium borohydride was added gradually little by little, and stirred for 3 hours at room temperature.

After completion of the reaction, 30 ml of ethyl acetate and 5 ml of water were added, subsequently 1 ml of 1N hydrochloric acid was gradually added while stirring, and further stirred for 15 minutes. The reaction mixture was subjected to liquid-separation. The obtained organic phase was washed with saturated saline, and dried over magnesium sulfate. The organic phase was concentrated under reduced pressure, and the obtained residue was subjected to a reversed-phase type column chromatography (eluent: acetonitrile-water=0/100 to 70/30 (volume ratio)), to obtain 4-(5-hydroxymethylfuran-2-yl)carbonylaminopentafluorosulfanylbenzene 0.39 g (yield 35%) as white powder.

Herein, the obtained 4-(5-hydroxymethylfuran-2-yl)carbonylaminopentafluorosulfanylbenzene is a novel compound having the following property values.

$^1$H-NMR (DMSO-d$_6$, δ (ppm)); 4.51 (2H, d, J=5.8 Hz), 5.46 (1H, t, J=5.8 Hz), 6.54 (1H, d, J=3.4 Hz), 7.37 (1H, d, J=3.4 Hz), 7.84-8.00 (4H, m), 10.49 (1H, s)

MS (ES+); 344 (M+1).

Example 34 Synthesis of Compound 34

(Z=O, p=0, n=11, m=2; Synthesis of 4-(4-(3-methyl-2-butenyloxy)-3-methoxybenzoyloxy)pentafluorosulfanylbenzene)

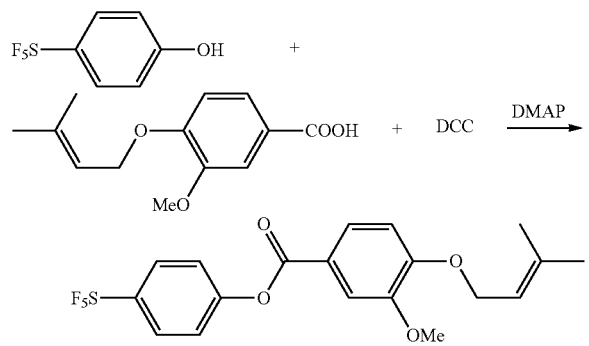

Into a 100 ml flask equipped with a stirrer, a reflux condenser and a thermometer, 1.67 g (7.59 mmol) of 4-hydroxypentafluorosulfanylbenzene, 1.79 g (7.59 mmol) of 4-(3-methyl-2-butenyloxy)-3-methoxybenzoic acid, 1.72 g (8.35 mmol) of DCC, 0.93 g (7.59 mmol) of DMAP and 20 ml of methylene chloride were added, and the reaction was carried out for 4 hours at 40° C. with stirring.

After completion of the reaction, 2 g of diatomaceous earth was added, and the reaction mixture was concentrated under reduced pressure. The obtained residue was purified by a silica-gel column chromatography (eluent; hexane/ethyl acetate=100/0 to 80/20 (volume ratio)), to obtain 4-(4-(3-methyl-2-butenyloxy)-3-methoxybenzoyloxy)pentafluorosulfanylbenzene 1.23 g (yield; 37%) as white needle crystal.

Herein, 4-(4-(3-methyl-2-butenyloxy)-3-methoxybenzoyloxy)pentafluorosulfanylbenzene is a novel compound having the following property values.

$^1$H-NMR (CDCl$_3$, δ (ppm)); 1.77 (3H, s), 1.80 (3H, s), 3.95 (3H, s), 4.69 (2H, d, J=6.8 Hz), 5.50-5.56 (1H, m), 6.96 (1H, d, J=8.5 Hz), 7.32 (2H, d, J=8.9 Hz), 7.64 (1H, d, J=2.0 Hz), 7.80-7.86 (3H, m)

MS (ES−); 437 (M−1)

Example 35 Synthesis of Compound 35

(Z=NH, p=1, n=1, m=0; Synthesis of 4-(cinnamoylamino)pentafluorosulfanylbenzene)

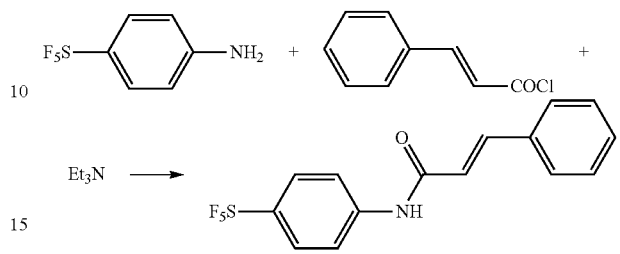

Into a 100 ml flask equipped with a stirrer and a thermometer, 1.00 g (4.56 mmol) of 4-aminopentafluorosulfanylbenzene, 10 ml of methylene chloride and 0.84 g (5.02 mmol) of cinnamoyl chloride were added while cooling with an ice-water bath, and 0.69 g (6.84 mmol) of triethylamine was gradually added dropwise while stirring, and stirred for 6 hours at room temperature.

After completion of the reaction, 30 ml of methylene chloride was added, and the reaction mixture was washed with 30 ml of water and subsequently 30 ml of saturated aqueous solution of sodium bicarbonate. The organic phase was dried over magnesium sulfate, and concentrated under reduced pressure. The obtained residue was purified by a silica-gel column chromatography (eluent; n-hexane/ethyl acetate=3/1 (volume ratio)), to obtain 4-(cinnamoylamino)pentafluorosulfanylbenzene 0.33 g (yield; 21%) as yellowish foam.

Herein, 4-(cinnamoylamino)pentafluorosulfanylbenzene is a novel compound having the following property values.

$^1$H-NMR (CDCl$_3$, δ (ppm)); 6.55 (1H, d, J=15.5 Hz), 7.29-7.60 (6H, m), 7.73 (4H, s), 7.79 (1H, d, J=15.5 Hz)

MS (ES+); 350 (M+1)

Example 36 Synthesis of Compound 36

(Z=O, p=1, n=1, m=0; Synthesis of 4-(cinnamoyloxy)pentafluorosulfanylbenzene)

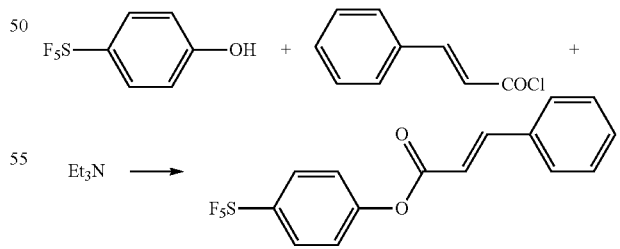

A reaction was carried out as described in Example 35 except that 4-hydroxypentafluorosulfanylbenzene was used in place of 4-aminopentafluorosulfanylbenzene, to obtain 4-(cinnamoyloxy)pentafluorosulfanylbenzene 0.91 g (yield 57%).

Herein, 4-(cinnamoyloxy)pentafluorosulfanylbenzene is a novel compound having the following property values.

¹H-NMR (CDCl₃, δ (ppm)); 6.63 (1H, d, J=16.0 Hz), 7.29 (2H, bd), 7.42-7.46 (3H, m), 7.58-7.62 (2H, m), 7.79-7.84 (2H, m), 7.90 (1H, d, J=16.0 Hz)

MS (ES+); 391 (M+CH₃CN)

Example 37 Synthesis of Compound 37

(Z=NH, p=1, n=1, m=2; Synthesis of 4-(4-(3-methyl-2-butenyloxy)-3-methoxycinnamoylamino)pentafluorosulfanylbenzene)

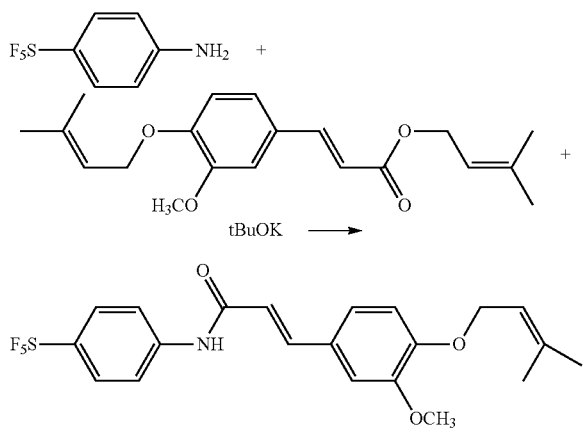

A reaction was carried out as described in Example 26 except that prenyl 4-(3-methyl-2-butenyloxy)-3-methoxycinnamate was used in place of methyl 3,5-bis(3-methyl-2-butenyloxy)benzoate, to obtain 4-(4-(3-methyl-2-butenyloxy)-3-methoxycinnamoylamino)pentafluorosulfanylbenzene 0.44 g (yield 21%).

Herein, 4-(4-(3-methyl-2-butenyloxy)-3-methoxycinnamoylamino)pentafluorosulfanylbenzene is a novel compound having the following property values.

¹H-NMR (CDCl₃, δ (ppm)); 1.75 (3H, s), 1.76 (3H, s), 3.90 (3H, s), 4.63 (2H, d, J=6.8 Hz), 5.48-5.55 (1H, m), 6.40 (1H, d, =15.4 Hz), 6.88 (1H, d, J=8.4 Hz), 7.05 (1H, d, J=1.9 Hz), 7.11 (1H, dd, J=8.4, 1.9 Hz), 7.47 (1H, bs), 7.69-7.77 (5H, m)

MS (ES+); 464 (M+1)

Example 38 Synthesis of Compound 38

(Z=NH, p=1, n=11, m=2; Synthesis of 4-(4-(2-propenyloxy)-3-methoxycinnamoylamino)pentafluorosulfanylbenzene)

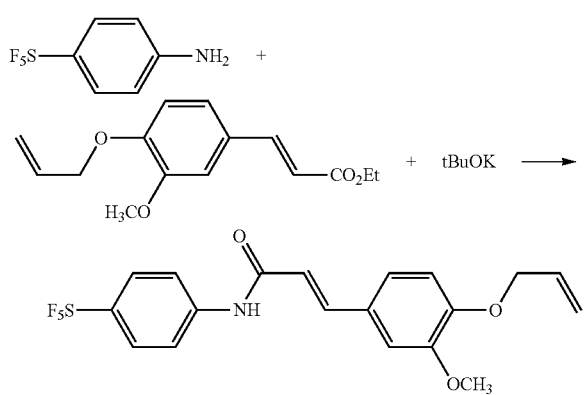

A reaction was carried out as described in Example 26 except that ethyl 4-(2-propenyloxy)-3-methoxycinnamate was used in place of Methyl 3,5-bis(3-methyl-2-butenyloxy)benzoate, to obtain 4-(4-(2-propenyloxy)-3-methoxycinnamoylamino)pentafluorosulfanylbenzene 0.85 g (yield 17%).

Herein, 4-(4-(2-propenyloxy)-3-methoxycinnamoylamino)pentafluorosulfanylbenzene is a novel compound having the following property values.

¹H-NMR (CDCl₃, δ (ppm)); 3.92 (3H, s), 4.63-4.69 (2H, m), 5.29-5.47 (2H, m), 6.01-6.15 (1H, m), 6.41 (1H, d, J=15.3 Hz), 6.88 (1H, d, J=8.3 Hz), 7.04-7.14 (2H, m), 7.45 (1H, bs), 7.69-7.77 (5H, m)

MS (ES+); 436 (M+1)

Example 39 Synthesis of Compound 39

(Z=NH, p=1, n=11, m=2; Synthesis of 4-(3,4-bis(3-methyl-2-butenyloxy)cinnamoylamino)pentafluorosulfanylbenzene)

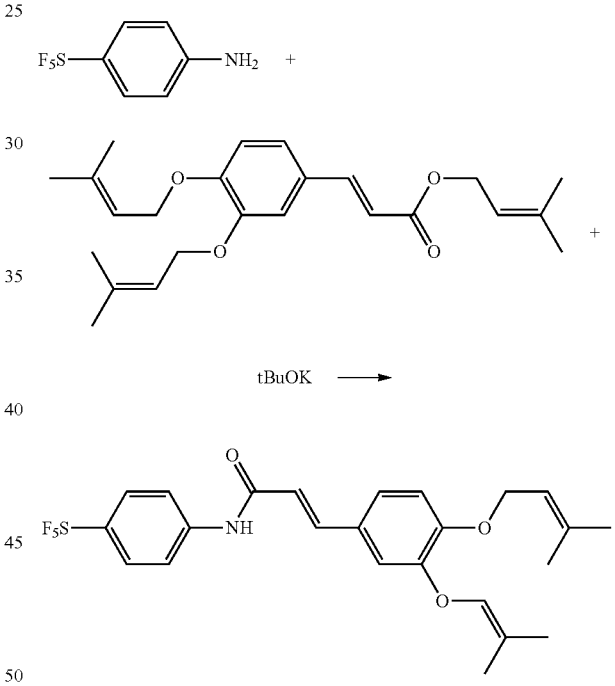

A reaction was carried out as described in Example 26 except that prenyl 3,4-bis(3-methyl-2-butenyloxy)cinnamate was used in place of methyl 3,5-bis(3-methyl-2-butenyloxy)benzoate, to obtain 4-(3,4-bis(3-methyl-2-butenyloxy)cinnamoylamino)pentafluorosulfanylbenzene 0.69 g (yield 17%).

Herein, 4-(3,4-bis(3-methyl-2-butenyloxy)cinnamoylamino)pentafluorosulfanylbenzene is a novel compound having the following property values.

¹H-NMR (CDCl₃, δ (ppm)); 1.54-1.80 (12H, m), 4.62 (4H, t, J=7.4 Hz), 5.46-5.56 (2H, m), 6.37 (1H, d, J=15.3 Hz), 6.88 (1H, d, J=8.3 Hz), 7.06-7.26 (2H, m), 7.41 (1H, bs), 7.68-7.77 (5H, m)

MS (ES-); 516 (M-1)

Example 40 Synthesis of Compound 40

(Z=NH, p=1, n=11, m=2; Synthesis of 4-(2,4-bis(3-methyl-2-butenyloxy)cinnamoylamino)pentafluorosulfanylbenzene)

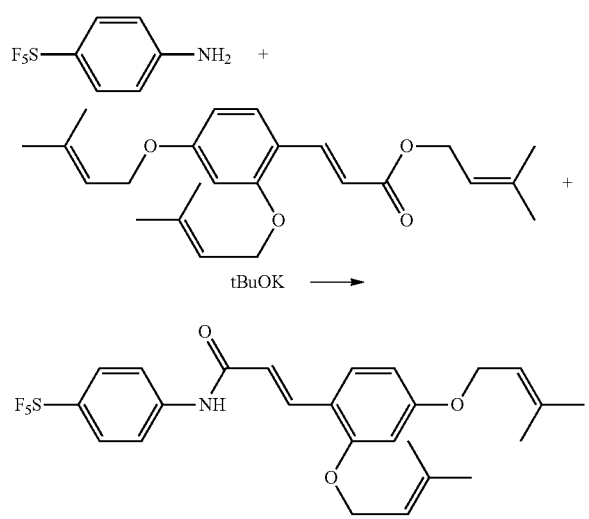

A reaction was carried out as described in Example 26 except that prenyl 2,4-bis(3-methyl-2-butenyloxy)cinnamate was used in place of methyl 3,5-bis(3-methyl-2-butenyloxy)benzoate, to obtain 4-(2,4-bis(3-methyl-2-butenyloxy)cinnamoylamino)pentafluorosulfanylbenzene 0.53 g (yield 30%).

Herein, 4-(2,4-bis(3-methyl-2-butenyloxy)cinnamoylamino)pentafluorosulfanylbenzene is a novel compound having the following property values.

$^1$H-NMR (CDCl$_3$, δ (ppm)); 1.75, 1.76, 1.81 (12H, 3s), 4.52-4.61 (4H, m), 5.45-5.56 (2H, m), 6.48-6.60 (3H, m), 7.36 (1H, bs), 7.43 (1H, d, J=8.3 Hz), 7.72 (4H, s), 7.99 (1H, d, J=15.6 Hz)

MS (ES−); 516 (M−1)

Example 41 Synthesis of Compound 41

(Z=NH, p=1, n=1, m=2; Synthesis of 4-(3-(3-methyl-2-butenyloxy)-4-methoxycinnamoylamino)pentafluorosulfanylbenzene)

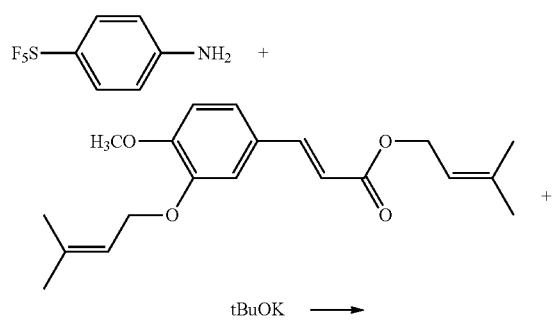

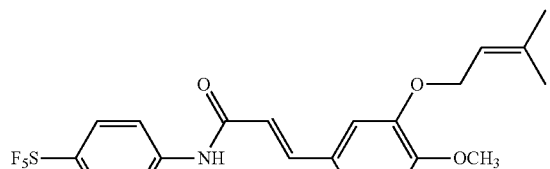

A reaction was carried out as described in Example 26 except that prenyl 3-(3-methyl-2-butenyloxy)-4-methoxycinnamate was used in place of methyl 3,5-bis(3-methyl-2-butenyloxy)benzoate, to obtain 4-(3-(3-methyl-2-butenyloxy)-4-methoxycinnamoylamino)pentafluorosulfanylbenzene 0.68 g (yield 16%).

Herein, 4-(3-(3-methyl-2-butenyloxy)-4-methoxycinnamoylamino)pentafluorosulfanylbenzene is a novel compound having the following property values.

$^1$H-NMR (CDCl$_3$, δ (ppm)); 1.76 (3H, s), 1.79 (3H, s), 3.91 (3H, s), 4.58-4.64 (2H, m), 5.50-5.57 (1H, m), 6.39 (1H, d, J=15.4 Hz), 6.88 (1H, d, J=8.3 Hz), 7.08 (1H, d, J=2.0 Hz), 7.14 (1H, d, J=2.0 Hz), 7.45 (1H, bs), 7.68-7.77 (5H, m)

MS (ES+); 464 (M+1)

Example 42 Synthesis of Compound 42

(Z=NH, p=1, n=1, m=2; Synthesis of 4-(4-(2-butenyloxy)-3-methoxycinnamoylamino)pentafluorosulfanylbenzene)

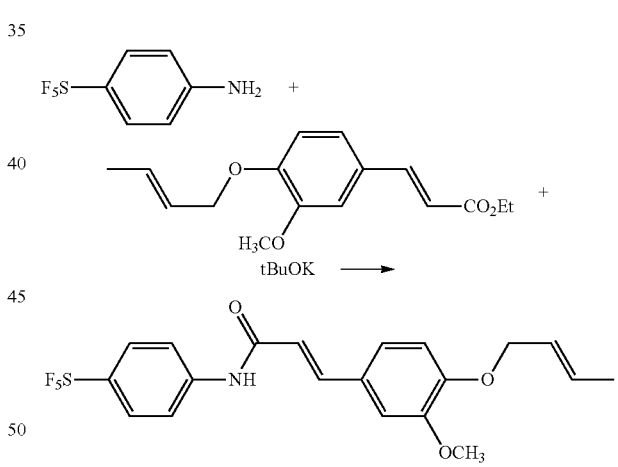

A reaction was carried out as described in Example 26 except that ethyl 4-(2-butenyloxy)-3-methoxycinnamate was used in place of methyl 3,5-bis(3-methyl-2-butenyloxy)benzoate, to obtain 4-(4-(2-butenyloxy)-3-methoxycinnamoylamino)pentafluorosulfanylbenzene 0.73 g (yield 16%).

Herein, 4-(4-(2-butenyloxy)-3-methoxycinnamoylamino)pentafluorosulfanylbenzene is a novel compound having the following property values.

1H-NMR (CDCl$_3$, δ (ppm)); 1.75 (3H, m), 3.91 (3H, s), 4.57+4.72 (2H, 2d), 5.72-5.93 (2H, m), 6.40 (1H, d, J=15.3 Hz), 6.88 (1H, d, J=8.3 Hz), 7.03-7.13 (2H, m), 7.45 (1H, bs), 7.69-7.76 (5H, m) MS (ES+); 450 (M+1)

Example 43 Synthesis of Compound 43

(Z=NH, p=1, n=1, m=3; Synthesis of 4-(4-(3-methyl-2-butenyloxy)-3,5-dimethoxycinnamoylamino)pentafluorosulfanylbenzene)

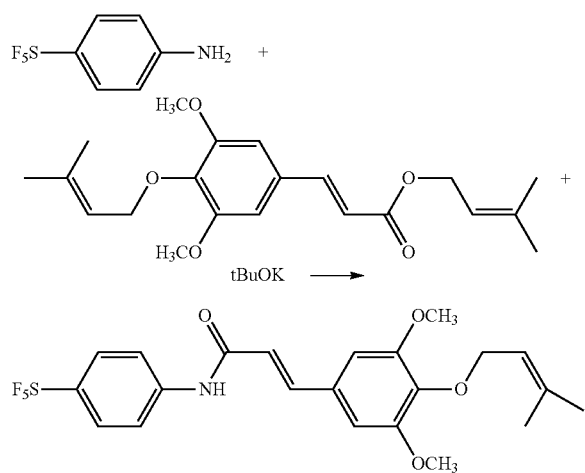

A reaction was carried out as described in Example 26 except that prenyl 4-(3-methyl-2-butenyloxy)-3,5-dimethoxycinnamate was used in place of methyl 3,5-bis(3-methyl-2-butenyloxy)benzoate, to obtain 4-(4-(3-methyl-2-butenyloxy)-3,5-dimethoxycinnamoylamino)pentafluorosulfanylbenzene 1.15 g (yield 19%).

Herein, 4-(4-(3-methyl-2-butenyloxy)-3,5-dimethoxycinnamoylamino)pentafluorosulfanylbenzene is a novel compound having the following property values.

$^1$H-NMR (CDCl$_3$, δ (ppm)); 1.68 (3H, s), 1.74 (3H, s), 3.87 (6H, s), 4.55 (2H, d, J=7.3 Hz), 5.52-5.60 (1H, m), 6.46 (1H, d, J=15.4 Hz), 6.76 (2H, s), 7.57 (1H, bs), 7.66-7.75 (5H, m)

MS (ES+); 494 (M+1)

Example 44 Synthesis of Compound 44

(Z=NH, p=1, n=1, m=2; Synthesis of 4-(4-(1-methyl-2-propenyloxy)-3-methoxycinnamoylamino)pentafluorosulfanylbenzene)

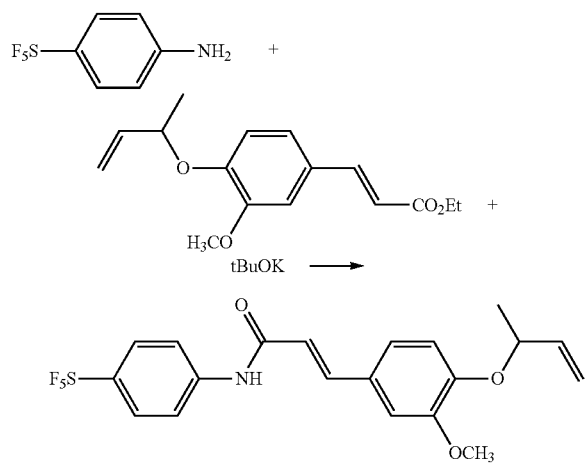

A reaction was carried out as described in Example 26 except that ethyl 4-(1-methyl-2-propenyloxy)-3-methoxycinnamate was used in place of methyl 3,5-bis(3-methyl-2-butenyloxy)benzoate, to obtain 4-(4-(1-methyl-2-propenyloxy)-3-methoxycinnamoylamino)pentafluorosulfanylbenzene 0.95 g (yield 29%).

Herein, 4-(4-(1-methyl-2-propenyloxy)-3-methoxycinnamoylamino)pentafluorosulfanylbenzene is a novel compound having the following property values.

$^1$H-NMR (CDCl$_3$, δ (ppm)); 1.51 (3H, d, J=6.4 Hz), 3.89 (3H, s), 4.80-4.90 (1H, m), 5.19 (1H, m), 5.28 (1H, m), 5.87-5.99 (1H, m), 6.40 (1H, d, J=15.3 Hz), 6.90 (1H, d, J=8.3 Hz), 7.03-7.11 (2H, m), 7.47 (1H, bs), 7.68-7.76 (5H, m)

MS (ES+); 450 (M+1)

Example 45 Synthesis of Compound 45

(Z=NH, p=0, n=11, m=2; Synthesis of 4-(4-hydroxy-3-methoxybenzoylamino)pentafluorosulfanylbenzene)

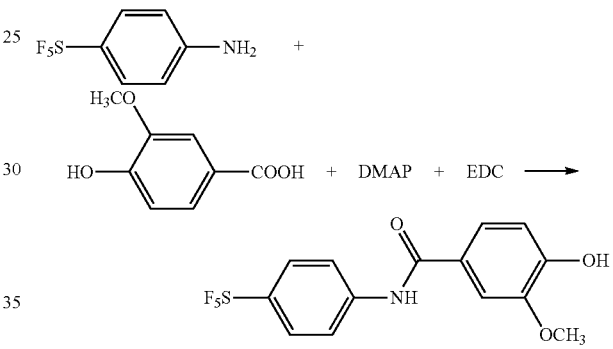

A reaction was carried out as described in Example 10 except that 4-hydroxy-3-methoxybenzoic acid and 4-aminopentafluorosulfanylbenzene were used in place of 3,4,5-tribenzyloxybenzoic acid and 3-aminopentafluorosulfanylbenzene, to obtain 4-(4-hydroxy-3-methoxybenzoylamino)pentafluorosulfanylbenzene 0.20 g (yield 10%).

Herein, 4-(4-hydroxy-3-methoxybenzoylamino)pentafluorosulfanylbenzene is a novel compound having the following property values.

$^1$H-NMR (DMSO-d$_6$, δ (ppm)); 3.86 (3H, s), 6.89 (1H, d, J=8.8 Hz), 7.50-7.56 (2H, m), 7.88 (2H, d, J=9.3 Hz), 7.99 (2H, d, J=9.1 Hz), 9.9 (1H, bs), 10.39 (1H, s)

MS (ES+); 370 (M+1)

Example 46 Synthesis of Compound 46

(Z=NH, p=1, n=11, m=2; Synthesis of 4-(4-hydroxy-5-(2-propenyl)-3-methoxycinnamoylamino)pentafluorosulfanylbenzene)

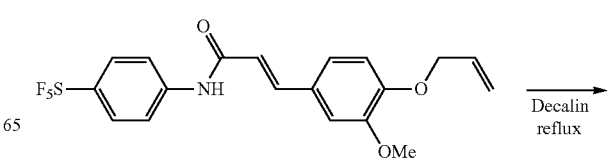

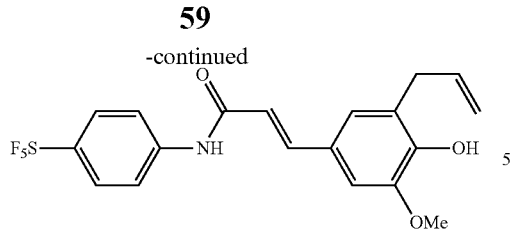

A reaction was carried out as described in Example 30 except that 4-(2-propenyloxy-3-methoxy)cinnamoylaminopentafluorosulfanylbenzene was used in place of 4-(2-propenyloxy-3-methoxy)benzoylaminopentafluorosulfanylbenzene, to obtain 4-(4-hydroxy-5-(2-propenyl)-3-methoxycinnamoylamino)pentafluorosulfanylbenzene 0.28 g (yield 20%).

Herein, 4-(4-hydroxy-5-(2-propenyl)-3-methoxycinnamoylamino)pentafluorosulfanylbenzene is a novel compound having the following property values.

$^1$H-NMR (CDCl$_3$, δ (ppm)); 3.42 (2H, d, J=6.7 Hz), 3.92 (3H, s), 5.07-5.15 (2H, m), 5.92-6.05 (2H, m), 6.39 (1H, d, J=15.4 Hz), 6.92 (1H, d, J=1.9 Hz), 7.02 (1H, d, J=1.8 Hz), 7.44 (1H, bs), 7.65-7.76 (5H, m)

MS (ES+); 436 (M+1)

Example 47 Synthesis of Compound 47

(Z=NH, p=1, n=1, m=2; Synthesis of 4-(4-hydroxy-5-(2-butenyl)-3-methoxycinnamoylamino)pentafluorosulfanylbenzene)

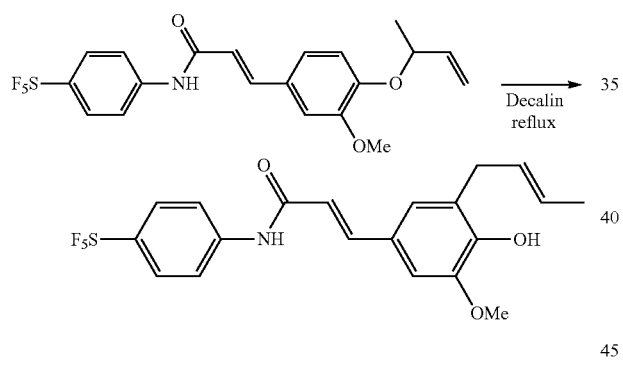

A reaction was carried out as described in Example 30 except that 4-(1-methylallyloxy-3-methoxy)cinnamoylaminopentafluorosulfanylbenzene was used in place of 4-(2-propenyloxy-3-methoxy)benzoylaminopentafluorosulfanylbenzene, to obtain 4-(4-hydroxy-5-(2-butenyl)-3-methoxycinnamoylamino)pentafluorosulfanylbenzene 40 mg (yield 6%).

Herein, 4-(4-hydroxy-5-(2-propenyl)-3-methoxycinnamoylamino)pentafluorosulfanylbenzene is a novel compound having the following property values.

MS (ES+); 450 (M+1)

Example 48 Synthesis of Compound 48

(Z=NH, p=0, n=11, m=1; Synthesis of 4-(3-(1,1-dimethyl-2-propenyloxy)benzoylamino)pentafluorosulfanylbenzene)

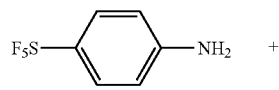

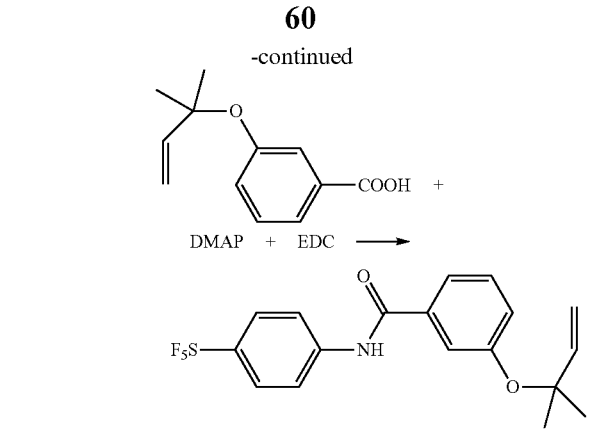

A reaction was carried out as described in Example 45 except that 1,1-dimethyl-2-propenyloxybenzoic acid was used in place of 4-hydroxy-3-methoxybenzoic acid, to obtain 4-(3-(1,1-dimethyl-2-propenyloxy)benzoylamino)pentafluorosulfanylbenzene 0.16 g (yield 5%).

Herein, 4-(3-(1,1-dimethyl-2-propenyloxy)benzoylamino)pentafluorosulfanylbenzene is a novel compound having the following property values.

1H-NMR (DMSO-d$_6$, δ (ppm)); 3.42 (2H, d, J=6.7 Hz), 3.92 (3H, s), 5.07-5.15 (2H, m), 5.92-6.05 (2H, m), 6.39 (1H, d, J=15.4 Hz), 6.92 (1H, d, J=1.9 Hz), 7.02 (1H, d, J=1.8 Hz), 7.44 (1H, bs), 7.65-7.76 (5H, m)

MS (ES+); 408 (M+1)

Example 49 Synthesis of Compound 49

(Z=NH, p=0, n=11, m=3; Synthesis of 4-(2,3,4-trihydroxybenzoylamino)pentafluorosulfanylbenzene)

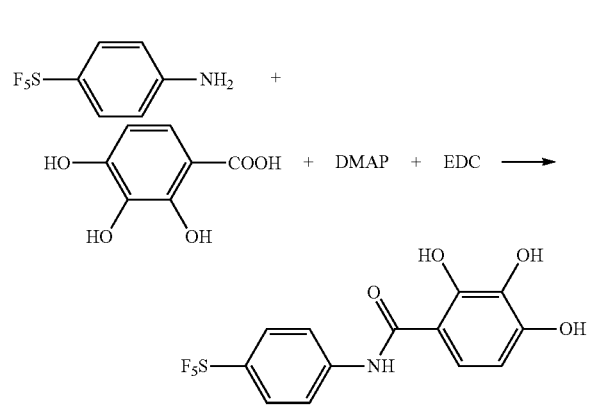

A reaction was carried out as described in Example 2 except that 2,3,4-trihydroxybenzoic acid was used in place of 3,4,5-tribenzyloxybenzoic acid, to obtain 4-(2,3,4-trihydroxybenzoylamino)pentafluorosulfanylbenzene 0.12 g (yield 3%).

Herein, 4-(2,3,4-trihydroxybenzoylamino)pentafluorosulfanylbenzene is a novel compound having the following property values.

$^1$H-NMR (CDCl$_3$, δ (ppm)); 6.43 (1H, d, J=8.8 Hz), 7.44 (1H, d, J=8.9 Hz), 7.86-7.96 (4H, m), 8.65 (1H, bs), 9.80 (1H, bs), 10.50 (1H, s), 11.85 (1H, bs) MS (ES+); 372 (M+1)

Example 50: Synthesis of Compound 51

(Z=NH, p=1, n=1, m=2; Synthesis of 4-(2,4-dihydroxycinnamoylamino)pentafluorosulfanylbenzene)

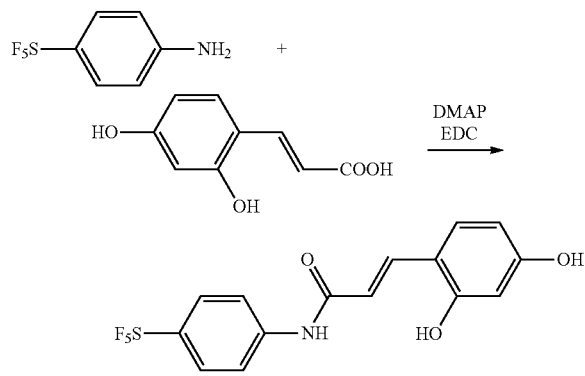

A reaction was carried out as described in Example 20 except that 2,4-dihydroxycinnamic acid was used in place of 4-acetoxy-3-methoxycinnamic acid, to obtain 4-(2,4-dihydroxycinnamoylamino)pentafluorosulfanylbenzene 0.33 g (yield 8%).

Herein, 4-(2,4-dihydroxycinnamoylamino)pentafluorosulfanylbenzene is a novel compound having the following property values.

$^1$H-NMR (DMSO-d$_6$, δ (ppm)); 6.30 (1H, dd, J=2.3, 8.4 Hz), 6.39 (1H, d, J=2.4 Hz), 6.71 (1H, d, J=15.7 Hz), 7.30 (1H, d, J=8.5 Hz), 7.72 (1H, d, J=15.7 Hz), 7.81-7.92 (4H, m), 9.84 (1H, bs), 10.14 (1H, bs), 10.45 (1H, s)
MS (ES+); 382 (M+1)

Example 51 Synthesis of Compound 52

(Z=NH, p=1, n=11, m=2; Synthesis of 4-(3-hydroxy-4-methoxycinnamoylamino)pentafluorosulfanylbenzene)

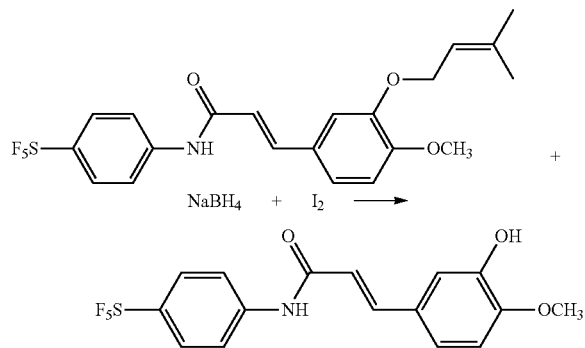

Into a 100 ml flask equipped with a stirrer and a thermometer, 0.42 g (0.906 mmol) of Compound 41 and 10 ml of THF were added while cooling with an ice-water bath, and 45 mg (1.18 mmol) of sodium borohydride was gradually added while stirring. Subsequently, 115 mg (0.453 mmol) of iodine was added, and the mixture was stirred for 1 hour at the same temperature and left overnight.

To the reaction mixture, 1 ml of methanol was added at room temperature and stirred for 2 hours. After 5 ml of 1N hydrochloric acid and subsequently saturated saline were added, extraction was carried out using ethyl acetate. After the organic phase was washed with saturated aqueous solution of sodium bicarbonate and subsequently with saturated saline, the organic phase was dried over magnesium sulfate. The organic phase was concentrated under reduced pressure, and the obtained white powder was washed with tert-butyl methyl ether/n-hexane mixed solvent, to obtain 4-(3-hydroxy-4-methoxycinnamoylamino)pentafluorosulfanylbenzene 0.26 g (yield; 72%).

Herein, 4-(3-hydroxy-4-methoxycinnamoylamino)pentafluorosulfanylbenzene is a novel compound having the following property values.

$^1$H-NMR (CDCl$_3$, δ (ppm)); 3.95 (3H, s), 5.66 (1H, s), 6.37 (1H, d, J=15.3 Hz), 6.87 (1H, d, J=8.5 Hz), 7.06 (1H, d, J=8.5 Hz), 7.17 (1H, s), 7.37 (1H, s), 7.66-7.76 (6H, m)
MS (ES+); 396 (M+1)

Example 52 Synthesis of Compound 53

(Z=NH, p=1, n=11, m=3; Synthesis of 4-(4-hydroxy-3,5-dimethoxycinnamoylamino)pentafluorosulfanylbenzene)

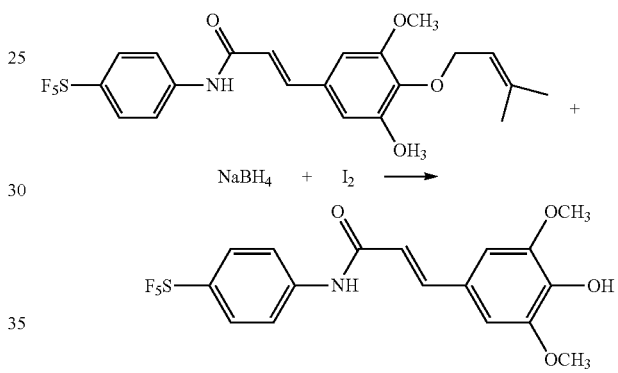

A reaction was carried out as described in Example 51 except that Compound 43 was used in place of Compound 41, to obtain 4-(4-hydroxy-3,5-dimethoxycinnamoylamino)pentafluorosulfanylbenzene 0.33 g (yield 43%).

Herein, 4-(4-hydroxy-3,5-dimethoxycinnamoylamino)pentafluorosulfanylbenzene is a novel compound having the following property values.

$^1$H-NMR (CDCl$_3$, δ (ppm)); 3.94 (6H, s), 5.78 (1H, s), 6.41 (1H, d, J=15.3 Hz), 6.80 (2H, s), 7.41 (1H, bs), 7.66-7.77 (5H, m)
MS (ES+); 426 (M+1)

Example 53 Synthesis of Compound 55

(Z=NH, p=0, n=11, m=3; Synthesis of 4-(2,4,6-trihydroxybenzoylamino)pentafluorosulfanylbenzene)

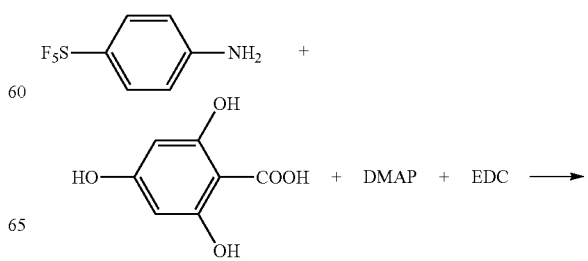

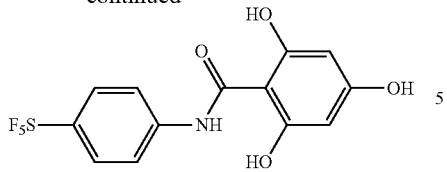

A reaction was carried out as described in Example 20 except that 2,4,6-trihydroxybenzoic acid was used in place of 4-acetoxy-3-methoxycinnamic acid, to obtain 4-(2,4,6-trihydroxybenzoylamino)pentafluorosulfanylbenzene 0.60 g (yield 6%).

Herein, 4-(2,4,6-trihydroxybenzoylamino)pentafluorosulfanylbenzene is a novel compound having the following property values.

$^1$H-NMR (DMSO-$d_6$, δ (ppm)); 5.91 (2H, s), 7.81-7.93 (4H, m), 10.23 (1H, bs), 10.86 (1H, s), 12.47 (2H, bs)

MS (ES+); 372 (M+1)

Example 54 Synthesis of Compound 56

(Z=NH, p=1, n=11, m=2; Synthesis of 4-(3,4-dihydroxycinnamoylamino)pentafluorosulfanylbenzene)

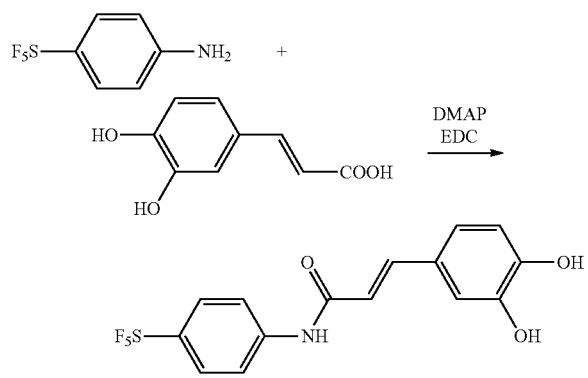

A reaction was carried out as described in Example 20 except that 3,4-dihydroxycinnamic acid was used in place of 4-acetoxy-3-methoxycinnamic acid, to obtain 4-(3,4-dihydroxycinnamoylamino)pentafluorosulfanylbenzene 0.22 g (yield 5%).

Herein, 4-(3,4-dihydroxycinnamoylamino)pentafluorosulfanylbenzene is a novel compound having the following property values.

$^1$H-NMR (DMSO-$d_6$, δ (ppm)); 6.54 (1H, d, J=15.7 Hz), 6.79 (1H, d, J=8.2 Hz), 6.94 (1H, dd, J=1.9, 8.2 Hz), 7.03 (1H, d, J=1.9 Hz), 7.47 (1H, d, J=15.6 Hz), 7.83-7.92 (4H, m), 9.4 (2H, bs), 10.51 (1H, bs)

MS (ES+); 382 (M+1)

Example 55: Synthesis of Compound 57

(Z=NH, p=0, n=1, m=2; Synthesis of 4-(4-hydroxy-3-fluorobenzoylamino)pentafluorosulfanylbenzene)

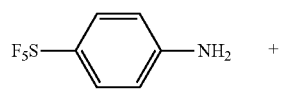

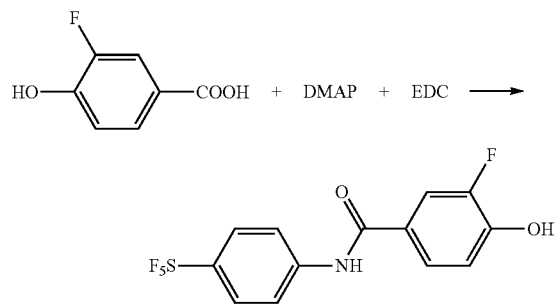

A reaction was carried out as described in Example 2 except that 4-hydroxy-3-fluorobenzoic acid was used in place of 3,4,5-tribenzyloxybenzoic acid, to obtain 4-(4-hydroxy-3-fluorobenzoylamino)pentafluorosulfanylbenzene 0.07 g.

Herein, 4-(4-hydroxy-3-fluorobenzoylamino)pentafluorosulfanylbenzene is a novel compound having the following property values.

$^1$H-NMR (DMSO-$d_6$, δ (ppm)); 7.07 (1H, t, J=8.7 Hz), 7.72 (1H, dd, J=1.6, 8.4 Hz), 7.83 (1H, dd, J=2.3, 12.3 Hz), 7.86-7.92 (2H, m), 7.95-8.02 (2H, m), 10.44 (1H, s), 10.8 (1H, bs)

MS (ES+); 358 (M+1)

Example 56: Synthesis of Compound 58

(Z=NH, p=0, n=1, m=2; Synthesis of 4-(3-hydroxy-4-fluorobenzoylamino)pentafluorosulfanylbenzene)

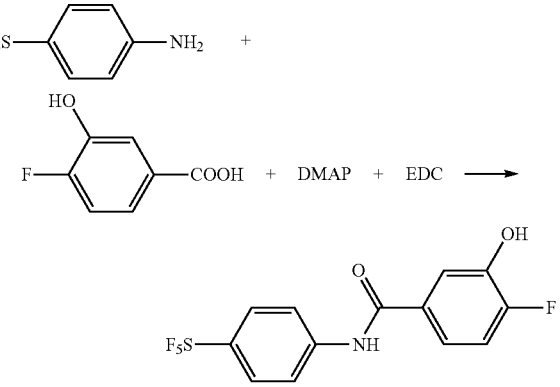

A reaction was carried out as described in Example 2 except that 3-hydroxy-4-fluorobenzoic acid was used in place of 3,4,5-tribenzyloxybenzoic acid, to obtain 4-(3-hydroxy-4-fluorobenzoylamino)pentafluorosulfanylbenzene 0.32 g (yield 20%).

Herein, 4-(3-hydroxy-4-fluorobenzoylamino)pentafluorosulfanylbenzene is a novel compound having the following property values.

$^1$H-NMR (DMSO-$d_6$, δ (ppm)); 7.32 (1H, m), 7.43-7.48 (1H, m), 7.53-7.59 (1H, m), 7.86-8.00 (4H, m), 10.34 (1H, s), 10.58 (1H, s)

MS (ES+); 358 (M+1)

Example 57: Synthesis of Compound 59

(Z=NH, p=0, n=1, m=2; Synthesis of 4-(4-nitro-3-methoxybenzoylamino)pentafluorosulfanylbenzene)

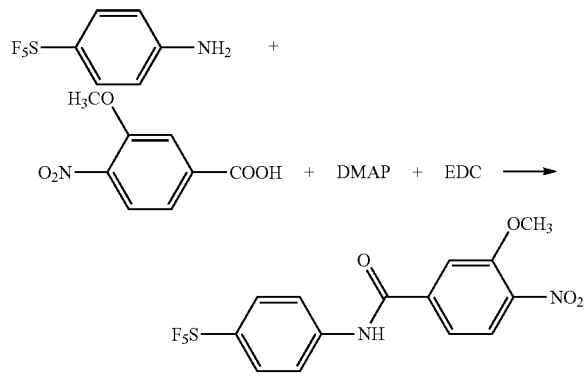

A reaction was carried out as described in Example 2 except that 4-nitro-3-methoxybenzoic acid was used in place of 3,4,5-tribenzyloxybenzoic acid, to obtain 4-(4-nitro-3-methoxybenzoylamino)pentafluorosulfanylbenzene 0.59 g (yield 19%).

Herein, 4-(4-nitro-3-methoxybenzoylamino)pentafluorosulfanylbenzene is a novel compound having the following property values.

$^1$H-NMR (DMSO-$d_6$, δ (ppm)); 4.03 (3H, s), 7.68 (1H, dd, J=1.6, 8.4 Hz), 7.83 (1H, d, J=1.5 Hz), 7.92-8.02 (4H, m), 8.05 (1H, d, J=8.4 Hz), 10.85 (1H, s)

MS (ES−); 397 (M−1)

Example 58: Synthesis of Compound 60

(Z=NH, p=0, n=1, m=2; Synthesis of 4-(4-amino-3-methoxybenzoylamino)pentafluorosulfanylbenzene)

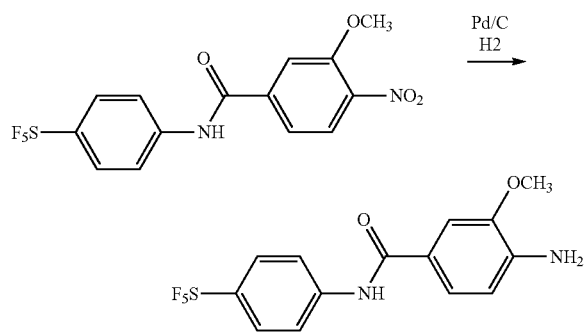

Into a 100 ml flask equipped with a stirrer, a thermometer and a gas inlet, 0.40 g (1.00 mmol) of 4-(4-nitro-3-methoxybenzoylamino)pentafluorosulfanylbenzene, and subsequently 0.2 g of 5% palladium carbon catalyst (50% water-containing product) and 40 ml of ethanol were added. While blowing hydrogen gas into the reaction mixture, the reaction mixture was stirred for 2 hours at room temperature.

After completion of the reaction, the reaction mixture was filtered, and the filtrate was concentrated under reduced pressure. The obtained concentrate was subjected to a reversed-phase type column chromatography (eluent; acetonitrile/0.1%-aqueous formic acid solution=0/100 to 95/5 (solvent ratio)), to obtain 4-(4-amino-3-methoxybenzoylamino)pentafluorosulfanylbenzene 0.19 g (yield 51%) as white powder.

Herein, 4-(4-amino-3-methoxybenzoylamino)pentafluorosulfanylbenzene is a novel compound having the following property values.

$^1$H-NMR (CD$_3$CN, δ (ppm)); 6.90 (2H, s), 7.28 (2H, s), 7.76 (1H, dd, J=2.4, 9.0 Hz), 7.85 (1H, d, J=2.5 Hz), 8.30 (1H, d, J=8.8 Hz), 8.45 (1H, s) MS (ES+); 369 (M+1)

Example 59 Synthesis of Compound 61

(Z=NH, p=0, n=11, m=1; Synthesis of 4-(4-aminobenzoylamino)pentafluorosulfanylbenzene)

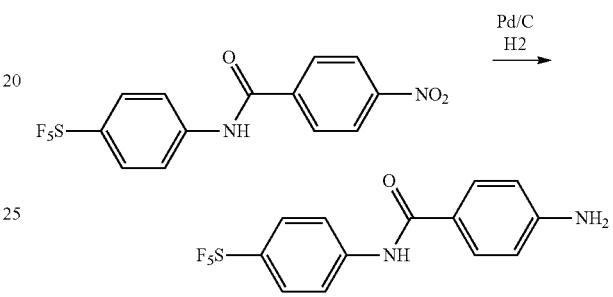

Into a 100 ml flask equipped with a stirrer, a thermometer and a gas inlet, 3.0 g (8.12 mmol) of 4-(4-nitrobenzoylamino)pentafluorosulfanylbenzene, and subsequently 0.2 g of 5% palladium carbon catalyst (50% water-containing product, NX type) and 50 ml of ethanol were added, while blowing hydrogen gas into the reaction mixture, and stirred for 3.5 hours at room temperature.

After completion of the reaction, the reaction mixture was filtered, and the filtrate was concentrated under reduced pressure. The obtained concentrate was subjected to a reversed-phase type column chromatography (eluent; acetonitrile/0.1%-aqueous formic acid solution=0/100 to 95/5 (solvent ratio)), to obtain 4-(4-aminobenzoylamino)pentafluorosulfanylbenzene 1.83 g (yield 67%) as white powder.

Herein, 4-(4-aminobenzoylamino)pentafluorosulfanylbenzene is a novel compound having the following property values.

$^1$H-NMR (DMSO-$d_6$, δ (ppm)); 5.87 (2H, bs), 6.62 (2H, m), 7.76 (2H, m), 7.82-7.88 (2H, m), 7.94-8.02 (2H, m), 10.17 (1H, s)

MS (ES+); 339 (M+1)

Example 61: Synthesis of Compound 63

(Z=NH, p=0, n=1, m=1; Synthesis of 4-(4-aminobenzoylamino)pentafluorosulfanylbenzene hydrochloride salt)

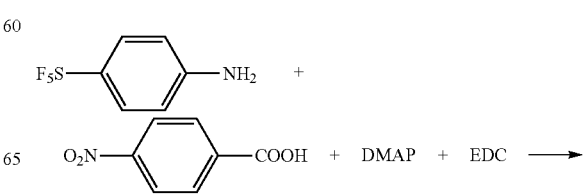

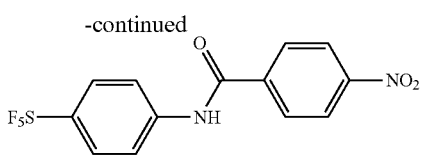
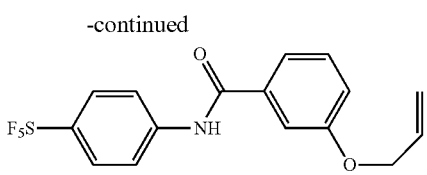

A reaction was carried out as described in Example 2 except that 4-nitrobenzoic acid was used in place of 3,4,5-tribenzyloxybenzoic acid, to obtain 4-(4-nitrobenzoylamino)pentafluorosulfanylbenzene 0.59 g (yield 63%).

Herein, 4-(4-nitrobenzoylamino)pentafluorosulfanylbenzene is a novel compound having the following property values.

$^1$H-NMR (DMSO-d$_6$, δ (ppm)); 7.93 (2H, m), 8.03 (2H, m), 8.22 (2H, m), 8.39 (2H, m), 10.96 (1H, s)

MS (ES−); 367 (M−1)

Example 61 Synthesis of Compound 63

(Z=NH, p=0, n=11, m=0; Synthesis of 4-(4-aminobenzoylamino)pentafluorosulfanylbenzene hydrochloride salt)

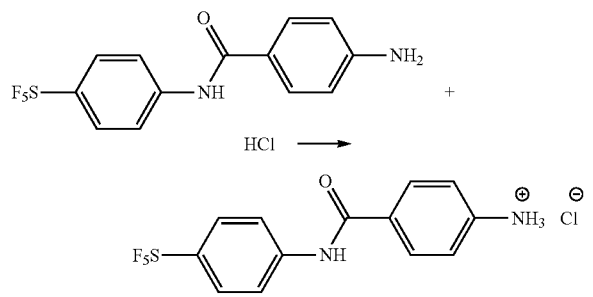

Into a 100 ml flask equipped with a stirrer, 1.0 g (2.95 mmol) of 4-(4-aminobenzoylamino)pentafluorosulfanylbenzene, and subsequently 5.9 ml of 0.5 mol/l hydrochloride methanol solution was added, and stirred for 15 minutes at room temperature.

After completion of the reaction, the reaction mixture was concentrated under reduced pressure. The obtained residue was washed with 10 ml of tert-butyl methyl ether, filtered, and dried to obtain 4-(4-aminobenzoylamino)pentafluorosulfanylbenzene hydrochloride salt 1.05 g (yield 95%).

Herein, 4-(4-aminobenzoylamino)pentafluorosulfanylbenzene hydrochloride salt is a novel compound having the following property values.

$^1$H-NMR (DMSO-d$_6$, δ (ppm)); 6.85 (3H, m), 7.12 (2H, d, J=8.4 Hz), 7.88 (2H, d, J=9.3 Hz), 7.95 (2H, d, J=8.7 Hz), 8.03 (2H, d, J=9.2 Hz), 10.56 (1H, s)

Example 62 Synthesis of Compound 64

(Z=NH, p=0, n=11, m=1; Synthesis of 4-(3-allyloxybenzoylamino)pentafluorosulfanylbenzene)

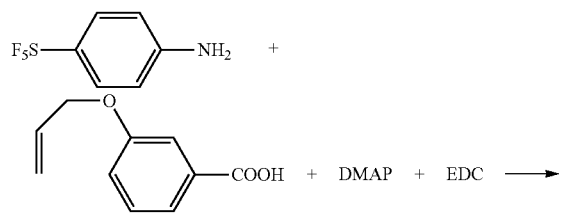

A reaction was carried out as described in Example 2 except that 3-allyloxybenzoic acid was used in place of 3,4,5-tribenzyloxybenzoic acid, to obtain 4-(3-allyloxybenzoylamino)pentafluorosulfanylbenzene 3.39 g (yield 39%).

Herein, 4-(3-allyloxybenzoylamino)pentafluorosulfanylbenzene is a novel compound having the following property values.

$^1$H-NMR (DMSO-d$_6$, δ (ppm)); 4.66-4.69 (2H, m), 5.29 (1H, m), 5.43 (1H, m), 6.02-6.14 (1H, m), 7.19-7.24 (1H, m), 7.47 (1H, t, J=8.0 Hz), 7.50-7.58 (2H, m), 7.87-7.93 (2H, m), 7.97-8.04 (2H, m), 10.60 (1H, s)

Example 63 Synthesis of Compound 65

(Z=NH, p=0, n=11, m=1; Synthesis of 4-(3-hydroxybenzoylamino)pentafluorosulfanylbenzene)

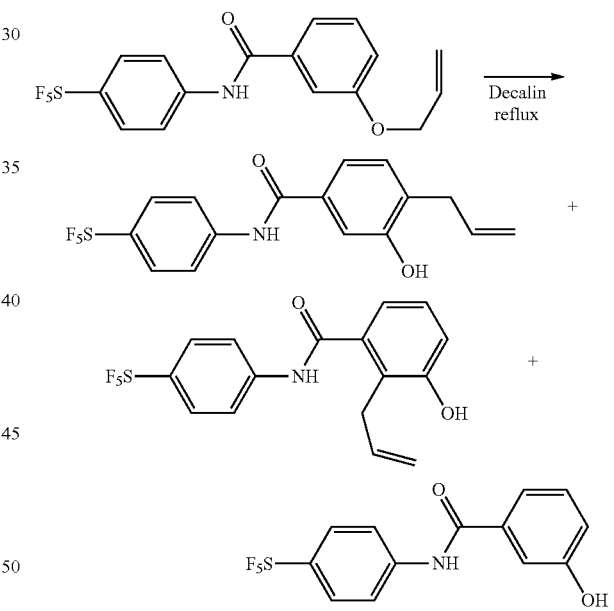

A reaction was carried out as described in Example 30 except that 4-(3-allyloxybenzoylamino)pentafluorosulfanylbenzene was used in place 4-(4-(2-propenyloxy)-3-methoxybenzoylamino)pentafluorosulfanylbenzene, to obtain 4-(3-hydroxybenzoylamino)pentafluorosulfanylbenzene 0.21 g (yield 20%), 4-(2-allyl-3-hydroxybenzoylamino)pentafluorosulfanylbenzene 0.05 g and 4-(4-allyl-3-hydroxybenzoylamino)pentafluorosulfanylbenzene 0.01 g.

Herein, 4-(3-hydroxybenzoylamino)pentafluorosulfanylbenzene, 4-(2-allyl-3-hydroxybenzoylamino)pentafluorosulfanylbenzene and 4-(4-allyl-3-hydroxybenzoylamino)pentafluorosulfanylbenzene are novel compounds having the following property values.

4-(3-hydroxybenzoylamino)pentafluorosulfanylbenzene $^1$H-NMR (DMSO-$d_6$, δ (ppm)); 6.98-7.04 (1H, m), 7.31-7.43 (3H, m), 7.86-7.93 (2H, m), 7.98-8.04 (2H, m), 9.82 (1H, s), 10.58 (1H, s)
MS (ES+); 340 (M+1)

4-(2-allyl-3-hydroxybenzoylamino)pentafluorosulfanylbenzene $^1$H-NMR (CDCl$_3$, δ (ppm)); 3.56-3.61 (2H, m), 5.03-5.12 (1H, m), 5.17-5.24 (1H, m), 5.53 (1H, bs), 6.06-6.20 (1H, m), 6.92-6.99 (1H, m), 7.10-7.16 (1H, m), 7.17-7.25 (1H, t, J=7.8 Hz), 7.65-7.77 (4H, m), 7.85 (1H, bs)
MS (ES+); 380 (M+1)

4-(4-allyl-3-hydroxybenzoylamino)pentafluorosulfanylbenzene $^1$H-NMR (DMSO-$d_6$-H$_2$O, δ (ppm)); 3.33-3.38 (2H, d, J=6.5 Hz), 5.01-5.10 (2H, m), 5.92-6.25 (1H, m), 7.21 (1H, d, J=7.8 Hz), 7.36-7.42 (2H, m), 7.85-7.92 (2H, m), 7.95-8.01 (2H, m)
MS (ES+); 380 (M+1)

Example 64 Synthesis of Compound 66

(Z=NH, p=0, n=11, q=1, m=1; Synthesis of 4-(2-hydroxypyridin-6-yl)carbonylaminopentafluorosulfanylbenzene)

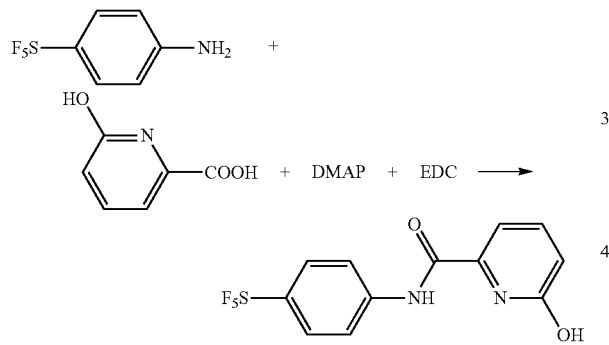

A reaction was carried out as described in Example 2 except that 2-hydroxypyridine-6-carboxylic acid was used in place of 3,4,5-tribenzyloxybenzoic acid, to obtain 4-(2-hydroxypyridin-6-yl)carbonylaminopentafluorosulfanylbenzene 0.97 g (yield 12%).

Herein, 4-(2-hydroxypyridin-6-yl)carbonylaminopentafluorosulfanylbenzene is a novel compound having the following property values.

$^1$H-NMR (DMSO-$d_6$, δ (ppm)); 6.88 (1H, d, J=8.4 Hz), 7.48 (1H, d, J=7.2 Hz), 7.83 (1H, t, J=7.5 Hz), 7.92 (2H, d, J=9.2 Hz), 8.03 (2H, d, J=8.9 Hz), 10.64 (1H, s), 11.52 (1H, bs) MS (ES+); 341 (M+1)

Example 65 Synthesis of Compound 67

(Z=NH, p=0, n=1, q=1, m=1; Synthesis of 4-(2-hydroxypyridin-3-yl)carbonylaminopentafluorosulfanylbenzene)

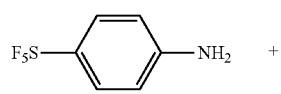

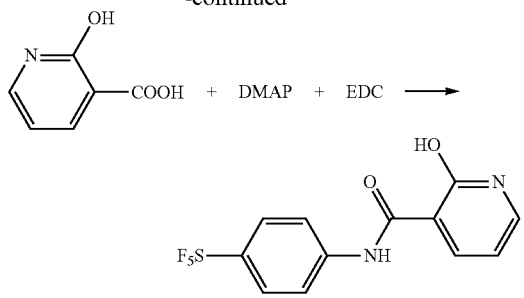

A reaction was carried out as described in Example 2 except that 2-hydroxypyridine-3-carboxylic acid was used in place of 3,4,5-tribenzyloxybenzoic acid, to obtain 4-(2-hydroxypyridin-3-yl)carbonylaminopentafluorosulfanylbenzene 1.03 g (yield 14%).

Herein, 4-(2-hydroxypyridin-3-yl)carbonylaminopentafluorosulfanylbenzene is a novel compound having the following property values.

$^1$H-NMR (DMSO-$d_6$, δ (ppm)); 6.57 (1H, m), 7.83-7.92 (5H, m), 8.49 (1H, dd, J=2.1, 7.2 Hz), 12.55 (1H, s), 12.85 (1H, bs) MS (ES+); 341 (M+1)

Example 66 Synthesis of Compound 68

(Z=NH, p=0, n=11, q=1, m=1; Synthesis of 4-(3-hydroxypyridin-2-yl)carbonylaminopentafluorosulfanylbenzene)

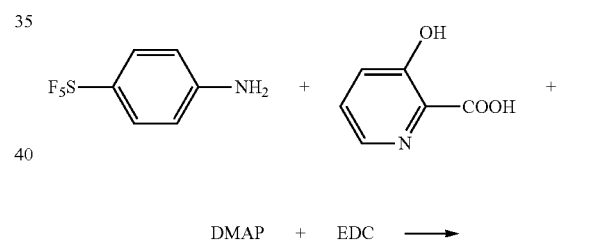

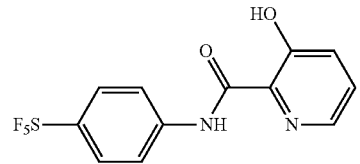

A reaction was carried out as described in Example 2 except that 3-hydroxypyridine-2-carboxylic acid was used in place of 3,4,5-tribenzyloxybenzoic acid, to obtain 4-(3-hydroxypyridin-2-yl)carbonylaminopentafluorosulfanylbenzene 0.45 g (yield 18%).

Herein, 4-(3-hydroxypyridin-2-yl)carbonylaminopentafluorosulfanylbenzene is a novel compound having the following property values.

$^1$H-NMR (DMSO-$d_6$, δ (ppm)); 7.51 (1H, dd, J=1.3, 8.4 Hz), 7.63 (1H, dd, J=4.3, 8.4 Hz), 7.91-7.96 (2H, m), 8.10 (2H, bd), 8.28 (1H, dd, J=1.3, 4.3 Hz), 11.34 (1H, bs), 11.80 (1H, bs)
MS (ES+); 341 (M+1)

Example 67 Synthesis of Compound 69

(Z=NH, p=0, n=11, q=1, m=1; Synthesis of 4-(4-hydroxy-pyrimidin-6-yl)carbonylaminopentafluorosulfanylbenzene)

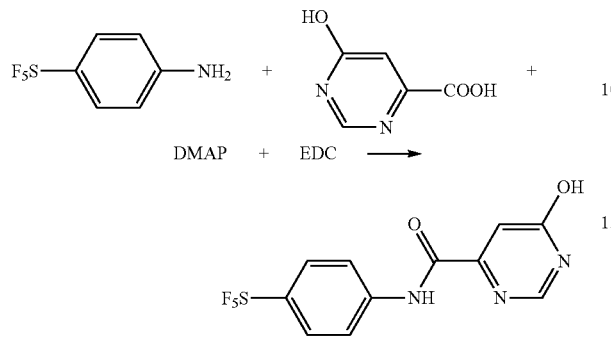

A reaction was carried out as described in Example 2 except that 4-hydroxypyrimidine-6-carboxylic acid was used in place of 3,4,5-tribenzyloxybenzoic acid, to obtain 4-(4-hydroxypyrimidin-6-yl)carbonylaminopentafluorosulfanylbenzene 0.07 g (yield 3%).

Herein, 4-(4-hydroxypyrimidin-6-yl)carbonylaminopentafluorosulfanylbenzene is a novel compound having the following property values.

$^1$H-NMR (DMSO-$d_6$, δ (ppm)); 6.96 (1H, d, J=1.0 Hz), 7.88-7.93 (2H, m), 8.10 (2H, bd, J=9.0 Hz), 8.38 (1H, d, J=1.0 Hz), 10.89 (1H, s), 13.1 (1H, bs)

MS (ES+); 383 (M+1+CH$_3$CN), 341 (M+1)

Example 68 Synthesis of Compound 70

(Z=NH, p=0, n=11, q=1, m=0; Synthesis of 4-(pyrimidin-2-yl)carbonylaminopentafluorosulfanylbenzene)

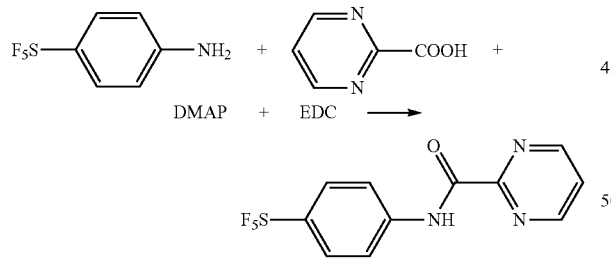

A reaction was carried out as described in Example 2 except that pyrimidine-2-carboxylic acid was used in place of 3,4,5-tribenzyloxybenzoic acid, to obtain 4-(pyrimidin-2-yl)carbonylaminopentafluorosulfanylbenzene 1.65 g (yield 42%).

Herein, 4-(pyrimidin-2-yl)carbonylaminopentafluorosulfanylbenzene is a novel compound having the following property values.

$^1$H-NMR (DMSO-$d_6$, δ (ppm)); 7.79 (1H, t, J=4.9 Hz), 7.89-7.97 (2H, m), 8.13 (2H, bd, J=9.0 Hz), 9.07 (1H, d, J=4.9 Hz), 11.21 (1H, s)

MS (ES+); 326 (M+1)

Example 69 Synthesis of Compound 71

(Z=NH, p=0, n=11, q=1, m=0; Synthesis of 4-(pyridin-2-yl)carbonylaminopentafluorosulfanylbenzene)

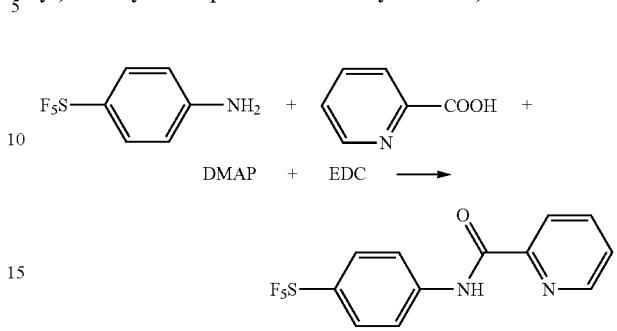

A reaction was carried out as described in Example 2 except that pyridine-2-carboxylic acid was used in place of 3,4,5-tribenzyloxybenzoic acid, to obtain 4-(pyridin-2-yl)carbonylaminopentafluorosulfanylbenzene 1.60 g (yield 30%).

Herein, 4-(pyridin-2-yl)carbonylaminopentafluorosulfanylbenzene is a novel compound having the following property values.

$^1$H-NMR (DMSO-$d_6$, δ (ppm)); 7.68-7.75 (1H, m), 7.87-7.95 (2H, m), 8.06-8.14 (1H, m), 8.14-8.23 (3H, m), 8.75-8.80 (1H, m), 11.10 (1H, s)

MS (ES+); 325 (M+1)

Example 70 Synthesis of Compound 72

(Z=NH, p=0, n=11, q=1, m=0; Synthesis of 4-(pyridin-4-yl)carbonylaminopentafluorosulfanylbenzene)

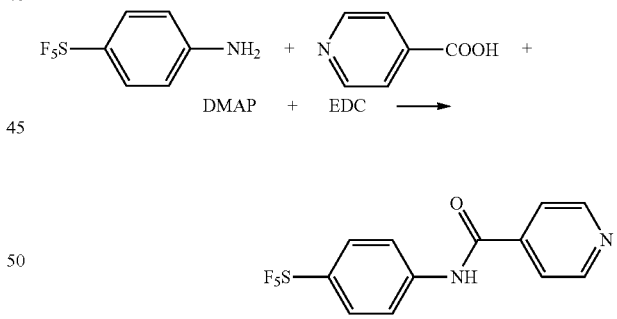

A reaction was carried out as described in Example 2 except that pyridine-4-carboxylic acid was used in place of 3,4,5-tribenzyloxybenzoic acid, to obtain 4-(pyridin-4-yl)carbonylaminopentafluorosulfanylbenzene 2.20 g (yield 42%).

Herein, 4-(pyridin-4-yl)carbonylaminopentafluorosulfanylbenzene is a novel compound having the following property values.

$^1$H-NMR (DMSO-$d_6$, δ (ppm)); 7.86-7.91 (2H, m), 7.91-7.97 (2H, m), 8.03 (2H, bd, J=9.2 Hz), 8.80-8.85 (2H, m), 10.90 (1H, bs)

MS (ES+); 325 (M+1)

Example 71 Synthesis of Compound 73

(Z=NH, p=0, n=11, q=1, m=0; Synthesis of 4-(pyrimidin-4-yl)carbonylaminopentafluorosulfanylbenzene)

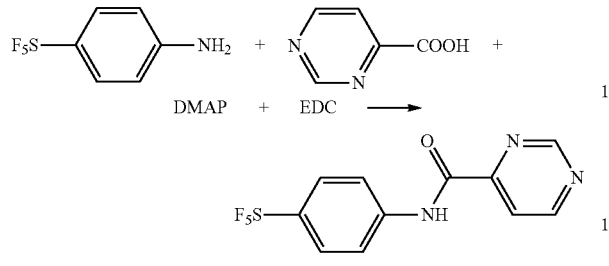

A reaction was carried out as described in Example 2 except that pyrimidine-4-carboxylic acid was used in place of 3,4,5-tribenzyloxybenzoic acid, to obtain 4-(pyrimidin-4-yl)carbonylaminopentafluorosulfanylbenzene 0.37 g (yield 9%).

Herein, 4-(pyrimidin-4-yl)carbonylaminopentafluorosulfanylbenzene is a novel compound having the following property values.

$^1$H-NMR (DMSO-d$_6$, δ (ppm)); 7.90-7.98 (2H, m), 7.92-7.98 (3H, m), 9.17 (1H, d, J=5.0 Hz), 9.46 (1H, d, J=1.3 Hz), 11.29 (1H, s)

MS (ES+); 325 (M+1)

Example 72 Synthesis of Compound 74

(Z=NH, p=0, n=11, q=1, m=2; Synthesis of 4-(6,7-dihydroxycoumarin-3-yl)carbonylaminopentafluorosulfanylbenzene)

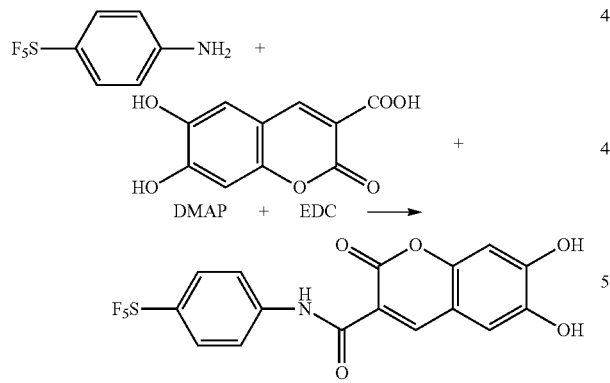

A reaction was carried out as described in Example 2 except that 6,7-dihydroxycoumarin-3-carboxylic acid was used in place of 3,4,5-tribenzyloxybenzoic acid, to obtain 4-(6,7-dihydroxycoumarin-3-yl)carbonylaminopentafluorosulfanylbenzene 0.05 g (yield 3%).

Herein, 4-(6,7-dihydroxycoumarin-3-yl)carbonylaminopentafluorosulfanylbenzene is a novel compound having the following property values.

1H-NMR (DMSO-d$_6$, δ (ppm)); 6.87 (1H, s), 7.27 (1H, s), 7.87-7.97 (4H, m), 8.84 (1H, s), 10.5 (2H, bs), 11.05 (1H, s)

MS (ES+); 424 (M+1)

Example 73 Synthesis of Compound 75

(Z=NH, p=0, n=11, q=1, m=1; Synthesis of 4-(3-fluoropyridin-4-yl)carbonylaminopentafluorosulfanylbenzene)

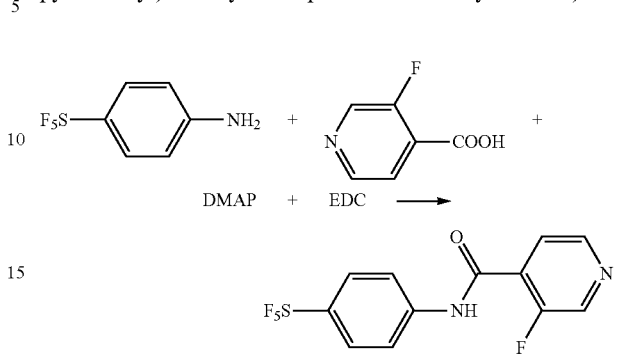

A reaction was carried out as described in Example 2 except that 3-fluoropyridine-4-carboxylic acid was used in place of 3,4,5-tribenzyloxybenzoic acid, to obtain 4-(3-fluoropyridin-4-yl)carbonylaminopentafluorosulfanylbenzene 0.085 g (yield 4%).

Herein, 4-(3-fluoropyridin-4-yl)carbonylaminopentafluorosulfanylbenzene is a novel compound having the following property values.

$^1$H-NMR (CDCl$_3$, δ (ppm)); 7.75-7.83 (4H, m), 8.03 (1H, dd, J=5.0, 6.5 Hz), 8.51 (1H, bs), 8.67 (1H, dd, J=1.5, 5.0 Hz), 8.70 (1H, d, J=2.8 Hz) MS (ES+); 384 (M+1+CH$_3$CN), 343 (M+1)

Example 74 Synthesis of Compound 76

(Z=NH, p=0, n=11, q=1, m=1; Synthesis of 4-(2-fluoropyridin-4-yl)carbonylaminopentafluorosulfanylbenzene)

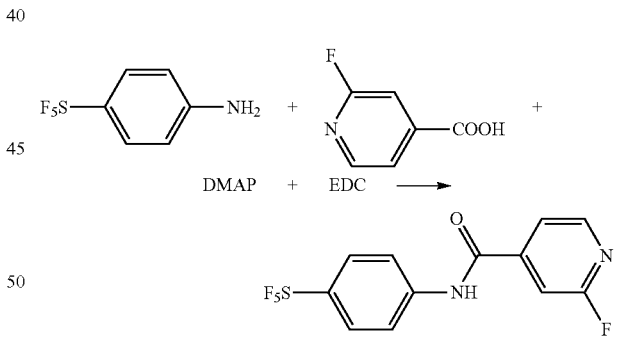

A reaction was carried out as described in Example 2 except that 2-fluoropyridine-4-carboxylic acid was used in place of 3,4,5-tribenzyloxybenzoic acid, to obtain 4-(2-fluoropyridin-4-yl)carbonylaminopentafluorosulfanylbenzene 0.55 g (yield 21%).

Herein, 4-(2-fluoropyridin-4-yl)carbonylaminopentafluorosulfanylbenzene is a novel compound having the following property values.

$^1$H-NMR (CDCl$_3$, δ (ppm)); 7.35-7.40 (1H, m), 7.57-7.63 (1H, m), 7.72-7.82 (4H, m), 8.08 (1H, bs), 8.42 (1H, d, J=5.2 Hz)

MS (ES+); 384 (M+1+CH$_3$CN), 343 (M+1)

Example 75 Synthesis of Compound 78

(Z=NH, p=0, n=11, q=1, m=0; Synthesis of 4-(imidazol-2-yl)carbonylaminopentafluorosulfanylbenzene)

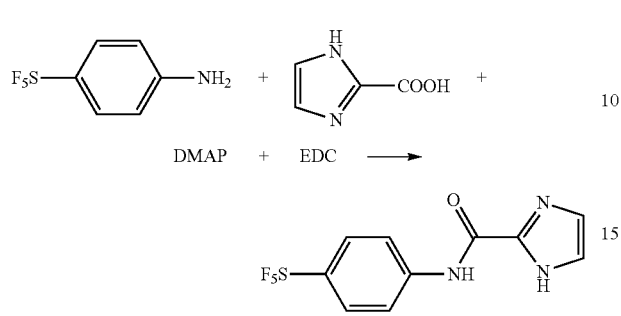

A reaction was carried out as described in Example 2 except that imidazole-2-carboxylic acid was used in place of 3,4,5-tribenzyloxybenzoic acid, to obtain 4-(imidazol-2-yl)carbonylaminopentafluorosulfanylbenzene 0.07 g (yield 3%).

Herein, 4-(imidazol-2-yl)carbonylaminopentafluorosulfanylbenzene is a novel compound having the following property values.

$^1$H-NMR (DMSO-$d_6$, δ (ppm)); 7.30 (2H, s), 7.88 (2H, d, J=9.3 Hz), 8.08 (2H, d, J=8.9 Hz), 10.86 (1H, bs), 13.35 (1H, bs)

MS (ES+); 314 (M+1)

Example 76 Synthesis of Compound 79

(Z=NH, p=0, n=1, q=1, m=0; Synthesis of 4-(pyrazin-2-yl)carbonylaminopentafluorosulfanylbenzene)

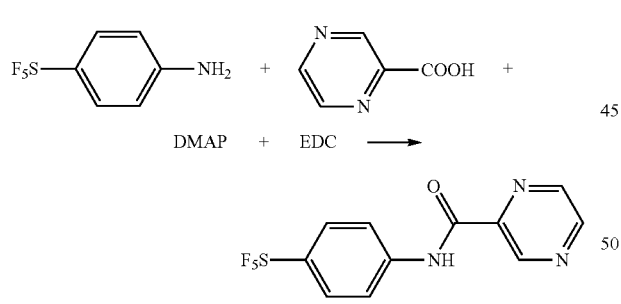

A reaction was carried out as described in Example 2 except that pyrazine-2-carboxylic acid was used in place of 3,4,5-tribenzyloxybenzoic acid, to obtain 4-(pyrazin-2-yl)carbonylaminopentafluorosulfanylbenzene 1.02 g (yield 41%).

Herein, 4-(pyrazin-2-yl)carbonylaminopentafluorosulfanylbenzene is a novel compound having the following property values.

$^1$H-NMR (DMSO-$d_6$, δ (ppm)); 7.90-7.97 (2H, m), 7.13-7.18 (2H, m), 8.85 (1H, m), 8.97 (1H, d, J=2.4 Hz), 9.33 (1H, d, J=1.5 Hz), 11.20 (1H, s)

MS (ES+); 367 (M+1+CH$_3$CN), 326 (M+1)

Example 77 Synthesis of Compound 80

(Z=NH, p=0, n=11, q=1, m=0; Synthesis of 4-(pyrrol-1-yl)carbonylaminopentafluorosulfanylbenzene)

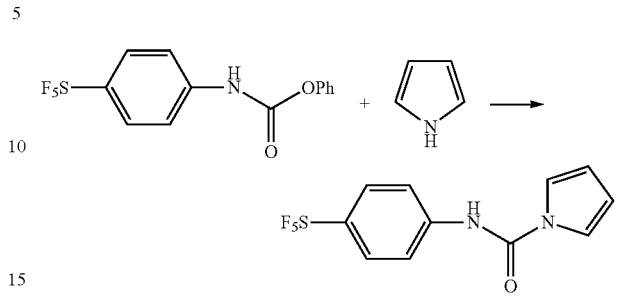

Into a 100 ml flask equipped with a stirrer, 0.50 g (1.47 mmol) of 4-(phenoxycarbonylamino)pentafluorosulfanylbenzene, 10 ml of acetonitrile, and subsequently 0.30 g (4.42 mmol) of pyrrole were added, and refluxed for 7 hours.

After completion of the reaction, 1 g of diatomaceous earth was added, and the reaction mixture was concentrated under reduced pressure. The obtained residue was subjected to a reversed-phase type column chromatography, to obtain 4-(pyrrol-1-yl)carbonylaminopentafluorosulfanylbenzene 0.32 g (yield 70%) as white powder.

Herein, 4-(pyrrol-1-yl)carbonylaminopentafluorosulfanylbenzene is a novel compound having the following property values.

$^1$H-NMR (DMSO-$d_6$, δ (ppm)); 6.33 (2H, m), 7.57 (2H, m), 7.85-7.94 (4H, m), 10.37 (1H, bs)

MS (ES+); 313 (M+1)

Example 78 Synthesis of Compound 81

(Z=NH, p=0, n=11, q=1, m=0; Synthesis of 4-(oxazol-4-yl)carbonylaminopentafluorosulfanylbenzene)

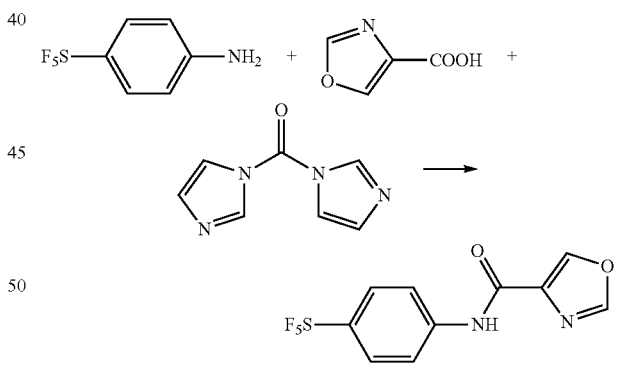

Into a 100 ml flask equipped with a stirrer, 1.0 g (8.84 mmol) of oxazole-4-carboxylic acid, 10 ml of ethyl acetate, and subsequently 1.58 g (9.72 mmol) of carbonyl diimidazole (CDI) were added, and refluxed for 2.5 hours. Subsequently, 1.84 g (8.40 mmol) of 4-aminopentafluorosulfanylbenzene was added and refluxed again for 3 hours.

After completion of the reaction, the reaction mixture was cooled to room temperature, and the precipitated crystals were filtered off. After the filtrate was concentrated, 5 ml of acetonitrile was added to precipitate crystals, which were collected by filtration to obtain 4-(oxazol-4-yl)carbonylaminopentafluorosulfanylbenzene 0.21 g (yield 8%) as white powder.

Herein, 4-(oxazol-4-yl)carbonylaminopentafluorosulfanylbenzene is a novel compound having the following property values.

$^1$H-NMR (DMSO-d$_6$, δ (ppm)); 7.86-7.93 (2H, m), 8.02-8.08 (2H, m), 8.67 (1H, d, J=0.9 Hz), 8.89 (1H, d, J=1.0 Hz), 10.66 (1H, s)

Example 79 Synthesis of Compound 82

(Z=NH, p=0, n=1, q=1, m=0; Synthesis of 4-(oxazol-5-yl)carbonylaminopentafluorosulfanylbenzene)

Into a 100 ml flask equipped with a stirrer, 1.0 g (8.84 mmol) of oxazole-5-carboxylic acid, 10 ml of ethyl acetate, and subsequently 1.58 g (9.72 mmol) of carbonyl diimidazole (CDI) were added, and refluxed for 2.5 hours. Subsequently, 1.84 g (8.40 mmol) of 4-aminopentafluorosulfanylbenzene was added and refluxed again for 9 hours.

After completion of the reaction, 2 g of diatomaceous earth was added, and the reaction mixture was concentrated under reduced pressure. The obtained residue was subjected to a reversed-phase type column chromatography (eluent; acetonitrile/0.1% aqueous formic acid solution=0/100 to 95/5 (solvent ratio)), to obtain 4-(oxazol-5-yl)carbonylaminopentafluorosulfanylbenzene 1.37 g (yield 52%) as white powder.

Herein, 4-(oxazol-5-yl)carbonylaminopentafluorosulfanylbenzene is a novel compound having the following property values.

$^1$H-NMR (DMSO-d$_6$, δ (ppm)); 7.89-8.00 (4H, m), 8.06 (1H, s), 8.71 (1H, s), 10.84 (1H, bs)

MS (ES+); 356 (M+1+CH$_3$CN), 315 (M+1)

Example 80 Synthesis of Compound 83

(Z=NH, p=0, n=11, q=1, m=0; Synthesis of 4-(pyrrol-2-yl)carbonylaminopentafluorosulfanylbenzene)

A reaction was carried out as described in Example 79 except that pyrrole-2-carboxylic acid was used in place of oxazole-5-carboxylic acid, to obtain 4-(pyrrol-2-yl)carbonylaminopentafluorosulfanylbenzene 0.12 g (yield 4%).

Herein, 4-(pyrrol-2-yl)carbonylaminopentafluorosulfanylbenzene is a novel compound having the following property values.

$^1$H-NMR (DMSO-d$_6$, δ (ppm)); 6.20 (1H, dd, J=2.4, 3.6 Hz), 7.02 (1H, dd, J=1.5, 2.4 Hz), 7.13 (1H, dd, J=1.4, 3.6 Hz), 7.83-7.90 (2H, m), 7.97 (2H, bd, J=9.2 Hz), 10.14 (1H, bs), 11.78 (1H, bs)

MS (ES+); 313 (M+1)

Example 81 Synthesis of Compound 84

(Z=NH, p=0, n=11, q=1, m=0; Synthesis of 4-(pyrazol-1-yl)carbonylaminopentafluorosulfanylbenzene)

A reaction was carried out as described in Example 77 except that pyrazole was used in place of pyrrole, to obtain 4-(pyrazol-1-yl)carbonylaminopentafluorosulfanylbenzene 0.24 g (yield 60%).

Herein, 4-(pyrazol-1-yl)carbonylaminopentafluorosulfanylbenzene is a novel compound having the following property values.

$^1$H-NMR (DMSO-d$_6$, δ (ppm)); 6.65 (1H, dd, J=1.6, 2.8 Hz), 7.89-7.96 (3H, m), 8.01 (2H, bd, J=9.2 Hz), 8.47 (1H, d, J=2.8 Hz), 10.94 (1H, bs)

Example 82 Synthesis of Compound 85

(Z=NH, p=0, n=11, q=1, m=0; Synthesis 4-(pyrrol-3-yl)carbonylaminopentafluorosulfanylbenzene)

Into a 100 ml flask equipped with a stirrer, 1.0 g (9.00 mmol) of pyrrole-3-carboxylic acid, methylene chloride 20 ml, and subsequently 6.85 g (54.0 mmol) of oxalyl chloride and 5 drops of DMF were added, and stirred for 2 hours at room temperature. The reaction mixture was concentrated under reduced pressure, and 20 ml of methylene chloride was added to the obtained residue. Subsequently, 1.87 g (8.55 mmol) of 4-aminopentafluorosulfanylbenzene and 0.95 g (9.41 mmol) of triethylamine were added, and stirred for 1 hour at room temperature.

After completion of the reaction, 2 g of diatomaceous earth was added, and the reaction mixture was concentrated under reduced pressure. The obtained residue was subjected to a reversed-phase type column chromatography (eluent; acetonitrile/0.1%-aqueous formic acid solution=0/100 to 95/5 (solvent ratio)), and, for the additional purification, subjected to a normal-phase type column chromatography (eluent; n-hexane/ethyl acetate=100/0 to 70/30 (solvent ratio)), to obtain 4-(pyrrol-3-yl)carbonylaminopentafluorosulfanylbenzene 0.14 g (yield 5%) as white powder.

Herein, 4-(pyrrol-3-yl)carbonylaminopentafluorosulfanylbenzene is a novel compound having the following property values.

$^1$H-NMR (DMSO-$d_6$, δ (ppm)); 6.67 (1H, m), 6.84 (1H, m), 7.59 (1H, m), 7.81-7.87 (2H, m), 7.93-7.99 (2H, bd, J=9.2 Hz), 9.90 (1H, s), 11.39 (1H, bs)

Example 83 Synthesis of Compound 86

(Z=NH, p=0, n=11, q=1, m=0; Synthesis of 4-(pyrazol-3-yl)carbonylaminopentafluorosulfanylbenzene)

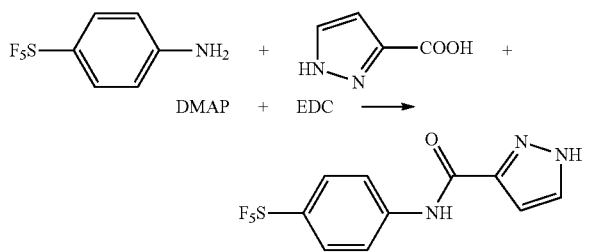

A reaction was carried out as described in Example 2 except that pyrazole-3-carboxylic acid was used in place of 3,4,5-tribenzyloxybenzoic acid, to obtain 4-(pyrazol-3-yl)carbonylaminopentafluorosulfanylbenzene 0.26 g (yield 18%).

Herein, 4-(pyrazol-3-yl)carbonylaminopentafluorosulfanylbenzene is a novel compound having the following property values.

$^1$H-NMR (DMSO-$d_6$, δ (ppm)); 6.85 (1H, s), 7.83-7.92 (3H, m), 8.03-8.09 (2H, m), 10.55 (1H, bs), 13.55 (1H, bs)
MS (ES+); 314 (M+1)

Example 84 Synthesis of Compound 87

(Z=NH, p=0, n=11, q=1, m=0; Synthesis of 4-(furan-2-yl)carbonylaminopentafluorosulfanylbenzene)

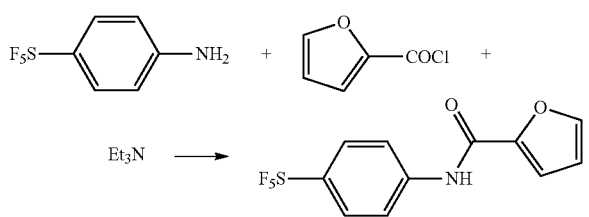

A reaction was carried out as described in Example 35 except that furan-2-carbonyl chloride was used in place of 3,4,5-tribenzyloxybenzoic acid, to obtain 4-(furan-2-yl)carbonylaminopentafluorosulfanylbenzene 0.42 g (yield 29%).

Herein, 4-(furan-2-yl)carbonylaminopentafluorosulfanylbenzene is a novel compound having the following property values.

$^1$H-NMR (DMSO-$d_6$, δ (ppm)); 6.72-6.77 (1H, m), 7.40-7.44 (1H, m), 7.86-7.93 (2H, m), 7.97-8.03 (3H, m), 10.61 (1H, s)
MS (ES+); 314 (M+1)

Example 85 Synthesis of Compound 88

(Z=NH, p=0, n=11, q=1, m=0; Synthesis of 4-(thiophen-2-yl)carbonylaminopentafluorosulfanylbenzene)

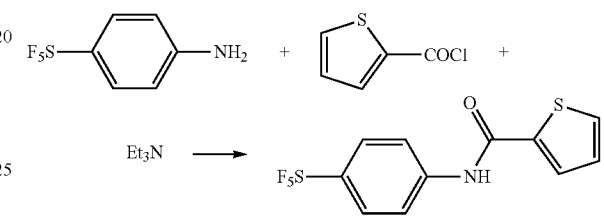

A reaction was carried out as described in Example 84 except that thiophene-2-carbonyl chloride was used in place of furan-2-carbonyl chloride, to obtain 4-(thiophen-2-yl)carbonylaminopentafluorosulfanylbenzene 0.68 g (yield 48%).

Herein, 4-(thiophen-2-yl)carbonylaminopentafluorosulfanylbenzene is a novel compound having the following property values.

$^1$H-NMR (DMSO-$d_6$, δ (ppm)); 7.23-7.29 (1H, m), 7.86-7.95 (3H, m), 7.98 (2H, bd, J=9.3 Hz), 8.06-8.09 (1H, dd, J=1.1, 3.8 Hz), 10.62 (1H, bs)
MS (ES+); 330 (M+1)

Example 86 Synthesis of Compound 89

(Z=NH, p=0, n=11, q=1, m=0; Synthesis of 4-(furan-3-yl)carbonylaminopentafluorosulfanylbenzene)

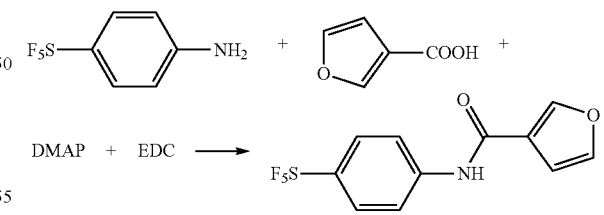

A reaction was carried out as described in Example 2 except that furan-3-carboxylic acid was used in place of 3,4,5-tribenzyloxybenzoic acid, to obtain 4-(furan-3-yl)carbonylaminopentafluorosulfanylbenzene 0.47 g (yield 17%).

Herein, 4-(furan-3-yl)carbonylaminopentafluorosulfanylbenzene is a novel compound having the following property values.

1H-NMR (DMSO-$d_6$, δ (ppm)); 7.02 (1H, m), 7.83 (1H, m), 7.87-7.98 (4H, m), 8.45 (1H, m), 10.32 (1H, bs) MS (ES+); 314 (M+1)

Example 87 Synthesis of Compound 90

(Z=NH, p=0, n=11, q=1, m=0; Synthesis of 4-(thiophen-3-yl)carbonylaminopentafluorosulfanylbenzene)

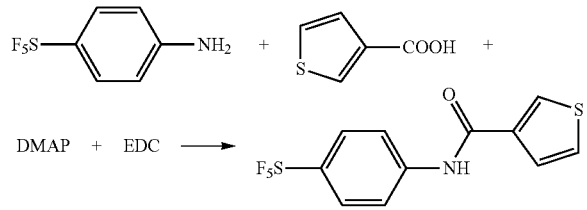

A reaction was carried out as described in Example 2 except that thiophene-3-carboxylic acid was used in place of 3,4,5-tribenzyloxybenzoic acid, to obtain 4-(thiophen-3-yl)carbonylaminopentafluorosulfanylbenzene 0.39 g (yield 15%).

Herein, 4-(thiophen-3-yl)carbonylaminopentafluorosulfanylbenzene is a novel compound having the following property values.

$^1$H-NMR (DMSO-$d_6$, δ (ppm)); 7.62-7.68 (1H, m), 7.66-7.72 (1H, m), 7.86-7.94 (2H, m), 7.99 (2H, bd, J=9.0 Hz), 8.40-8.45 (1H, m), 10.46 (1H, bs)

MS (ES+); 330 (M+1)

Example 88 Synthesis of Compound 91

(Z=NH, p=0, n=11, q=1, m=1; Synthesis of 4-(3-hydroxypyridazin-6-yl)carbonylaminopentafluorosulfanylbenzene)

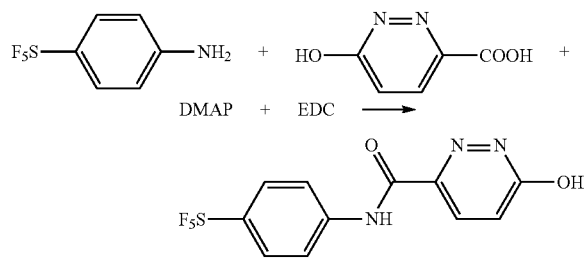

A reaction was carried out as described in Example 2 except that 3-hydroxypyridazine-6-carboxylic acid was used in place of 3,4,5-tribenzyloxybenzoic acid, to obtain 4-(3-hydroxypyridazin-6-yl)carbonylaminopentafluorosulfanylbenzene 0.47 g (yield 17%).

Herein, 4-(3-hydroxypyridazin-6-yl)carbonylaminopentafluorosulfanylbenzene is a novel compound having the following property values.

$^1$H-NMR (DMSO-$d_6$, δ (ppm)); 7.04 (1H, d, J=9.9 Hz), 7.86-7.96 (3H, m), 8.04 (2H, bd, J=9.2 Hz), 13.62 (1H, bs)

MS (ES+); 383 (M+1+CH$_3$CN), 342 (M+1)

Example 89 Synthesis of Compound 92

(Z=NH, p=0, n=11, q=1, m=1; Synthesis of 4-(2-bromothiazol-5-yl)carbonylaminopentafluorosulfanylbenzene)

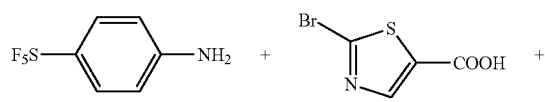

DMAP + EDC ⟶

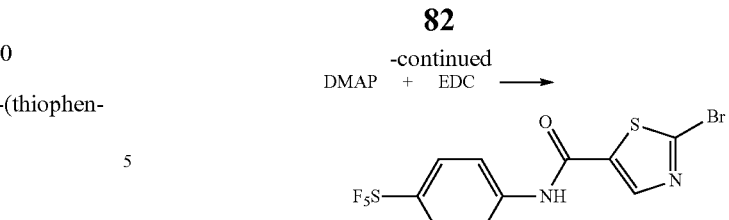

A reaction was carried out as described in Example 2 except that 2-bromothiazole-5-carboxylic acid was used in place of 3,4,5-tribenzyloxybenzoic acid, to obtain 4-(2-bromothiazol-5-yl)carbonylaminopentafluorosulfanylbenzene 0.44 g (yield 31%).

Herein, 4-(2-bromothiazol-5-yl)carbonylaminopentafluorosulfanylbenzene is a novel compound having the following property values.

$^1$H-NMR (DMSO-$d_6$, δ (ppm)); 7.90-7.96 (4H, m), 8.50 (1H, s), 10.87 (1H, bs)

MS (ES+); 411 (M+2), 409 (M)

<Part B>

Properties of the compounds prepared in the above Examples were tested. "Compound 1" synthesized in Example 1 may be sometimes referred to as "Example Compound 1". This also applies to the compounds synthesized in other Examples.

Example B1

Growth inhibitory action and bactericidal action on *salmonella*

1) Preparation of Test-Substance Solution

Test substances (compounds listed in Table 1) each were prepared by dissolving it in DMSO when used. Preparation was made in such a manner that the highest dose became 5000 μg/plate and the dose lower than this was prepared by a dilution method. In the table, reference numerals of individual compounds correspond to the numbers of the individual compounds synthesized in the above Examples (the same applies to the following Tables).

2) Strains in Use

*Salmonella typhimurium* TA98 strain and TA100 strain were used.

These were supplied by Japan Bioassay Research Center, proliferated and examined for genetic properties and other properties in accordance with customary methods, in advance. After these strains were confirmed to have these properties, they are cryopreserved (−80° C.) with a DMSO-added medium; and thawed for use in each test.

3) A cryopreserved strain was thawed and inoculated in a 2.5% aqueous nutrient broth (OXOID No. 2) solution and cultured while shaking at 37° C. for 7 hours to obtain a cell suspension, which was subjected to tests.

4) Medium

A minimum glucose agar plate medium (Vital Media AMT-S, manufactured by Kyokuto Pharmaceutical Industrial Co., Ltd.) was used.

The top agar was prepared when used by blending an aqueous solution of 0.5 mM L-histidine and 0.5 mM D-(+)-biotin with an aqueous solution prepared by adding Bacto Agar (Difco) (0.6%) and sodium chloride (0.5%).

5) S9 Mix

S9 was purchased from Kikkoman; whereas a cofactor was previously prepared in accordance with a method known in the art. They were mixed in a customary method to prepare S9 mix.

6) Test Method

Using a test system containing S9 mix and a test system containing no S9 mix, a test was carried out in accordance with a preincubation method. As the dose selection, the highest dose was specified as 5000 g/plate, which was then serially diluted in a common ratio of 2 to prepare a total of 15 doses to be used in the test.

To a sterile test tube, a test solution (0.1 mL) and 0.1 M Na-phosphate buffer or S9 mix (0.5 mL) and a cell suspension (0.1 mL) were sequentially dispensed. Pre-incubation was carried out at 37° C. for 20 minutes while shaking. After completion of the pre-incubation, top agar (2 mL) kept warm at 45° C. was added, mixed and placed on a minimum glucose agar plate medium. After solidification, the plate was turned upside down and cultured at 37° C. for 48 hours.

After completion of the culture, the state of microbial growth was observed by a stereomicroscope. After a precipitate on the plate was observed, revertant colonies were counted by the naked eye or a colony counter.

7) Criteria for Determination

Table 1 collectively shows the structures of test compounds, growth inhibitory concentrations and bactericidal concentrations thereof. Growth of both TA98 and TA100 strains was examined in the presence or absence of S9 mix. Among the resultant concentrations at which growth was inhibited, the lowest concentration was specified as the growth inhibitory concentration. Similarly, the bactericidal concentration was specified as the lowest concentration at which all bacterial cells were killed.

TABLE 1

Growth inhibitory action and bactericidal action on *salmonella*

| Compound of Example | Growth inhibition (µg/plate) | Bactericidal action (µg/plate) |
|---|---|---|
| 3 | 19.5 | 625 |
| 4 | <39.1*[1] | 156 |
| 5 | 19.5 | 78.1 |
| 7 | 19.5 | 156 |
| 9 | 156 | 625 |
| 11 | 78.1 | 625 |
| 12 | 313 | 1250 |
| 14 | 625 | 1250 |
| 20 | 156 | >625*[2] |
| 22 | 156 | 156 |
| 35 | 39.1 | >2500 |

*[1]When Compound 4 was used, growth inhibition was confirmed at a concentration of 39.1 µg/plate or more.
*[2]When Compound 20 was used, a test substance was precipitated at a concentration of 625 µg/plate or more and detection could not made.

Example B2

K562 Human Leukemia Cell-Proliferation Inhibition Test

A cell proliferation inhibition test using K562 cells was performed. The activity in the presence of a test substance was compared to the activity in the presence of green tea polyphenol (GTP). The materials used in the test are as follows.

Cells: K562 human leukemia-derived cell lines (DS Pharma Biomedical Co., Ltd.)

Control Substance: Green Tea Polyphenols, abbreviation: GTP (LKT Laboratories, Inc.)

Culture solution: 10% equine serum-supplemented RPMI1640 medium

1) Test Method

A test substance and a control substance were used by dissolving each of them in DMSO. To a solution (0.99 mL) containing K562 cells in a cell concentration of 20,000 cells/mL, a test substance solution or a control substance solution (0.01 mL) was added and the cells were cultured. Seventy two hours later, a part of the cells was stained with trypan blue and viable cells were counted by a counting chamber.

2) Test Results

The results of the K562 human leukemia cell proliferation inhibition test are shown in Table 2. In Table 2, "$IC_{50}$" denotes the sample concentration inhibiting 50% of cell proliferation

TABLE 2

K562 human leukemia cell-proliferation inhibition action

| Compound of Example | $IC_{50}$ (µg/mL) |
|---|---|
| GTP | 51 |
| 1 | 1.5 |
| 3 | 0.81 |
| 4 | 2.2 |
| 5 | 0.36 |
| 7 | 1.9 |
| 8 | 8.5 |
| 9 | 1.2 |
| 11 | 1.5 |
| 19 | 0.66 |
| 20 | 1.7 |
| 21 | 0.93 |
| 23 | 4.1 |
| 24 | 14 |
| 25 | 6.3 |
| 28 | 0.8 |
| 30 | 0.9 |
| 31 | 0.88 |
| 32 | 4.6 |
| 33 | 2.7 |
| 35 | 0.2 |
| 37 | 4.8 |
| 38 | 0.6 |
| 41 | 0.81 |
| 42 | 1.7 |
| 43 | 2.8 |
| 44 | 1.0 |
| 45 | 0.51 |
| 46 | 2.5 |
| 47 | 3.5 |
| 48 | 1.9 |
| 50 | 3.5 |
| 51 | 1.2 |
| 52 | 0.28 |
| 53 | 0.9 |
| 56 | 0.83 |
| 57 | 3.3 |
| 58 | 5.3 |
| 59 | 1.1 |
| 60 | 0.10 |
| 61 | 0.086 |
| 62 | 0.78 |
| 63 | 0.85 |
| 64 | 1.1 |
| 65 | 0.92 |
| 66 | 2.3 |
| 68 | 4.2 |
| 69 | 2 |
| 70 | 1.5 |
| 71 | 4.4 |
| 72 | 0.10 |
| 73 | 2.3 |
| 74 | 5.0 |
| 75 | 2.0 |
| 76 | 2.0 |
| 78 | 3.4 |

TABLE 2-continued

K562 human leukemia cell-proliferation inhibition action

| Compound of Example | IC$_{50}$ (µg/mL) |
|---|---|
| 79 | 4.2 |
| 80 | 4.9 |
| 81 | 2.0 |
| 82 | 3.6 |

Example B3

(Test of Inducing Apoptosis of A549 Cells (Human Lung Cancer, Adenocarcinoma))

To evaluate apoptosis induction of a sample (Compound 3), the activity of caspase 3/7 was measured.

1. Measurement Reagents, Equipment and Instruments

APO-ONE Homogeneous Caspase-3/7 Assay (G7790, Lot No. 314408; Promega)

Fluorescence plate reader (SpectraMax GEMINI EM; Molecular Devices)

96-well black plate (353945; BD FALCON)

2. Cells and Medium

Cells: A549 cells (obtained from the Research Resource Bank of the Human Sciences Foundation)

Medium: 10% FBS and 0.1 mmol/L Non-Essential Amino Acids Solution-containing MEM medium 3. Positive Control Staurosporine: 1 µmol/mL A 1 mmol/L solution prepared with DMSO was prepared with a medium so as to have a final concentration (the final concentration of DMSO was set to be 0.1%).

4. Preparation of Sample

A sample was weighed and a medium was added so as to obtain 500 µg/mL. While warming at 37° C., sonication was performed for 60 minutes to make dissolution. Filtration was performed by a 0.22 µm-filter. The 500 µg/mL solution was subjected to serial dilution in a common ratio of 10 with the medium to prepare 50, 5, 0.5, 0.05 and 0.005 µg/mL.

5. Measuring Method (1) (The day before test)

On a 96-well plate, A549 cells were seeded in a ratio of 10000 cells/100 µL/well.

(2) (Test Day)

After the medium was removed from the 96-well plate, a medium (100 µL) containing a sample or a positive control was added. Culture was carried out in a CO$_2$ incubator for 5 hours.

(3) Caspase 3/7 Reagent was added in an amount of 100 µL/well. Shaking by a plate shaker was performed at 500 rpm for one minute.

(4) Reaction was performed at room temperature while blocking light. Two hours later, fluorescence was measured (excitation wavelength: 499 nm, fluorescence wavelength: 521 nm)

8. Results

The results are shown in FIG. 1. From the results, it was found that the compound of Example 3 tends to enhance caspase 3/7 activity in all concentrations (0.005 µg/mL to 500 µg/mL) used in the test. In particular, high activity was observed at a concentration from 0.005 µg/mL to 5 µg/mL. It was presumed that an apoptosis-inducing ability is present.

Example B4

Antimicrobial/Antifungal Test

Measurement of the Minimum Inhibitory Concentration (MIC) of a Test Substance

The minimum inhibitory concentration (MIC) of test substances (Compound 3, Compound 7) on a microorganism was measured.

(Test Method)

1) Test Microbe (a) *Staphylococcus aureus* MRSAIID 1677 (methicillin-resistant *staphylococcus aureus*; MRSA) (b) *Trichophyton mentagrophytes* NBRC5466 (*trichophyton*)

2) Preparation of Microbe Solution for Inoculation

Test microbe (a): A strain cryopreserved was smeared on TSA medium and cultured at 36±1° C. for 24 hours. Grown colonies were scraped out and suspended in a test organism preparation solution, filtered with absorbent cotton. The number of cells was controlled to be about $10^{6-7}$ CFU/mL. The test microbe solution prepared was serially diluted by 10-fold and cultured at 36±1° C. for 48 hours and the microbe cells were counted.

Test microbe (b): A strain cryopreserved was applied on PDA medium and cultured at 27±2° C. for 7 days. Spores were scraped out and suspended in a test microbe preparation solution, filtered with absorbent cotton. The solution was prepared so as to have a number of spores of about $10^6$ CFU/mL. The test microbe solution prepared was serially diluted by 10-fold and cultured at 27±2° C. for 7 days and then the microbe cells were counted.

3) Serial Dilution of Test Substance

Two-fold serial dilutions of a test substance were prepared in the following procedure. To a test substance (1 mg), a medium (5 mL) for measuring the sensitivity of each microbe strains was added to obtain a stock solution of 200 µg/mL. 2 mL of the stock solution was added in the medium (2 mL) for measuring the sensitivity of each microbe strains to obtain two-fold dilution. Hereinafter, the same procedure (two-fold dilution) was repeated to obtain serial dilution solutions of the test substance each having a concentration of 100, 50, 25, 12.5, 6.3, 3.1, 1.6, 0.8, 0.4 or 0.2 µg/mL.

4) MIC Measurement

Individual serial dilutions thus prepared were dispensed in U-shaped wells of a microplate in an amount of 0.1 mL per well for necessary lines.

A test microbe solution (5 µL) was added dropwise to individual wells of the microplate. A test microbe (a) was cultured at 36±1° C. for 24 hours and a test microbe (b) was cultured at 27±2° C. for 7 days. After culture, whether the microbe proliferated or not was determined by the naked eye. The minimum concentration at which microbe cells did not proliferate was specified as an MIC value. In addition, a medium prepared by adding a test microbe solution to the medium for measuring the sensitivity was used as a negative control.

Test Results

The test results are collectively listed in Table 3. The MIC value of Compound 3 in the case of (a) MRSA was 6.3 µg/mL and the MIC value of Compound 3 in the case of (b) *trichophyton* was 100 µg/mL. The MIC value of Compound 7 in the case of (a) MRSA was 0.8 µg/mL and the MIC value of Compound 3 in the case of (b) *trichophyton* was 6.3 µg/mL.

TABLE 3

MIC value of test substance in the cace of each test microbe

| name of test substance | test microbe | |
|---|---|---|
| | MRSA | trichophyton |
| Compound 3 of Example | 6.3 | 100 |
| Compound 7 of Example | 0.8 | 6.3 |

(unit: μg/mL)

Example B5

Antimicrobial Test on Oral Bacteria
1. Antimicrobial Action on *Streptococcus mutans*
The antimicrobial effect of two types of test substances (Compound 3 and Compound 7) on *Streptococcus mutans* was evaluated.
Test Method
1) Preparation of Test Microbe
A microbe strain (*Streptococcus mutans* NBRC13955) cryopreserved was cultured in TSA medium at 36±1° C. for 18 to 24 hours. The cultured microbial cells were transferred to a fresh TSA medium and cultured at 36±1° C. for 18 to 24 hours. The grown colonies were scraped out and suspended in sterile ion-exchange water to prepare a solution having about $10^7$ CFU/mL, which was used as a test microbe solution.
2) Preparation of Test Solution
The test substance was weighed and dissolved in sterile distilled water to prepare a test solution having a concentration of 1.0 to 0.01 w/v %.
3) Bactericidal Effect Test
From individual test solutions previously kept at 25±2° C., an aliquot (10 mL) was dispensed to centrifuge tubes of 50 mL in volume. To each of the centrifuge tubes, the test microbe solution (0.1 mL) was inoculated, mixed and allowed to react. After a predetermined reaction time, the resultant test solution (1 mL) was taken out. To this, 9 mL of a deactivator (SCDLP medium (manufactured by Eiken Chemical Co., Ltd.), which was confirmed as effective deactivator), was added to inactivate the bactericidal component of the test solution. The number of microbial cells in the resultant sample solution was determined. The solution obtained by carrying out the same procedure except that a sterile physiological saline was used in place of the test solution, was used as a control.
4) Determination of the Number of Microbial Cells
Using the sample solution as a stock solution, serial dilution was performed with a sterile physiological saline to obtain 10-fold serial dilutions. 1 mL of the sample solution or each of the dilutions was aseptically transferred to a petri dish, mixed with TSA medium (20 mL), solidified and cultured at 36±2° C. for 48 hours. After the culture, colonies grown on the medium were counted to obtain the number of test microbe cells per test solution (1 mL) (lower limit of quantification: 10 CFU/test solution (1 mL)).
(Test Results)
The test results are separately shown in Table 4 (Compound 3) and Table 5 (Compound 7).
In the case of Compound 3, *Streptococcus mutans* cells were almost completely killed even at a concentration as low as 0.05 w/v % in one minute. Even at a concentration of 0.01 w/v %, the number of the cells reduced up to 1/10 in 5 minutes. Thus, bactericidal action was clearly confirmed.

In the case of Compound 7, *Streptococcus mutans* cells were almost completely killed even at a concentration as low as 0.005 w/v % in one minute. Similarly, bactericidal action was clearly confirmed.

TABLE 4

Test results of antimicrobial effect of Compound 3 on *Streptococcus mutans*

| name of test substance | concentration of test substance (w/v %) | Working time (min) | | |
|---|---|---|---|---|
| | | immediately after initiation | 1 | 5 |
| control | 0 | 370,000 | 420,000 | 380,000 |
| Compound 3 | 0.01 | | 380,000 | 34,000 |
| | 0.05 | | <10 | <10 |

Unit: CFU/test solution (1 mL)

TABLE 5

Test results of antimicrobial effect of Compound 7 on *Streptococcus mutans*

| name of test substance | concentration of test substance (w/v %) | Working time (min) | | |
|---|---|---|---|---|
| | | immediately after initiation | 1 | 5 |
| control | 0 | 420,000 | 460,000 | 380,000 |
| Compound 7 | 0.001 | | 460,000 | 280,000 |
| | 0.005 | | <10 | <10 |

Unit: CFU/test solution (1 mL)

Example B6

Antiallergy Test
1. Degranulation Suppression Test of RBL-2H3 Cells
As to Compound 3, the granule release (degranulation) suppression action on RBL-2H3 cell by IgE stimulation, which is a cell model for an allergic reaction, was examined.
1) Test Method
A test substance (50 mg) was dissolved by adding 1 mL of 50 vol % ethanol to the test substance to obtain a concentration of 50 mg/mL. The solution thus obtained was diluted with a buffer solution. In this manner, samples having a concentration of the test substance of 10, 50 and 100 μg/mL, respectively were prepared and subjected to a test. The concentrations were all indicated as the concentrations in cell supernatants.
β-Hexosaminidase abundantly present in granules of RBL-2H3 cells was used as the index of degranulation caused by IgE stimulation, and p-nitrophenol produced by the reaction with a substrate was measured by colorimetric assay. The activity values of β-hexosaminidase present within cells and released in the culture supernatant were determined to obtain the release rate of β-hexosaminidase, and then, a degranulation rate relative to an untreated control was obtained. Based on this, degranulation inhibitory action was evaluated.
Main test conditions and outline of the operation will be described below.
Cell: Rat basophil leukemic cell, RBL-2H3 [Human Sciences Foundation]
Stimulation of degranulation: Anti-DNP-IgE antibody, DNP labeled albumin [Sigma-Aldrich Corporation]

Degranulation Index: β-Hexosaminidase activity

Measurement apparatus: Microplate reader, SpectraMax M2c

[Molecular Devices Corporation]

2) Test Results

Figure 2:
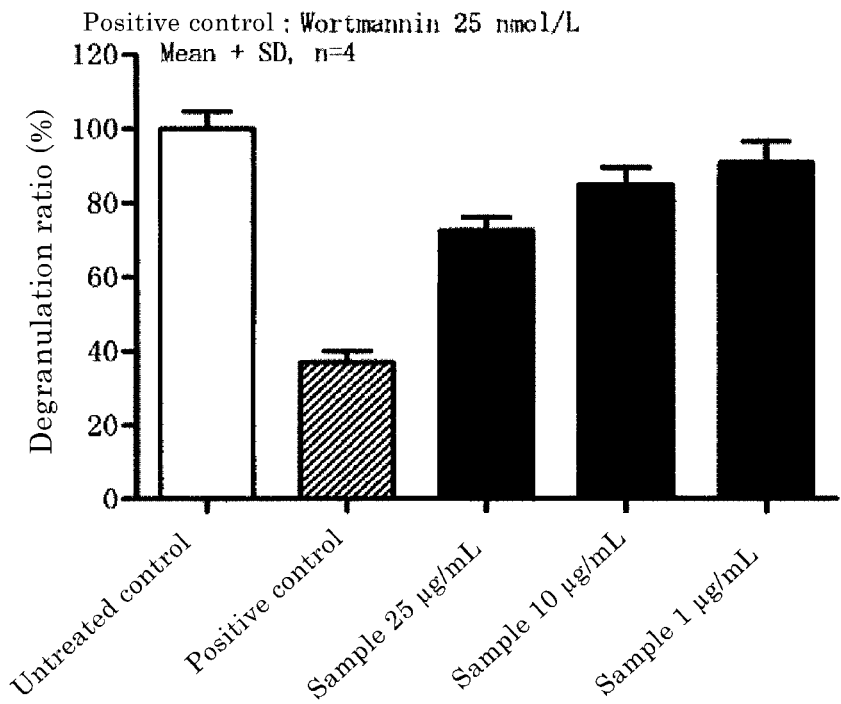
FIG. 2 shows the results of the test on the degranulation inhibitory action of Compound 3 in Example B6.

The degranulation ratios of a test substance are shown in FIG. 2 and Table 6. The sample concentration-dependent degranulation inhibitory action was confirmed in the range of a sample concentration of 10 to 100 μg/mL in the cell supernatant. A degranulation ratio of 35% was obtained at a sample concentration of 50 μg/mL in the cell supernatant and a degranulation ratio of 19% was obtained at 100 μg/mL. From this, a strong degranulation inhibitory action equivalent to that of a positive control was confirmed. In addition, cytotoxicity was not visually confirmed at any concentration.

In this test, an action to suppress granule release (degranulation) in mast cells caused by an IgE antigen stimulation is evaluated. Thus, the smaller the degranulation ratio is, the stronger the effect is

TABLE 6

Degranulation ratio of Compound 3 (n = 4)

|  | Degranulation ratio (%) |
|---|---|
| Untreated control | 100 |
| Positive control | 37 |
| Sample 100 μg/mL | 19 |
| Sample 50 μg/mL | 35 |
| Sample 25 μg/mL | 73 |
| Sample 10 μg/mL | 85 |
| Sample 1 μg/mL | 91 |

2. Validation Test in RBL-2H3 Cell (Effect on Inflammation Mediator mRNA Expression by Antigen Stimulation)

After a cell model for an allergic reaction, RBL-2H3 cells, were stimulated by an antigen, mRNA expression level of a typical inflammation mediator, TNF-α, in the cell was measured by a Real-time PCR method. In this manner, a confirmation test for anti-inflammatory effect of Compound 3 was performed.

1) Test Method

A test substance (Compound 3) (50 mg) was dissolved by adding 50 vol % ethanol (1 mL) to this to obtain an ethanol solution having a concentration of 50 mg/mL. The resultant solution was diluted with a medium. In this manner, samples having a concentration of 10 and 50 μg/mL were prepared and then subjected to a test. As a control (for comparison), Wortmannin (10 μM) was used. Herein, the concentrations were all indicated as the concentrations in cell supernatants.

RBL-2H3 cells were sensitized with anti-DNP-IgE antibody for 2 hours. A medium or a test solution was added and heat was applied at 37° C. for 10 minutes and then, a DNP-HSA solution was added. A reaction was carried out at 37° C. for 30 minutes. After completion of the reaction, total RNA was extracted from a cell fraction and cDNA was synthesized by use of Random Primer and Reverse Transcriptase. After a specific primer for a desired gene (ITNF-α,β-actin) was added, a Real-time PCR method was carried out in accordance with SYBR Green method using the resultant cDNA as a template to determine the expression level of mRNA. The expression ratio of the desired gene relative to a housekeeping gene, β-actin, was calculated. In this manner, a change in expression level relative to an untreated control was calculated.

Main test conditions and outline of the operation will be described below.

Cell: Rat basophil leukemic cell, RBL-2H3 [Human Sciences Foundation]

Antigen stimulation: Anti-DNP-IgE antibody, DNP labeled albumin

[Sigma-Aldrich Corporation]

Desired genes: IL-4, MCP-1, TNF-α, β-actin (housekeeping gene)

Measurement apparatus: StepOnePlus Real-Time PCR System [Life

Figure 7:
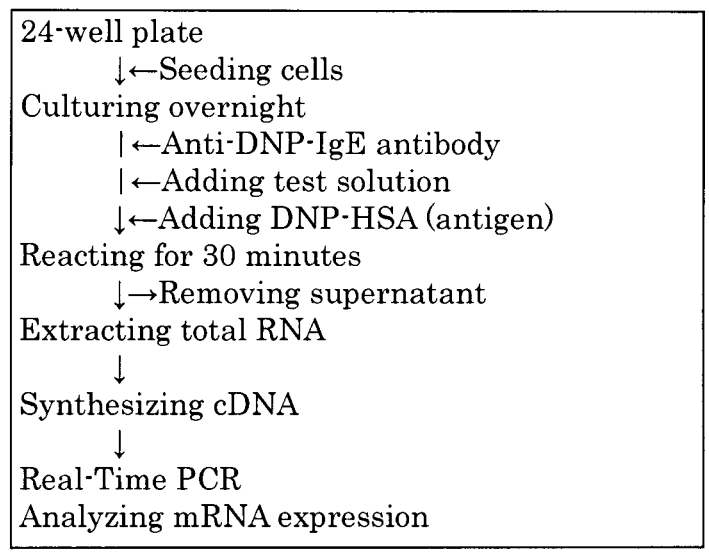
FIG. 7 shows the test conditions and an outline of the operation of "Validation test in RBL-2H3 cell" in Example B6.

Technologies Corporation] Measurement conditions: 95° C. (20 sec)→{95° C. (3 sec)→60° C. (30 sec)}×40 cycles The test conditions and outline of the operation are shown in FIG. 7.

2) Test Results

Figure 3:
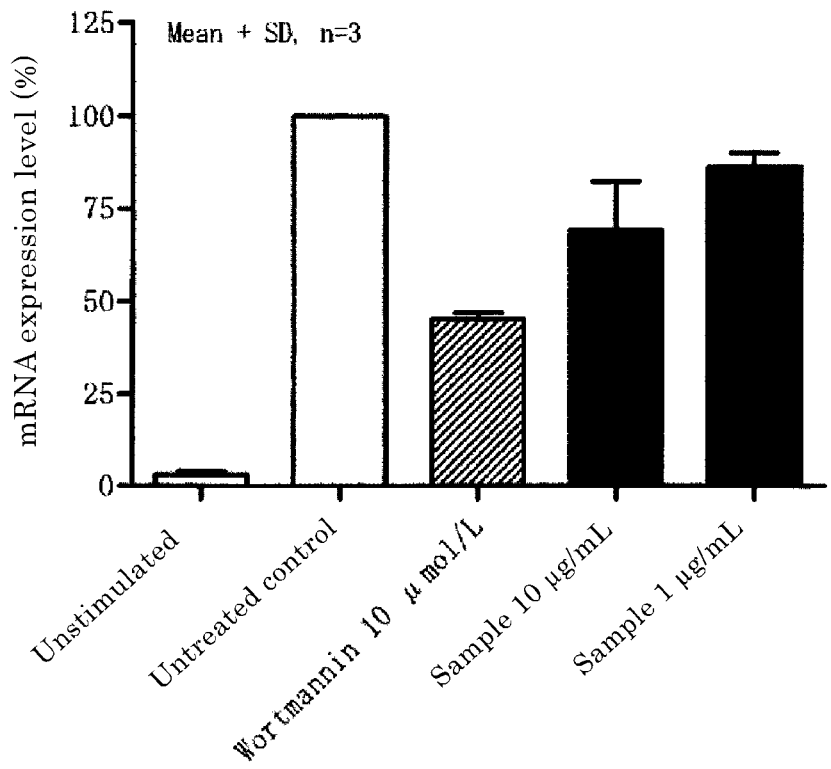
FIG. 3 shows the effect of Compound 3 on the mRNA expression level of TNF-α in Example B6.

In FIG. 3 and Table 7, the effect of Compound 3 on TNF-α mRNA expression level is shown. Suppression of the mRNA expression TNF-α, one of inflammatory mediators, was confirmed. Herein, the mRNA expression level was expressed by a relative value to that of an untreated control.

TABLE 7

Effect of Compound 3 on TNF-α mRNA expression level

|  | mRNA expression level (%) |
|---|---|
| Not stimulated | 3 |
| Untreated control | 100 |
| Wortmannin 10 μmol/L | 45 |
| Sample 10 μg/mL | 69 |
| Sample 1 μg/mL | 87 | mRNA expression level (%) was obtained based on the expression level of the untreated control as 100.

Example B7

Topoisomerase Inhibitory Action

The inhibitory action of a test substance (Compound 3) on Topoisomerase I and Topoisomerase II was examined.

1. Topoisomerase I Assay

Topoisomerase I (4 units) was subjected to the following assay performed in the assay conditions, which were determined by a preliminary examination, for a reaction time of 2 hours.

(1) An assay solution was prepared in accordance with the following table.

|  | Amount per sample | Final volume |
|---|---|---|
| Distilled water | 6.73 μL | — |
| 10 X Topo I assay buffer | 2 μL | 1X |
| Supercoiled DNA (0.25 μg/μL) | 1 μL | 0.25 μg |
| Topoisomerase I (15 units/μL) | 0.27 μL | 4 units |
| Test-substance solution (two fold concentration of final concentration) | 10 μL | Single-fold concentration |
| Total | 20 μL | — |

2. Topoisomerase II Assay

Assay was performed in accordance with the attachment to Topoisomerase II Assay Kit, as follows.

[Procedure of Assay]

(1) 10×Topo II Incomplete Assay A and 10×ATP Buffer B were mixed in equal amounts to prepare 5× Complete Assay Buffer (prepared when used).

(2) Assay solution was prepared in accordance with the following table.

|  | Amount per sample | Final volume |
|---|---|---|
| Distilled water | 4.5 μL | — |
| 5X Complete Assay Buffer | 4 μL | 1X |
| Kinetoplast DNA (0.2 μg/μL) | 1 μL | 0.2 μg |
| Topoisomerase II (2 units/μL) | 0.5 μL | 1 unit |
| Test-substance solution (two fold concentration of final concentration) | 10 μL | Single-fold concentration |
| Total | 20 μL | — |

(3) Incubated at 37° C. for 30 minutes
(4) 5 μl of 5× Stop Buffer/gel loading dye was added
(5) 1 μl of 1.3 mg/mL protease K solution (prepared with distilled water) was added (final concentration of protease K is 50 μg/mL)
(6) Incubated at 37° C. for 20 minute
(7) Total amount was applied to 1% agarose gel (containing EtBr) and analyzed by electrophoresis using a single concentration TAE buffer (prepared with distilled water).
(8) After electrophoresis, the 1% agarose gel was stained with 0.5 μg/mL EtBr solution (prepared with single concentration TAE buffer)
(9) Irradiated with UV ray and photographed.

3. Test Results

The test results are shown in Table 8.

Topoisomerase I assay

Topoisomerase I inhibitory activity was confirmed at the concentration of Compound 3 of 500 μg/mL.

Topoisomerase II assay

Topoisomerase II inhibitory activity was observed at each of the compound-3 concentrations of 5, 50 and 500 μg/mL.

TABLE 8

| | Inhibitory action on Topoisomerase I/II | | |
|---|---|---|---|
| | Final concentration | Inhibitory activity | |
| Test substance | (μg/mL) | Topoisomerase I | Topoisomerase II |
| Compound 3 | 0.5 | x | x |
| | 5 | x | o |
| | 50 | x | o |
| | 500 | o | o | o: Inhibitory activity is present
Δ: Weak inhibitory activity is present
x: No inhibitory activity is present Example B8

Angiogenesis Inhibitory Action

The angiogenesis inhibitory action of a test substance (Compound 3) was examined by use of measuring reagents and analysis software described below.

1. Measuring Reagents and Analysis Software

Angiogenesis kit (Cat. No. KZ-1000), manufactured by KURABO INDUSTRIES LTD.

Angiogenic agent VEGF-A (Cat. No. KZ-1350), manufactured by KURABO INDUSTRIES LTD.

Lumen staining kit (for staining CD31, Cat. No. ZHA-1225), manufactured by KURABO INDUSTRIES LTD.

Image analysis software: Angiogenesis Image Analyzer V2.0, manufactured by KURABO INDUSTRIES LTD.

Herein, as a culture medium, angiogenesis specific medium-2 (hereinafter referred to as the medium) provided in the above angiogenesis kit.

2. Control

Positive control: Medium containing VEGF-A (10 ng/mL)

Negative control: Medium containing VEGF-A (10 ng/mL) and Suramin (50 μmol/L)

3. Preparation of Samples

A test substance was weighed at the starting day of a test. The medium was added so as to be 500 μg/mL. Sonication was performed while heating at 37° C. for 60 minutes to be dissolved. Then, filtration was performed by a 0.22 μm filter. The 500 μg/mL-solution was serially diluted with the medium in a common ratio of 10. In this manner, 50 μg/mL and 5 μg/mL solutions were prepared. After the preparation, VEGF-A was added so as to be 10 ng/mL, which was used as a test solution. The test solution was also prepared for replacement on Days 4, 7 and 9, on the starting day of the test, and refrigerated (2 to 8° C.) until use.

4. Test Method

The test was carried out in accordance with the manual attached to an angiogenesis kit, as follows (carried out in 3 wells for each concentration (n=3 wells)).

1) A 24-well plate containing cells was put in a 5% $CO_2$ incubator of 37° C. for 3 hours.

2) To the 24-well plate containing cells, a medium containing a test solution or a control was added in a ratio of 0.5 mL/well.

3) Culture was performed at 37° C. in a 5% $CO_2$ incubator for 11 days. The test solution was replaced on Days 4, 7 and 9.

4) The medium was removed and 70% ethanol (−20° C.) was added in an amount of 1 mL/well and a reaction was performed for 30 minutes. In this manner, cells were fixed.

5) Wells were washed with a blocking solution (1% BSA/PBS).

6) Anti-CD31 antibody was allowed to react at 37° C. for one hour.

7) Wells were washed with a blocking solution (1% BSA/PBS)

8) Alkaline phosphatase-labeled anti-mouse IgG antibody was allowed to react at 37° C. for one hour.

9) Wells were washed with distilled water.

10) A substrate solution (BCIP) was added and staining was carried out at 37° C. for 15 minutes.

11) Washing was performed with distilled water and air drying was performed.

12) Image was photographed to obtain three pictures per well.

5. Image Analysis

The pictures were subjected to image analysis by use of image analysis software, Angiogenesis Image Analyzer V 2.0, and the area and length of the lumen formed were measured.

6. Results

Figure 4:
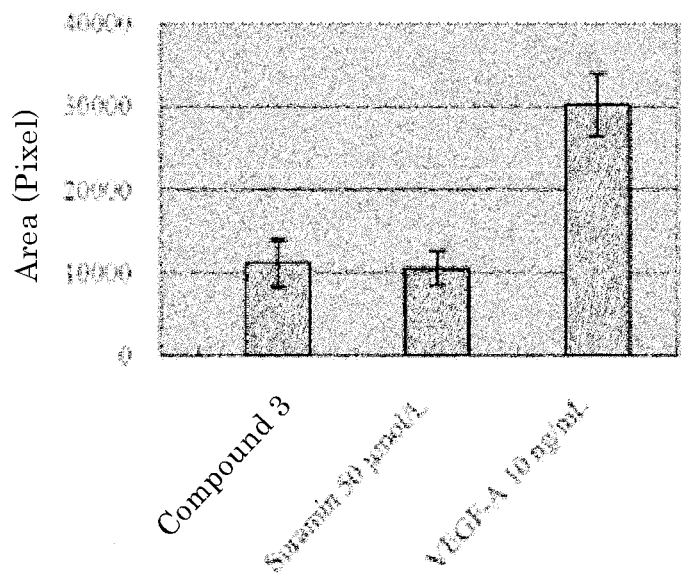
FIG. 4 shows the analysis results (area) of the angiogenesis inhibitory action of Compound 3 in Example B8.
Figure 5:
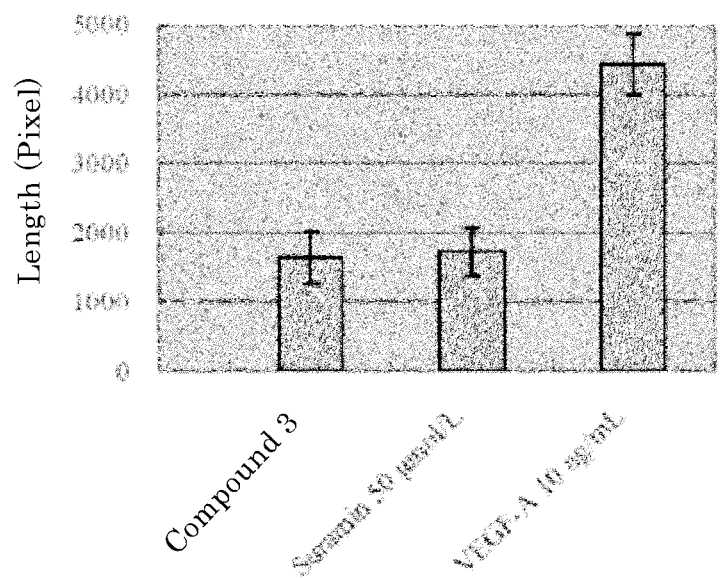
FIG. 5 shows the analysis results (length) of the angiogenesis inhibitory action of Compound 3 in Example B8.
Figure 6:
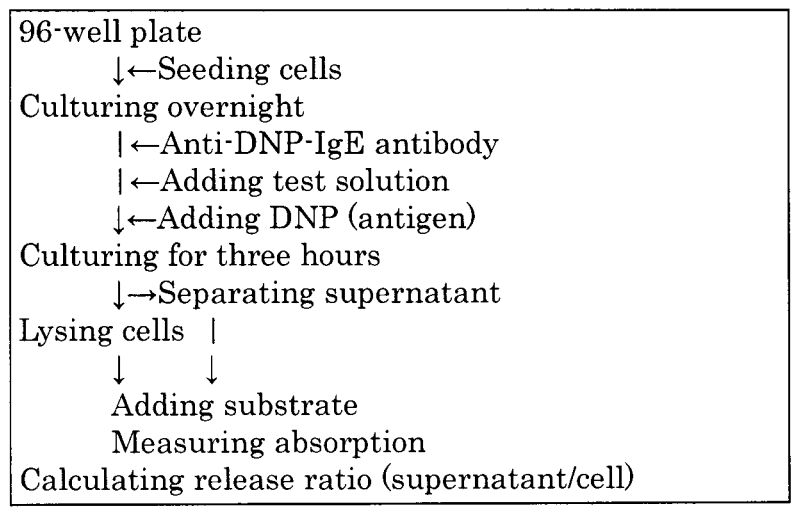
FIG. 6 shows the test conditions and an outline of the operation of "Degranulation suppression test of RBL-2H3 cells" in Example B6.

The test results are shown in FIG. 4 (area) and FIG. 5 (length). Herein, FIG. 4 and FIG. 5 show the results at a compound-3 concentration of 5 μg/mL. From the area and length data, angiogenesis inhibitory effect was confirmed.

Example B9

Evaluation of Anticancer Action

The cell proliferation inhibitory effects of a test substance (Compound 3) on various types of cancer cells were examined.

1. Measuring Reagent and Analysis Software

WST-8 Kit (Cat. No. 260-96165 or 260-96162; manufactured by Kishida Chemical Co., Ltd.) for counting cell number Software for graph making and measurement of $GI_{50}$ value: XLfit 5.2 (ID Business Solutions Ltd.)

2. Cells and Culture Conditions

Five types of cells and medium (the following Table) were used. The cells were obtained from the Research Resource Bank of the Human Sciences Foundation.

TABLE 9

| | Cell Name | Medium | Cell number (cells/100 μL) | WST-8 (Hour) |
|---|---|---|---|---|
| 1 | A549 | MEM + 10% FBS + NEAA | 1000 | 2 |
| 2 | Hep G2 | MEM + 10% FBS + NEAA | 1000 | 3 |
| 3 | MKN1 | RPMI1640 + 10% FBS | 5000 | 2 |
| 4 | HL60 | RPMI1640 + 10% FBS | 2500 | 4 |
| 5 | MCF-7 | MEM + 10% FBS + NEAA + 1 mmol/L of Sodium pyruvate + 10 μg/mL of Insulin | 5000 | 3 |

DMEM medium: D5796; Sigma-Aldrich Japan
RPMI1640: R8758; Sigma-Aldrich Japan
MEM medium: M4655; Sigma-Aldrich Japan
FBS: Fetal calf serum (inactivated (heat treatment at 60° C. for 30 minutes) and put in use)
Insulin: 12585-014, Invitrogen 3. Preparation of Sample On the day when a sample was to be added, the sample was weighed and a medium for each type of cells was added so as to be 500 μg/mL. Sonication was performed while warming at 37° C. for 60 minutes to be dissolved. Then, filtration was performed by a 0.22 m-filter. The 500 μg/mL-solution was diluted with the medium for each type of cells to prepare 200 μg/mL, 60 μg/mL, 20 μg/mL, 6 μg/mL, 2 μg/mL, 0.6 μg/mL and 0.2 μg/mL solutions, which were specified as two-fold concentration test solutions (the final concentrations of the test substance were 250 g/mL, 100 μg/mL, 30 μg/mL, 10 μg/mL, 3 μg/mL, 1 μg/mL, 0.3 μg/mL, 0.1 g/mL, respectively).

4. Test Method

Test was performed as follows (test was carried out using three wells for each concentration (n=3 (wells)).

(1) Cells cryopreserved at −150° C. were thawed in a warm bath of 37° C. and then cultured on the medium described in the above Table by using a 25 cm²-flask or a 75 cm²-flask in a $CO_2$ incubator (37° C., 5% $CO_2$). While a degree of cell proliferation was observed, a subculture was carried out in an appropriate dilution rate.

(2) (The day before test)

The number of cells was controlled as shown in Table 9 and the cells were seeded in a 96-well plate in a ratio of 100 μL/well. A blank well containing medium in a ratio of 100 μL/well and having no cells seeded was also prepared.

(3) Culture was performed in a $CO_2$ incubator (37° C., 5% $CO_2$) for about 24 hours.

(4) To a 96-well plate containing cells, a two-fold concentration test solution or the medium was added in a ratio of 100 μL/well.

(5) Culture was performed in a $CO_2$ incubator (37° C., 5% $CO_2$) for about 72 hours (HL60 cells alone were cultured for about 96 hours).

(6) (HL60 cells)

A 96-well plate was taken out from the $CO_2$ incubator and a WST-8 Kit was added in a ratio of 20 μL/well.

(Cells except HL60 cells)

96-well plates were taken out from the $CO_2$ incubator and the medium was removed. A fresh medium was added in a ratio of 200 μL/well and WST-8 Kit was added in a ratio of 20 μL/well.

(7) Reaction was performed in a $CO_2$ incubator (37° C., 5% $CO_2$) for a predetermined time (see the above Table).

(8) Absorbance values at 450 nm and 650 nm were measured to calculate O.D. 450 and O.D. 650.

5. Calculation

With respect to individual wells of each concentration, proliferation inhibition ratio (%) was obtained in accordance with the expression:

proliferation inhibition ratio (%)= $\{1-(OD_{drug\text{-}exposed\ wells}-OD_{blank\ wells})/(OD_{drug\text{-}free\ wells}-OD_{blank\ wells})\} \times 100$ Then, the concentration ($GI_{50}$) at which proliferation is inhibited by 50% was calculated by use of XLfit 5.2 (ID Business Solutions Ltd.).

$OD_{drug\text{-}exposed\ wells}$: absorbance of a well containing a sample $OD_{drug\text{-}free\ wells}$: O.D. value of a well containing no sample (average value (triplicate))

$OD_{blank\ wells}$: O.D. value of blank well (no cells seeded) (average value (triplicate))

6. Results

The $GI_{50}$ values of the test substance (Compound 3) on various types of cancer cells obtained by the test are shown in Table 10. From the results, the cell proliferation inhibitory effect on any one of the cancer cells was confirmed.

TABLE 10

| $GI_{50}$ values of Compound 3 | |
|---|---|
| Name of cell | $GI_{50}$ value |
| A549 (lung cancer) | 13.3 |
| Hep G2 (liver cancer) | 9.8 |
| MKN1 (stomach cancer) | 5.1 |
| HL60 (myelocytic leukemia) | 1.7 |
| MCF-7 (breast cancer) | 13.6 |

(Unit: μg/ml)

The invention claimed is:

1. A pharmaceutical composition comprising an aryloyl (oxy or amino)pentafluorosulfanylbenzene compound represented by general formula (I), a pharmaceutically acceptable salt thereof or a prodrug thereof:

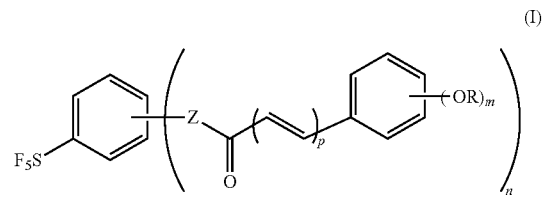

wherein,
p is an integer of 0 or 1;
m is an integer of 0 to 5;
n is an integer of 1 to 3;
Z represents —O— or —NH—;
R represents hydrogen atom, alkyl, alkenyl, alkenyl, cycloalkyl, piperidinyl, pyrrolidinyl, tetrahydropyranyl, tetrahydrofuranyl, morpholyl, aralkyl, aryl, heteroaryl, acyl, —C(=O)N($R^2$)($R^3$), —Si($R^4$)($R^5$)($R^6$), —B($R^7$)($R^8$), —S(=O)$_2$ ($R^9$), or —P(=O)($R^{10}$)($R^{11}$);
wherein $R^2$ to $R^{11}$ independently of one another, represent hydrogen atom, hydroxy, alkyl, cycloalkyl, alkenyl, alkynyl, aralkyl, aryl, heteroaryl, alkoxy, aryloxy or amino; and among $R^2$ to $R^{11}$, two adjacent groups may be bonded together to form a ring;
if m and/or n is 2 or more, plural R groups may be identical to or different from each other, and adjacent R groups may be bonded together to form a ring;
in addition, any of hydrogen atoms on carbons of a benzene ring may be optionally substituted with at least one substituent selected from the group consisting of alkyl, alkenyl, alkynyl, alkoxy, halogen atom, hydroxyl, nitro and amino.

2. The pharmaceutical composition according to claim 1, wherein the aryloyl(oxy or amino)pentafluorosulfanylbenzene compound is at least one selected from the group consisting of:
Compound 1: 4-benzoylaminopentafluorosulfanylbenzene
Compound 2: 4-(3,4,5-tribenzyloxybenzoylamino)pentafluorosulfanylbenzene,
Compound 3: 4-(3,4,5-trihydroxybenzoylamino)pentafluorosulfanylbenzene,
Compound 4: 4-(3,4-diacetoxycinnamoylamino)pentafluorosulfanylbenzene,
Compound 5: 4-(3,4-dihydroxycinnamoylamino)pentafluorosulfanylbenzene,
Compound 6: 4-(3,4,5-tribenzyloxybenzoyloxy)pentafluorosulfanylbenzene,
Compound 7: 4-(3,4,5-trihydroxybenzoyloxy)pentafluorosulfanylbenzene,
Compound 8: 3-(3,4,5-trihydroxybenzoyloxy)pentafluorosulfanylbenzene,
Compound 9: 4-(3,4,5-triacetoxybenzoyloxy)pentafluorosulfanylbenzene,
Compound 10: 3-(3,4,5-tribenzyloxybenzoylamino)pentafluorosulfanylbenzene,
Compound 11: 3-(3,4,5-trihydroxybenzoylamino)pentafluorosulfanylbenzene,
Compound 12: 3-(3,4,5-trihydroxybenzoylamino)-4-hydroxypentafluorosulfanylbenzene,
Compound 13: 3,4-bis(3,4,5-tribenzyloxybenzoylamino)pentafluorosulfanylbenzene,
Compound 14: 3,4-bis(3,4,5-trihydroxybenzoylamino)pentafluorosulfanylbenzene,
Compound 15: 4-hydroxy-3,5-bis(3,4,5-tribenzyloxybenzoylamino)pentafluorosulfanylbenzene,
Compound 16: 4-hydroxy-3,5-bis(3,4,5-trihydroxybenzoylamino)pentafluorosulfanylbenzene,
Compound 17: 4-(3,4,5-tribenzyloxybenzoylamino)-3-(3,4,5-tribenzyloxybenzoyloxy)pentafluorosulfanylbenzene,
Compound 18: 4-(3,4,5-trihydroxybenzoylamino)-3-(3,4,5-trihydroxybenzoyloxy)pentafluorosulfanylbenzene,
Compound 19: 4-(3,4-methylenedioxycinnamoylamino)pentafluorosulfanylbenzene,
Compound 20: 4-(4-acetoxy-3-methoxycinnamoylamino)pentafluorosulfanylbenzene,
Compound 21: 4-(4-hydroxy-3-methoxycinnamoylamino)pentafluorosulfanylbenzene,
Compound 22: 4-(3,4-diacetoxycinnamoyloxy)pentafluorosulfanylbenzene,
Compound 23: 4-(2,4,6-trihydroxybenzoylamino)pentafluorosulfanylbenzene,
Compound 24: 4-(3,4,5-trihydroxycinnamoylamino)pentafluorosulfanylbenzene,
Compound 25: 4-(3,4,5-triacetoxycinnamoylamino)pentafluorosulfanylbenzene,
Compound 26: 4-(3,5-bis(3-methyl-2-butenyloxy)benzoylamino)pentafluorosulfanylbenzene,
Compound 27: 4-(4-(3-methyl-2-butenyloxy)-3-methoxybenzoylamino)pentafluorosulfanylbenzene,
Compound 28: 4-(4-(2-propenyloxy)-3-methoxybenzoylamino)pentafluorosulfanylbenzene,
Compound 29: 4-(2,3,4-tris(3-methyl-2-butenyloxy)benzoylamino)pentafluorosulfanylbenzene,
Compound 30: 4-(4-hydroxy-5-(2-propenyl)-3-methoxybenzoylamino)pentafluorosulfanylbenzene,
Compound 34: 4-(4-(3-methyl-2-butenyloxy)-3-methoxybenzoyloxy)pentafluorosulfanylbenzene,
Compound 35: 4-(cinnamoylamino)pentafluorosulfanylbenzene,
Compound 36: 4-(cinnamoyloxy)pentafluorosulfanylbenzene,
Compound 37: 4-(4-(3-methyl-2-butenyloxy)-3-methoxycinnamoylamino)pentafluorosulfanylbenzene,
Compound 38: 4-(4-(2-propenyloxy)-3-methoxycinnamoylamino)pentafluorosulfanylbenzene,
Compound 39: 4-(3,4-bis(3-methyl-2-butenyloxy)cinnamoylamino)pentafluorosulfanylbenzene,
Compound 40: 4-(2,4-bis(3-methyl-2-butenyloxy)cinnamoylamino)pentafluorosulfanylbenzene,
Compound 41: 4-(3-(3-methyl-2-butenyloxy)-4-methoxycinnamoylamino)pentafluorosulfanylbenzene,
Compound 42: 4-(4-(2-butenyloxy)-3-methoxycinnamoylamino)pentafluorosulfanylbenzene,
Compound 43: 4-(4-(3-methyl-2-butenyloxy)-3,5-dimethoxycinnamoylamino)pentafluorosulfanylbenzene,
Compound 44: 4-(4-(1-methyl-2-propenyloxy)-3-methoxycinnamoylamino)pentafluorosulfanylbenzene,
Compound 45: 4-(4-hydroxy-3-methoxybenzoylamino)pentafluorosulfanylbenzene,
Compound 46: 4-(4-hydroxy-5-(2-propenyl)-3-methoxycinnamoylamino)pentafluorosulfanylbenzene,
Compound 47: 4-(4-hydroxy-5-(2-butenyl)-3-methoxycinnamoylamino)pentafluorosulfanylbenzene,
Compound 48: 4-(3-(1,1-dimethyl-2-propenyloxy)benzoylamino)pentafluorosulfanylbenzene,
Compound 49: 4-(2,3,4-trihydroxybenzoylamino)pentafluorosulfanylbenzene,
Compound 50: 4-(3,5-dihydroxybenzoylamino)pentafluorosulfanylbenzene,
Compound 51: 4-(2,4-dihydroxycinnamoylamino)pentafluorosulfanylbenzene,
Compound 52: 4-(3-hydroxy-4-methoxycinnamoylamino)pentafluorosulfanylbenzene,
Compound 53: 4-(4-hydroxy-3,5-dimethoxycinnamoylamino)pentafluorosulfanylbenzene,
Compound 54: 4-(2,3,4-tripropenyloxybenzoylamino)pentafluorosulfanylbenzene,
Compound 55: 4-(2,4,6-trihydroxybenzoylamino)pentafluorosulfanylbenzene, Compound 56: 4-(3,4-dihydroxycinnamoylamino)pentafluorosulfanylbenzene,
Compound 57: 4-(4-hydroxy-3-fluorobenzoylamino)pentafluorosulfanylbenzene,
Compound 58: 4-(3-hydroxy-4-fluorobenzoylamino)pentafluorosulfanylbenzene,
Compound 59: 4-(4-nitro-3-methoxybenzoylamino)pentafluorosulfanylbenzene,
Compound 60: 4-(4-amino-3-methoxybenzoylamino)pentafluorosulfanylbenzene,
Compound 61: 4-(4-aminobenzoylamino)pentafluorosulfanylbenzene,
Compound 62: 4-(4-nitrobenzoylamino)pentafluorosulfanylbenzene,
Compound 63: 4-(4-aminobenzoylamino)pentafluorosulfanylbenzene hydrochloride salt,
Compound 64: 4-(3-allyloxybenzoylamino)pentafluorosulfanylbenzene,
Compound 65: 4-(3-hydroxybenzoylamino)pentafluorosulfanylbenzene,
Compound 93: 4-(2-allyl-3-hydroxybenzoylamino)pentafluorosulfanylbenzene,
Compound 94: 4-(4-allyl-3-hydroxybenzoylamino)pentafluorosulfanylbenzene,
Compound 95: 4-(2,4,6-tris(3-methyl-2-butenyloxy)benzoylamino)pentafluorosulfanylbenzene,
Compound 96: 4-(4-(1,1-dimethyl-2-propenyloxy)-3-fluorobenzoylamino)pentafluorosulfanylbenzene,
Compound 97: 4-(4-hydroxy-3-fluoro-5-(3-methyl-2-butenyl)benzoylamino)pentafluorosulfanylbenzene,
Compound 98: 4-(4-(1,1-dimethyl-2-propenyloxy)-3-fluoro-cinnamoylamino)pentafluorosulfanylbenzene, and
Compound 99: 4-(4-hydroxy-3-fluoro-5-(3-methyl-2-butenyl)cinnamoylamino)pentafluorosulfanylbenzene.

* * * * *